United States Patent [19]

Bond et al.

[11] Patent Number: 4,905,676

[45] Date of Patent: * Mar. 6, 1990

[54] EXERCISE DIAGNOSTIC SYSTEM AND METHOD

[75] Inventors: Malcolm L. Bond, Winters; Philip T. Dempster, Davis, both of Calif.

[73] Assignee: Loredan Biomedical, Inc., Davis, Calif.

[*] Notice: The portion of the term of this patent subsequent to Jul. 22, 2003 has been disclaimed.

[21] Appl. No.: 845,861

[22] Filed: Mar. 28, 1986

Related U.S. Application Data

[63] Continuation-in-part of Ser. No. 568,751, Jan. 6, 1984, Pat. No. 4,601,468.

[51] Int. Cl.$^4$ ............................................. A63B 21/00
[52] U.S. Cl. ................................. 128/25 R; 272/130
[58] Field of Search .................. 272/130, 73, 134; 128/25 R

[56] References Cited

U.S. PATENT DOCUMENTS

| | | | |
|---|---|---|---|
| 3,848,467 | 11/1974 | Flavell | 272/129 |
| 3,869,121 | 3/1975 | Flavell | 272/129 |
| 4,502,681 | 3/1985 | Blomquist | 272/142 |
| 4,628,910 | 12/1986 | Krukowski | 272/129 |
| 4,691,694 | 9/1987 | Boyd et al. | 272/129 |
| 4,711,450 | 12/1987 | McArthur | 272/130 |

Primary Examiner—Leo P. Picard
Attorney, Agent, or Firm—Lowell C. Bergstedt

[57] ABSTRACT

A muscle exercise and diagnostic system which includes a lever arm, a mounting arrangement for mounting the lever arm for rotation about a fixed axis, and a connecting arrangement for connecting a selected portion of the human body to the lever arm for rotation with the lever arm about a selected anatomical axis of rotation. The connecting arrangement establishes a fixed tangential mounting relation and a sliding radial mounting relation between the lever arm and the body portion. This permits free radial movement of the connecting arrangement relative to the fixed axis during an exercise motion. A velocity control arrangement is coupled to the lever arm for limiting the maximum permitted rotational velocity to a value predetermined in accordance with a preselected velocity control function which includes measured values of the distances from the point of attachment to the anatomical axis and to the fixed axis. An arrangement is provided for inputting these measured values to a velocity control arrangement. One such arrangement continuously registers with a potentiometer the distance from the connection point to the fixed axis and supplies that registered distance value to the velocity control computer. The measured value of distance from connection point to anatomical axis is inputted by a manual dial connected to a potentiometer.

34 Claims, 25 Drawing Sheets

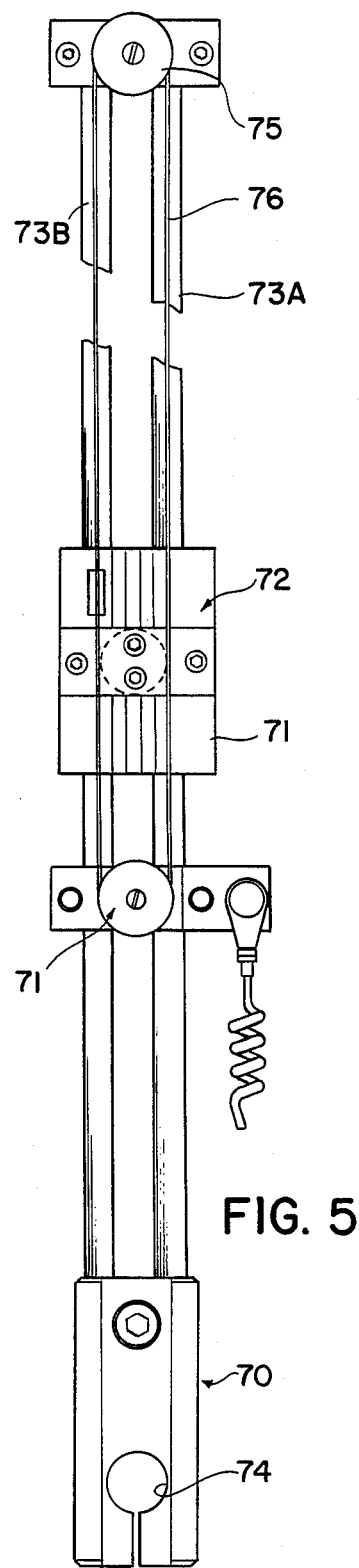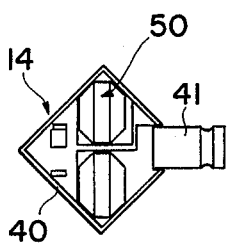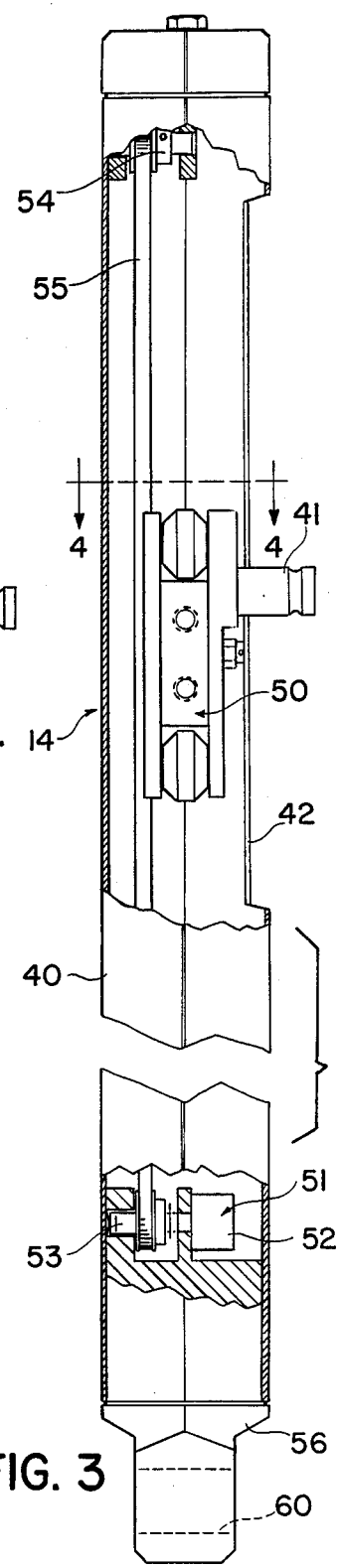
FIG. 5
FIG. 4
FIG. 3

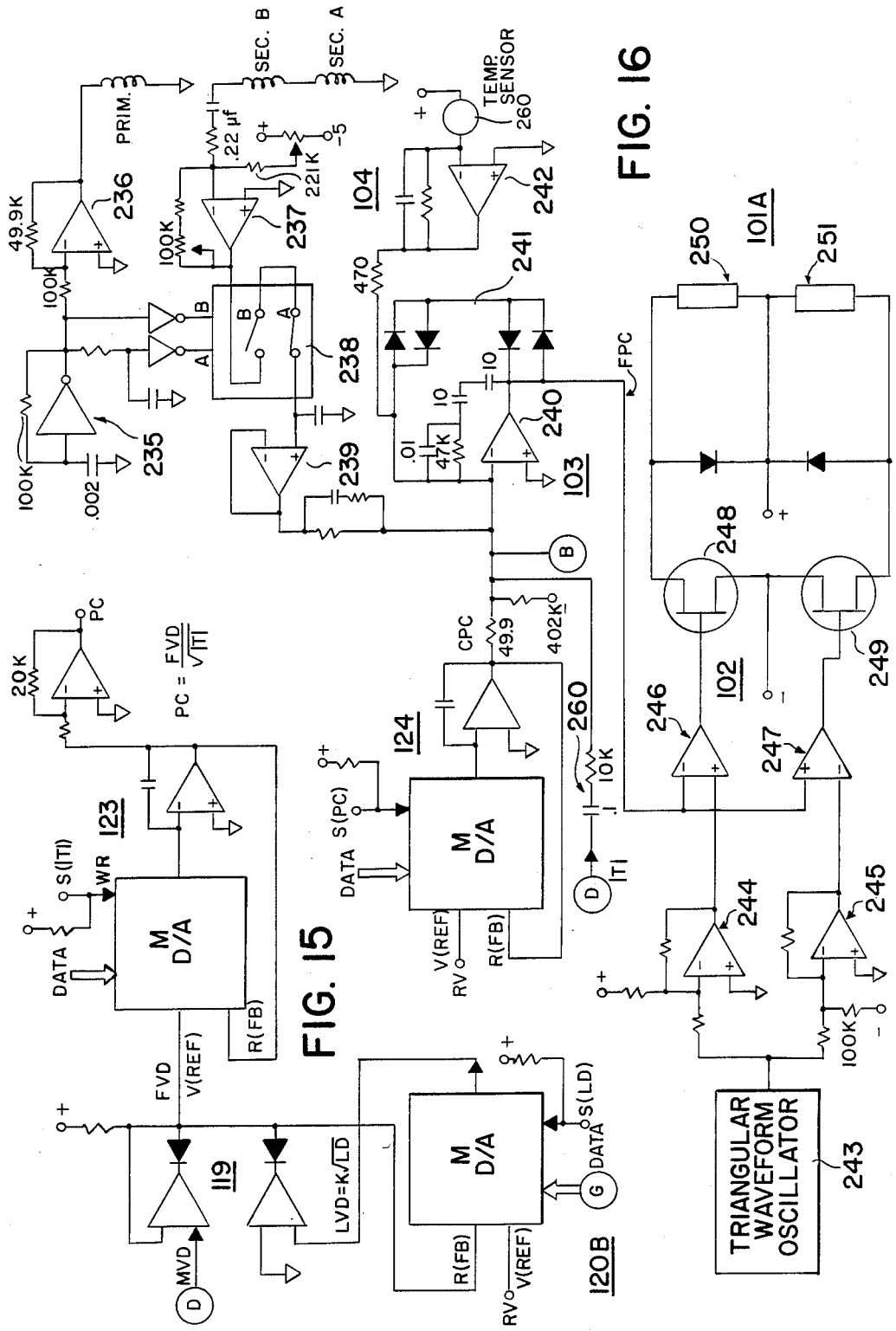

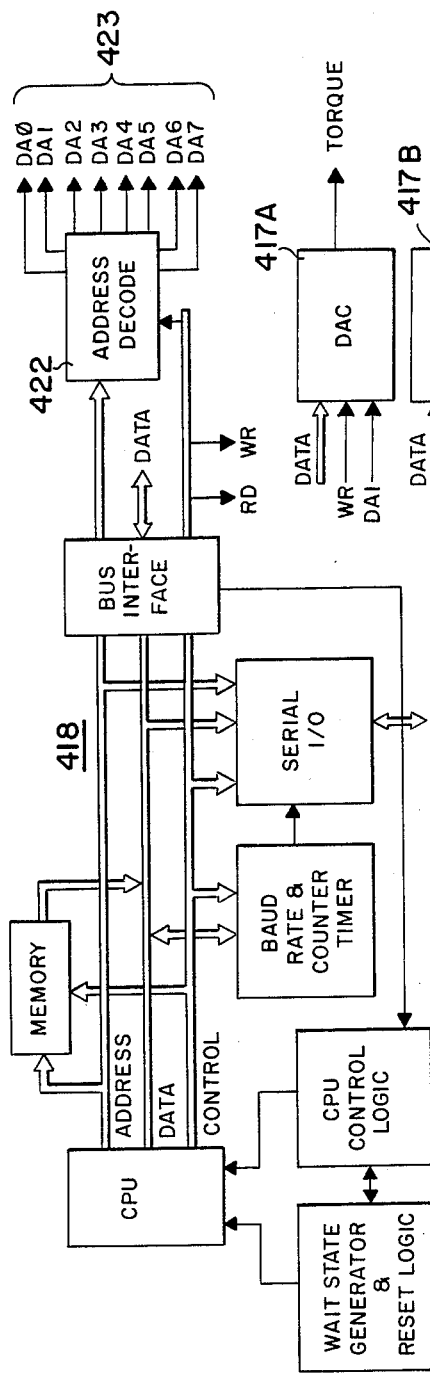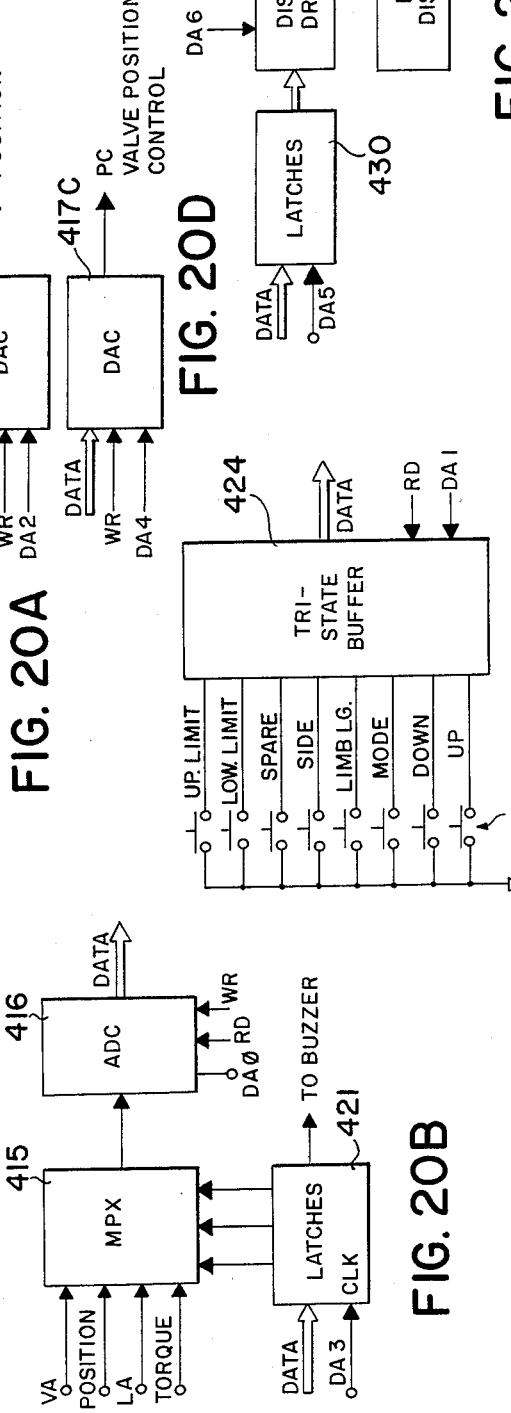

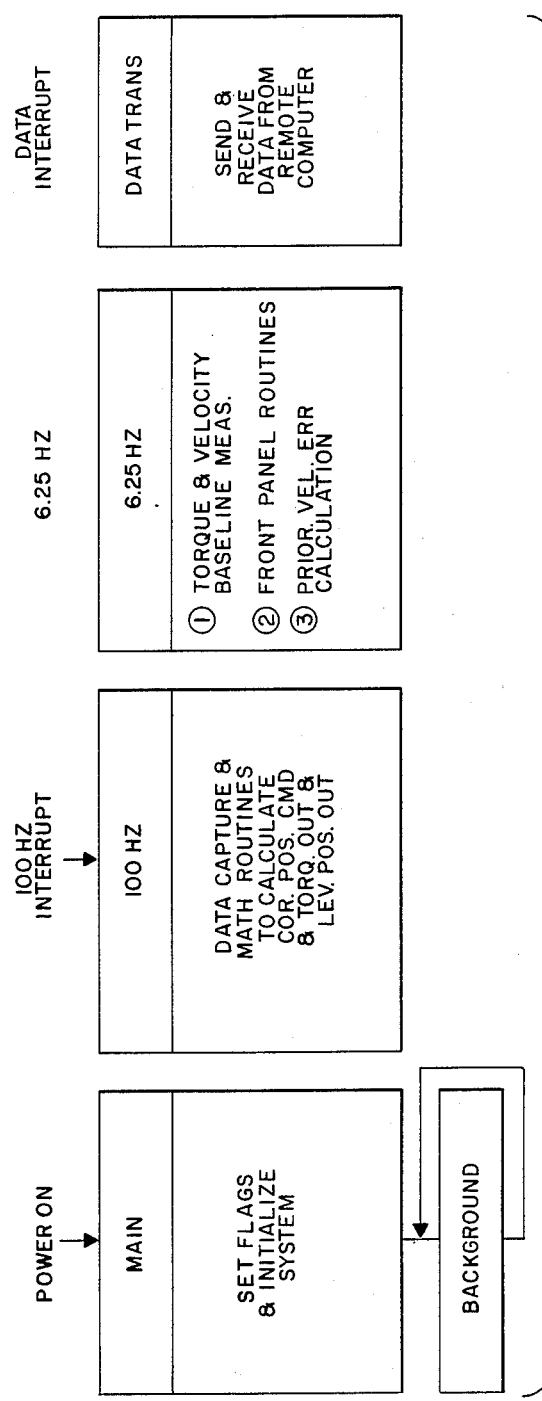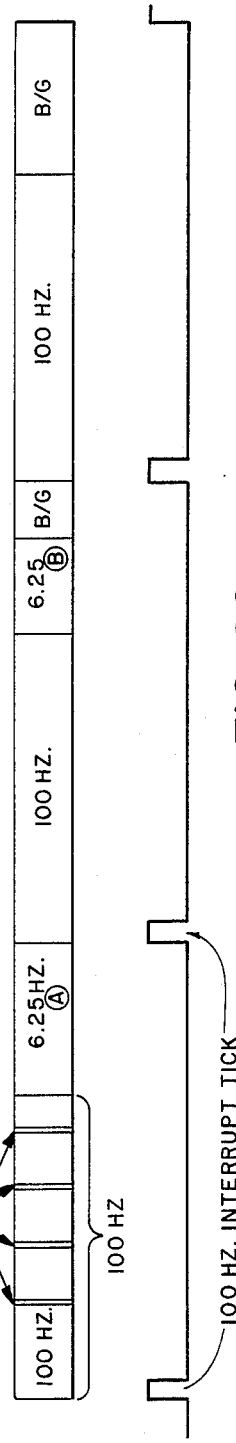
FIG. 21
FIG. 22

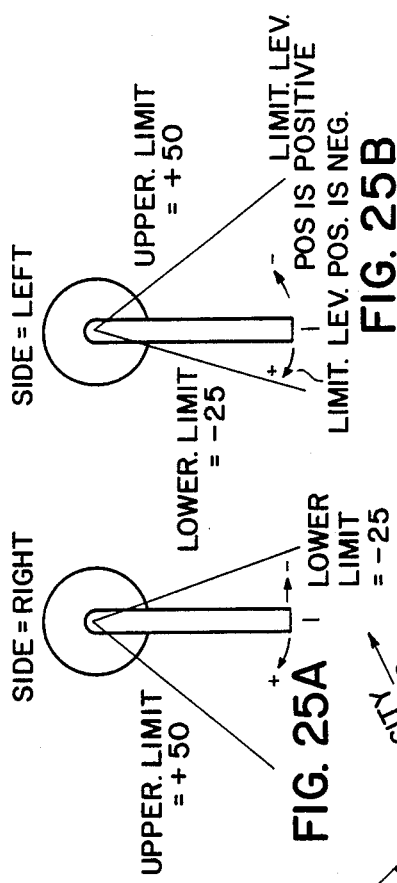
FIG. 25A
FIG. 25B
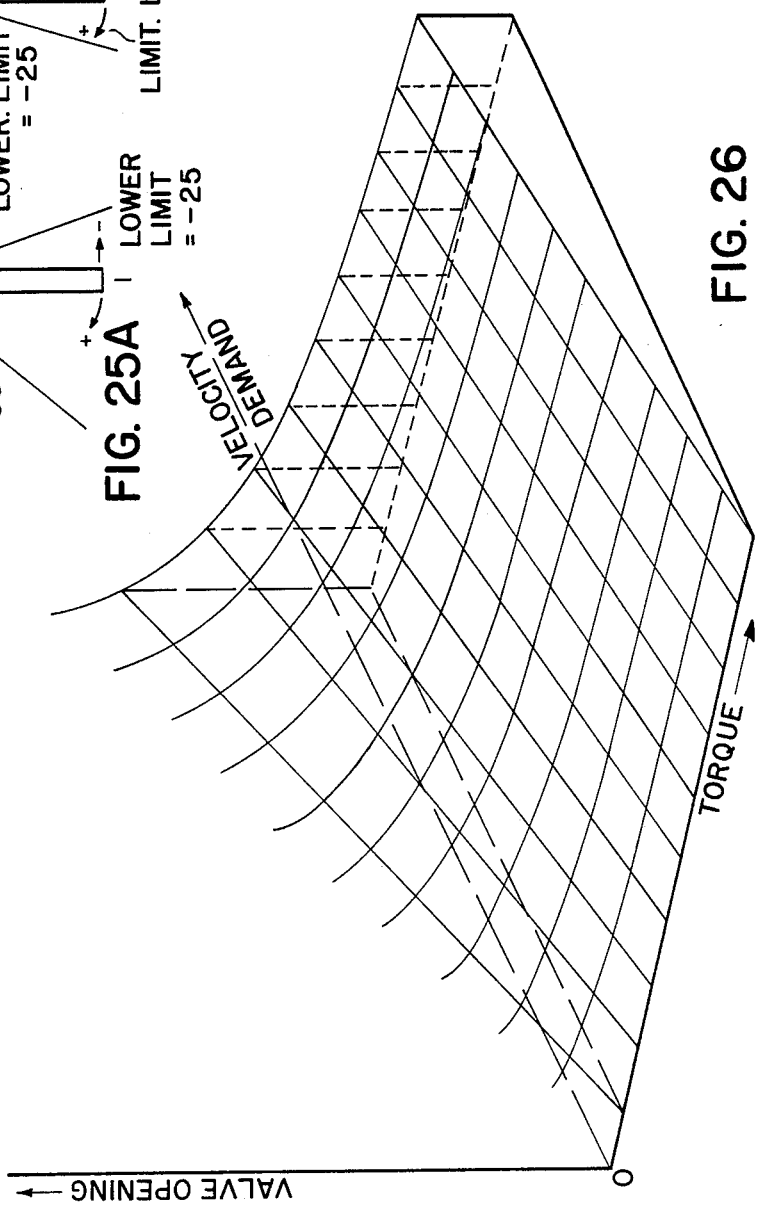
FIG. 26

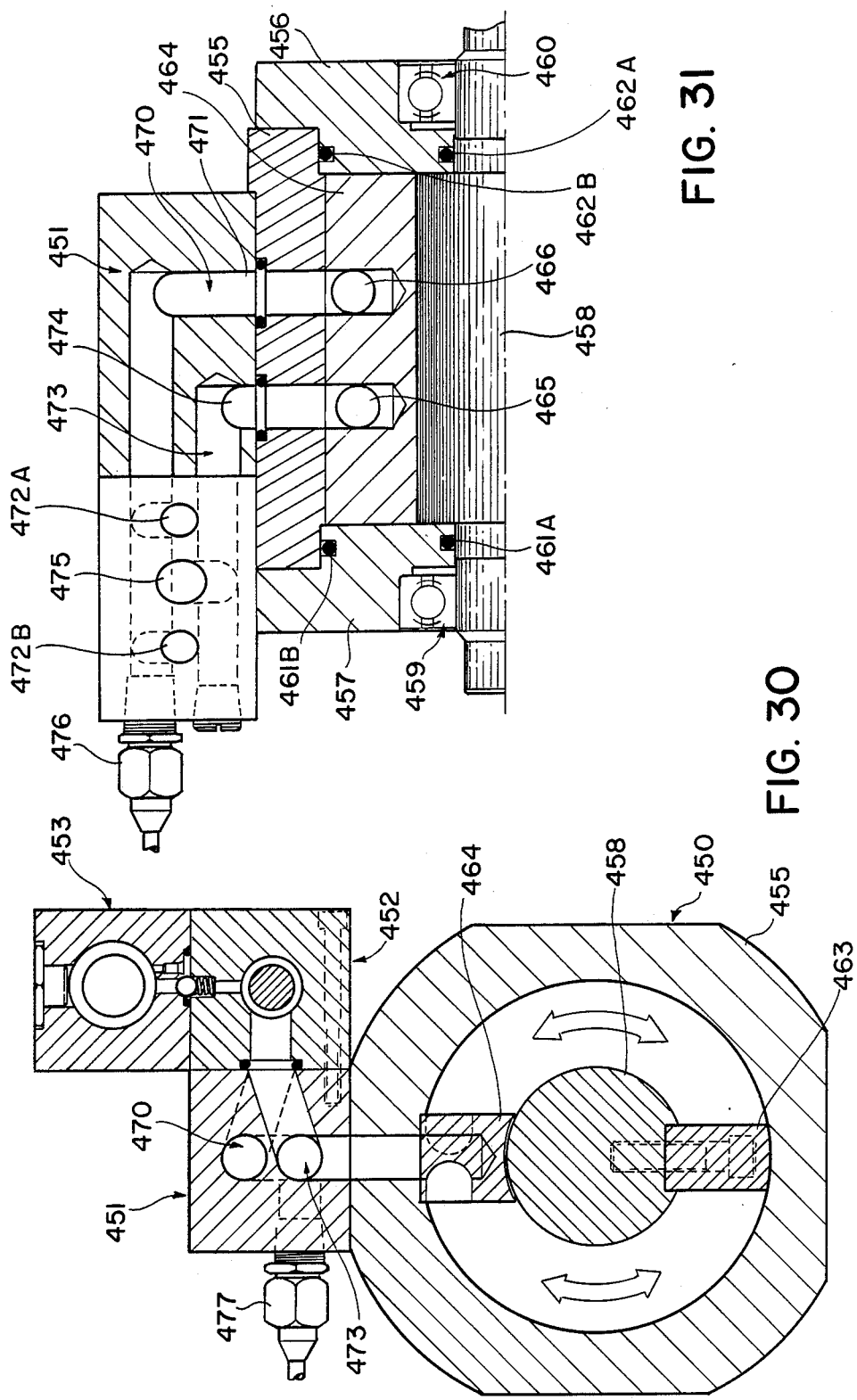

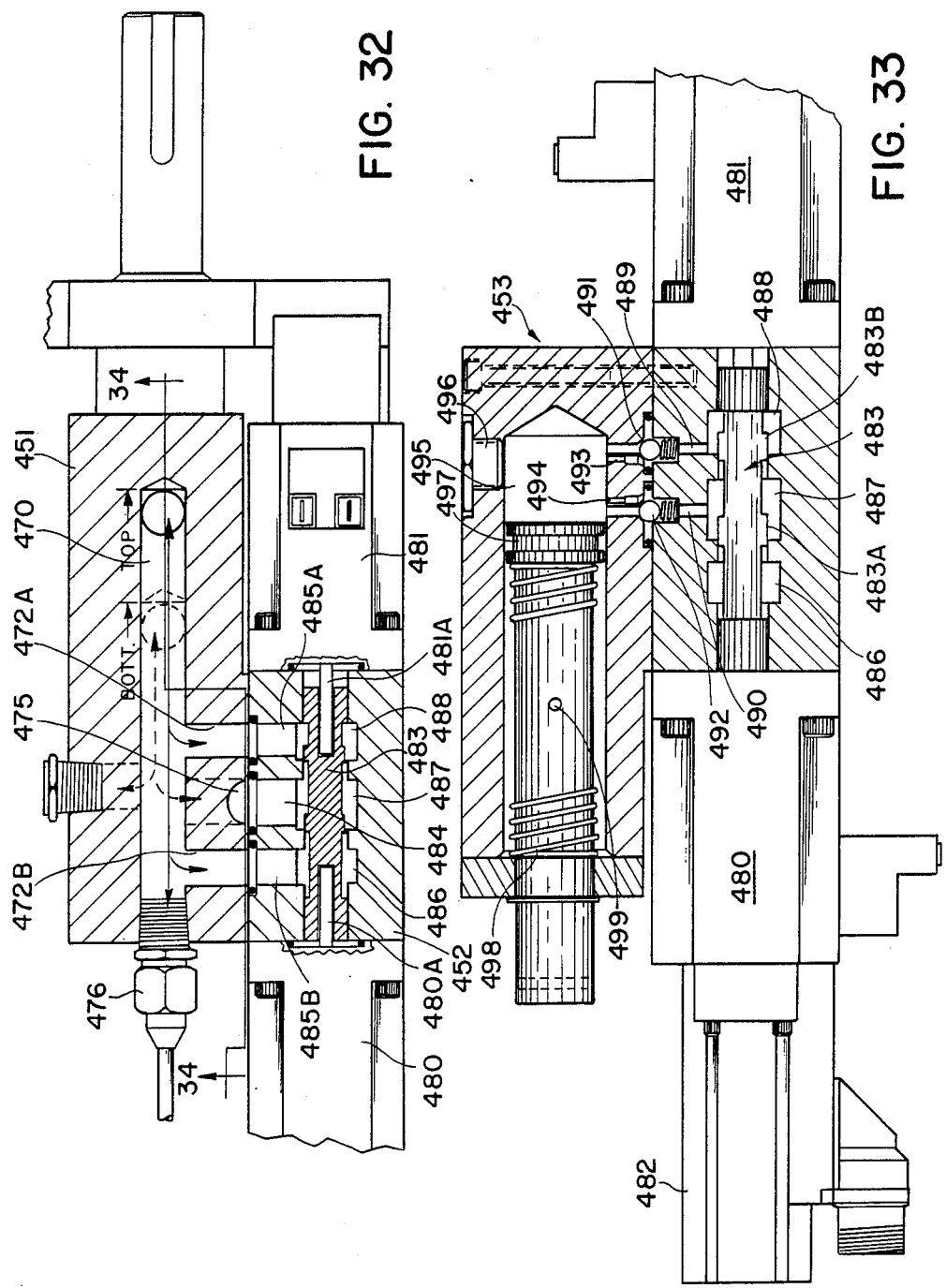

EXERCISE DIAGNOSTIC SYSTEM AND METHOD

CROSS-REFERENCE TO RELATED APPLICATIONS

This application is a continuation-in-part of out copending and commonly assigned U.S. patent application Ser. No. 568,751, filed Jan. 6, 1984 U.S. Pat. No. 4,601,468 issued 7/22/86.

Cross-reference to Related Applications
Field of the Invention
Background and Prior Art
Summary of the Invention
  1. Objects of the Invention
  2. Features and Advantages of This Invention
    a. The System Features
      (1) Radially Floating Body to Lever Arm Mounting
      (2) Proportioning the Velocity Demand Signal
      (3) Predictive Control Function Using a Rotary Actuator and Torque/Velocity Control of Valve Position
      (4) Digital Computer Real Time Control
      (5) Precision Velocity Calibration
      (6) Torque and Velocity Baseline Correction
    b. The Method Features
      (1) Radially Floating Attachment
      (2) Proportioned Velocity Demand
      (3) Limits on Range of Motion
      (4) Control of Rotary Actuator and Valve with Velocity/Torque Predictive Function
        (a) Velocity/Torque Correction Factor Array
      (5) Exercise Method Using Rotary Actuator and Control Valve Controlled with Velocity/Torque Predictive Function
Brief Description of Drawing Figures
Detailed Description of Embodiments of the Invention
  1. Incorporation of the Invention in an Isokinetic Station
  2. The Passive Resistance System and Method of This Invention
  3. Basic System Concepts of the Invention
    a. Basic Concept of Radially Floating Patient to Shaft Coupling
    b. Case History of Patient Benefits
  4. The Analog Computer Control Circuit Embodiment
    a. Control Panel
    b. General Concepts
    c. Optional Electronic Stop or Limit Function
    d. Specific Circuit Embodiment of the Analog Control System of this Invention
  5. The Digital Computer Control Circuit Embodiment
    a. Control Panel Arrangement
    b. General Digital System Concepts
    c. The Software Control System and Method
      (1) Interwoven Interrupt Program Structure
      (2) The MAIN Software Routine
      (3) The 100 Hz Routine
        (a) Baseline Correction on Velocity and Torque
        (b) Determining Limit Velocity Demand Signal LIM.VEL.DEM Based on Active Limit and the Current Lever Arm Position
          (b.1) Determining the Active Limit
          (b.2) Calculating the LIMIT.DELTA
        (c) Determining a Corrected Velocity Demand Signal
          (c.1) Proportioning the Velocity and Signal
          (c.2) Selecting the Minimum of VEL.DEM.PROP and LIM.VEL.DEM
          (c.3) Calculating the Current System Error
          (c.4) Calculating Corrected Velocity Demand
        (d) Determining a Value Position Command Signal For the Flow Control Valve
          (d.1) Determining the Torque Factor
          (d.2) Determining a Velocity/Torque Correction Factor
        (e) Determining a Corrected valve Position Command
        (f) Updating V.T.TABL Based On CUR.SYS.ERR
        (g) Determining the Output Analog Signals for Torque and Lever Position
        (h) The Valve Position Command Algorithm
      (4) The 6.25 Hz Routine
        (a) The PRIOR.VEL.ERR Routine
        (b) The Baseline Value Routine for Determining TORQ.BL and VEL.BL
  6. Control Mode Flexibility Provided by the Digital Signal Processing Embodiment of the System and Method of this Invention
  7. The Actuator and Flow Control Valve Components Employed in the System of This Invention
Claims

FIELD OF THE INVENTION

This invention relates generally to exercise systems and methods and, more specifically, to exercise and diagnostic systems and methods which permit evaluation and improvement of the performance of the human skeletal and musculature systems in both training and rehabilitation situations.

BACKGROUND AND PRIOR ART

Research conducted over the past decade has demonstrated the value of isokinetic exercise from the standpoint of rehabilitating injured human joints and associated muscle groups as well as training joints and muscle groups for improvement of human performance. The term "isokinetic" refers to the exercise concept that involves restricting the movement of a portion of the body about a particular anatomical axis of rotation to a rotational velocity. This is achieved by applying an accommodating resistance to the contracting muscle, that is a constantly varying resistive force. This resistive force changes in value throughout the range of motion of the limb in a manner which mimics the varying amount of force that the associated muscle group is able to generate at various points throughout the contraction.

The observation that the amount of force which a muscle group generates varies throughout the range of motion of the associated joint may be explained in terms of anatomical axis of rotation (i.e., a variable biological lever length advantage), enzymatic profile (i.e., intracellular contractile and metabolic protein composition), musculo-tendinous length tension relation and ballistic considerations. An example of this phenomenon can be shown in the knee joint extension during which the quadriceps muscle is seen to develop peak torque at about the midrange of rotation.

Conventional methods of "free weights" exercise require the muscle to act against a load which cannot be greater than the least torque developed at the weakest point in the range of motion of the joint. Thus, with free weights the muscle operates at a reasonable work load in only a small portion of the overall range of motion and does not experience optimal loading during the stronger points in the range of motion.

Semi-accommodating resistance exercise such as is provided in some cam-based exercise systems, wherein the load on the muscle is biased and semi-variable, are at best approximations to the variations in force generated by the particular muscle groups sampled from a cross-section of individuals. This approximation of variable force generation, which may be visualized as a quasi-bell shaped curve of force plotted against degrees of range of motion, is used to shape a cam to control application of the resistive force in a semi-accommodating, semi-variable manner.

Isokinetic exercise systems, on the other hand, provide completely accommodating resistance which offers a variable force opposing muscle contraction in a manner which imitates the variable force generated by the involved muscle group. In this type of system, the rotational velocity of the lever arm to which the human limb is attached is constrained to a maximum permitted value and any force exerted by the limb which tends to accelerate the lever arm beyond that maximum value is matched with an accommodating resistance. Accordingly, the muscle group involved may operate at its optimal tension development throughout the entire range of motion. The net rehabilitation benefit or the net gain in human performance in this training modality is substantially greater than that achieved with conventional exercise modes.

The greater benefits of isokinetic exercise can also be explained in terms of the effect on the recruitment pattern of specific muscle fiber types. It has been established that skeletal muscle is an admixture of at least two distinct cell types. One type of cell is relatively large and rich in anaerobic enzymes which have the capacity to carry on the cell's metabolic needs without oxygen. The other cells are smaller and rich in aerobic components which rely on the presence of oxygen to supply the cell's metabolic requirements. Research has shown that, at large loads and low speeds of contraction, the muscle cell type primarily involved in the exercise is the anaerobic, large diameter cell. Conversely, at low loads and high speed of contraction, the aerobic, smaller diameter cells are primarily involved.

A rehabilitation program which imposes a work load on the muscle groups at either of the extremes of load and velocity will be neurally recruiting one particular muscle cell type. Therefore, it is essential that the muscle be exercised at the center of the force-velocity curve for maximum rehabilitation benefit. This can best be achieved with isokinetic exercise and specific speed selection for the constant contractile velocity of the involved muscle group.

Isokinetic exercise systems of the prior art (for example, the system shown in Perrine U.S. Pat. No. 3,465,592) involve a fixed length lever arm which is attempted to be adjusted accurately to the length of the limb being exercised by aligning as closely as possible the anatomical axis of rotation with the fixed machine axis of rotation. However, this alignment can only be approximated prior to the onset of exercise and hence the rotational velocity of the limb will differ from the rotational velocity of the lever arm. Moreover, a further complicating factor is that the axis of rotation of a human joint is dynamic and shifts during the exercise motion. This i true of the knee joint and is especially pronounced in the shoulder joint. Even if the position of the involved joint is mechanically constrained, the anatomical axis of rotation will shift during the exercise motion. A result, the constraining of the fixed length lever arm to a maximum permitted angular velocity means that the angular velocity of the involved limb about the anatomical axis of rotation will vary.

An additional disadvantage of the fixed length lever arm systems of the prior art is that substantial joint compression is introduced by constraining the human limb to a fixed path of rotation at the point of attachment to the lever arm. This joint compression produces an uncomfortable level of pain in certain individuals with joint problems. More seriously, the magnitude of joint compression produced in prior art systems precludes early initiation of rehabilitative exercise in patients which have undergone surgery on the involved joint.

A further disadvantage of the fixed length lever arm systems of the prior art is that the ability to isolate muscle groups involved in extension and flexion is substantially reduced and it is observed that substantial motion of other portions of the body are involved during the exercise motion. This motion of other portions of the body brings into play work activity by the associated muscle group and makes it impossible to isolate the work performed by the muscle groups directly involved in the exercise motion of interest or makes it such that the different muscle groups producing flexion and extension are not actually isolated during respective portions of the exercise motion. The unnatural feeling of the exercise motion is a deterrent to patient interest and willingness to follow the exercise regimen over the period of rehabilitation.

SUMMARY OF THE INVENTION

1. Objects of the Invention

Accordingly, it is the principal object of this invention to provide an improved exercise and diagnostic system and method.

It is another object of this invention to provide an isokinetic exercise system and method which enables closer achievement of true isokinetic joint rotation velocity.

It is another object of this invention to provide an exercise system and method which substantially reduces joint compression and provides improved muscle group isolation during the exercise motion.

It is another object of this invention to provide an exercise system and method which is easier to set up and operate and provides more accurate diagnostic information.

It is another object of this invention to provide an exercise and diagnostic system which achieves self-calibration and self-correction based on continuous monitoring of the accuracy of the velocity control function.

It is another object of this invention to provide an improved system and method for computing a velocity demand signal for control of a rotational velocity governing system in a passive resistance exercise system.

It is another object of this invention to provide a passive resistance exercise system based on a hydraulic actuator and flow control valve which achieves more effective, accurate and stable control over the speed governing operation of these components.

It is another object of this invention to provide a real time control system for a passive resistance exercise system which continuously tracks and stores system control error information and provides self-correction of control signal values based on said stored information.

2. Features and Advantages of This Invention a. The System Features

(1) Radially Floating Body to Lever Arm Mounting

One aspect of this invention features a muscle exercise and diagnostic system which includes a shaft defining a fixed axis of rotation, a lever arm, and an arm coupling arrangement for coupling the lever arm to the shaft for rotation about the fixed axis. In addition, a body coupling arrangement is provided for coupling a selected portion of the human body to the lever arm for rotation with the lever arm about an anatomical axis of rotation associated with the body portion. One of the arm coupling means and the body coupling means is arranged to establish a fixed tangential mounting relation and a sliding radial mounting relation between the lever arm and the associated element coupled thereto so that the distance between the body coupling means and the fixed axis of rotation may freely change during an exercise motion. A velocity control arrangement is operatively associated with the shaft means for limiting the maximum permitted rotational velocity of the arm to a value predetermined in accordance with a preselected velocity control function.

This feature of the invention provides the advantage of a natural exercise motion in which the anatomical axis of rotation can shift with respect to the mechanical axis of rotation in a substantially unconstrained manner. This reduces joint compression in the joint involved in the exercise motion and thus increase the comfort of the patient during the exercise regimen. A specific example of the benefits of this mounting arrangement in one patient case history is discussed below.

The system of this invention may use an arm coupling arrangement which comprises a connecting arrangement fixedly connecting the lever arm to the shaft at a predefined point on the lever arm, and a body coupling arrangement which establishes a fixed tangential mounting relation and a free radially sliding mounting relation between the selected body portion and the lever arm. Alternatively, the system may use a body coupling arrangement which comprises means fixedly connecting the selected body portion to the lever arm at a predefined point, and an arm coupling arrangement which comprises means establishing a fixed tangential mounting relation and a free radially sliding mounting relation between the lever arm and the shaft. Both of these arrangements, and any others which provide the same radially floating mounting relationship, achieve the advantages described above.

The radially floating attachment feature of this invention may also be described as a combination of a shaft defining a fixed axis of rotation and a coupling arrangement, including a rigid lever arm, for coupling a preselected point on a preselected body portion to the shaft for combined rotation about the fixed axis of rotation and an anatomical axis of rotation associated with the body portion in a plane orthogonal to the fixed axis with a fixed tangential coupling relationship between the preselected point and the shaft and a freely alterable radial coupling relationship between the preselected point and the shaft during the rotation.

(2) Proportioning the Velocity Demand Signal

In a preferred version of the system, an arrangement is provided for registering an initial lever length comprising the distance from the preselected point on the body portion to the anatomical axis of rotation of the body portion when the anatomical axis is substantially aligned with the fixed axis. Another arrangement is provided for continuously registering the distance between the preselected point and the fixed axis during the rotation. Provision is also made for establishing an anatomical velocity demand function. In this version, the velocity control means comprises a rotational velocity governor system responsive to an input velocity control signal to limit the maximum permitted instantaneous rotational velocity of the shaft means; and a velocity control computer system is provided for supplying a velocity control signal to the governor system throughout the rotation as a prearranged functional combination of the anatomical velocity demand function, the registered initial lever length and the registered distance.

(3) Predictive Control Function Using a Rotary Actuator and Torque/Velocity Control of Valve Position Further, in the preferred version of the invention, the governor system comprises a rotary hydraulic actuator with a rotationally mounted shaft extending therethrough and carrying a rotating vane cooperating with a stationary vane on the interior of the actuator provided to define two complementarily variable volumetric chambers on opposite sides of the vanes and having a pair of fluid ports therein each communicating with one of the chambers. The system also includes a fluid control valve comprising at least a pair of fluid ports communicating with the fluid ports of the actuator, an internal valve spool for controlling the effective orifice size of the fluid ports and regulating the flow of fluid therebetween, and valve position drive means responsive to an input valve position control signal to control the position of the value spool. The velocity control computer comprises means registering the value of torque on the shaft and means for computing and supplying to the valve position drive means a predictive value for the valve position control signal as a combined function of the measured torque value in addition to the anatomical velocity demand function, the registered initial lever length and the registered distance between the connecting point and the fixed axis of rotation.

The preferred system further comprises and arrangement for registering the actual angular velocity of the lever arm, and the combined function further incorporates the actual velocity value.

The unique velocity governor system of this invention could also be used generally as a feature in muscle exercise and diagnostic system employing isokinetic or controlled velocity exercise, i.e. in systems which do not incorporate the floating patient attachment feature of the invention. Such a system comprises a lever arm, and arrangement coupling the lever arm to a shaft for rotation with the shaft about a mechanical axis of rotation, and an arrangement for establishing an anatomical velocity demand signal. The rotational velocity governor system is coupled to the shaft for limiting the rotational velocity thereof to a maximum velocity value in accordance with the velocity demand signal. The governor system incorporates the elements and has the functions described above.

(4) Digital Computer Real Time Control

A muscle exercise and diagnostic system in accordance with this invention may be implemented using a velocity control computer which does mostly analog signal computation or one which does mostly digital signal computation. In the latter version the same lever arm, shaft and velocity governor system as described above may be employed. In this version the control arrangement comprises an angle measuring arrangement for measuring the angular position of the lever arm and shaft and producing an analog angle signal corresponding thereto, a velocity measuring means receiving the angle signal for computing the velocity of the lever arm and shaft and producing an analog velocity signal corresponding thereto, and a torque measuring means for measuring the value of torque exerted on the shaft and producing an analog torque signal corresponding thereto.

An analog to digital converter system is provided for digitizing the analog velocity signal and the analog torque signal to corresponding digital velocity and torque signals corresponding thereto. A digital computer system, including program storage arrangements and input/output circuit arrangements receives the digital signals and the velocity demand signal and computes a digital valve position command signal. A digital to analog converter system receives the digital valve position command signal for producing a corresponding analog valve position command signal and supplies the signal to the valve position drive means.

The program storage arrangement includes a baseline correction routine for analyzing the digital angle signals to determine when the lever arm is in a quiescent condition and thereupon computing baseline values of the digital velocity and torque signals from the analog velocity and torque signal. It also includes a baseline correction routine for correcting digital velocity and torque signals based on the computed baseline values thereof. It further includes a velocity demand correction routine for calculating the current system error based on the digital value of measured velocity and the input velocity demand signal and calculating a corrected velocity demand signal as a prearranged function of the calculated system error and the input velocity demand signal. Also provided is a torque computation routine for calculating the absolute value of the digital torque signal and a torque factor routine for calculating a torque factor as a prearranged function of the absolute torque value. A valve position command routine is included for calculating a valve position command as a prearranged function of the corrected velocity demand signal and the torque factor as well as a correction routine for converting the valve position command signal to a corrected valve position command signal based on looking up a corrected value in a stored table of correction values.

(5) Precision Velocity Calibration

In a preferred system the analog to digital converter means also receives the analog angle signal for converting the signal to a digital angle signal and the computer means receives the digital angle signal. In this version the program arrangement further includes a velocity calibration routine for calculating a velocity calibration factor, including a routine for calculating velocity as a function of change in the digital angle signal, a routine for calculating the absolute value of the calculated velocity; a routine for calculating the average value of the digital velocity value, a routine for calculating the absolute value of the average digital velocity value, a routine for calculating a new velocity calibration value as a prearranged function of the prior velocity calibration value, the absolute value of the calculated velocity, the absolute value of the average digital velocity value, and the value of a previously calculated velocity calibration factor; and a routine for calculating a velocity calibration factor as a prearranged function of the new velocity calibration value; and the velocity demand correction routine calculates current system error based on actual digital velocity value modified by the velocity calibration factor. This velocity calibration routine precludes the need for precision resistor and capacitor components in the velocity measuring circuitry which measures velocity in an analog differentiating circuit. It also avoids the need to provide trimming resistors for calibrations purposes, and it gives the advantage of continuous self calibration of the velocity measuring system

(6) Torque and Velocity Baseline Correction

The preferred implementation of a digital computer control version of this invention also uses a program means which includes program arrangements for establishing a velocity/torque correction factor array having a two dimensional relationship to velocity and torque parameters and a velocity/torque correction factor look up routine for looking up a velocity/torque correction factor value in the array based on value of velocity and torque. In addition a routine is provided for updating the value of the velocity/torque correction factor in the array based on the calculated system error. In this preferred version the valve position command routine calculates the valve position command value partially as a function of the velocity/torque correction factor.

This feature provides for automatic calibration and expert system tracking and adjustment of the predictive function calculation of valve position command signal values. It thus provides more accurate control of the behavior of the exercise system under varying conditions of temperature of the hydraulic fluid due to alterations in ambient conditions and/or heating due to the frictional working of the hydraulic fluid which absorbs energy during the exercise regimen.

It is also preferable that this digital system implementation include the lever arm length tracking feature of this invention so that the velocity demand signal can be proportioned by the ratio of the initial lever length and the currently measured lever length.

This gives the advantage of more accurate control of the angular velocity of the limb relative to the anatomical axis of rotation.

b. The Method Features

(1) Radially Floating Attachment

This invention also features a method for controlled resistance exercise which includes the steps of mounting a shaft for rotation about a fixed axis and coupling a preselected point on a human body portion to the shaft through a rigid lever arm for enabling combined rotation of the lever arm about the fixed axis and the human body portion about an anatomic axis in the vicinity of the fixed axis with a coupling relation comprising a fixed tangential relation and a freely alterable radial relation between the preselected point and the shaft during the combined rotation; and limiting the maximum permitted rotational velocity of the shaft to a value predetermined in accordance with a preselected velocity control function.

(2) Proportioned Velocity Demand

A preferred version of the method also comprising the steps of registering an initial lever length comprising the distance from the preselected point on the body portion to the anatomical axis of rotation of the body portion when the anatomical axis is substantially aligned with the fixed axis and registering in at least a substantially continuous manner the distance between the preselected point and the fixed axis during the rotation. It further includes defining an anatomical velocity demand function; and limiting the instantaneous maximum permitted rotational velocity of the shaft means to a value which is determined in accordance with a a prearranged functional combination of the anatomical velocity demand function, the registered initial lever length and the registered distance.

(3) Limits on Range of Motion

The method may optionally and preferably include a range of motion limiting feature implemented in the steps of registering at least one limit value on the angular position of the lever arm and the body portion; registering in at least a substantially continuous manner the actual angular position of the lever arm during the rotation thereof; and calculating and registering in at least a substantially continuous manner the difference between the registered limit value and the registered actual angular position. In this version the step of limiting the rotational velocity comprises limiting the instantaneous maximum permitted rotational velocity of the shaft means to a value which is determined in accordance with a prearranged functional combination of the anatomical velocity demand function, the registered initial lever arm length, the registered distance, and the registered difference.

(4) Control of Rotary Actuator and Valve with Velocity/Torque Predictive Function This invention also features a method for controlling the maximum permitted shaft velocity of a velocity governing system comprising a rotary hydraulic actuator with a rotationally mounted shaft having a rotating vane carried thereon and cooperating with a stationary vane on the interior of the actuator to define two complementarily variable volumetric chambers on opposite sides of the vanes, and a pair of fluid ports each communicating with one of the chambers; a fluid control valve comprising at least a pair of fluid ports communicating with the fluid ports of the actuator, an internal valve spool for controlling the effective orifice size of the fluid ports and regulating the flow of fluid therebetween, and valve position drive means responsive to an input valve position control signal to control the position of the value spool.

This method includes the steps of establishing a shaft velocity demand signal; measuring the actual torque on the shaft of the actuator; and calculating a valve position command signal based on a predetermined functional combination of the velocity demand signal and the measured actual torque.

(a) Velocity/Torque Correction Factor Array

In a preferred version the following steps are also included:

measuring and registering the instantaneous value of actual shaft velocity;

calculating a current system error signal based on a predetermined functional combination of the measured actual shaft velocity and the shaft velocity demand signal;

correcting the shaft velocity demand signal as a function of the calculated current system error; establishing a two dimensional array of correction signal data points, each data point corresponding to prearranged ranges of values of the shaft velocity demand signal and the measured actual torque signal and storing a velocity/torque correction signal value;

addressing an active one of the data points based on the current measured torque value and the current value of the shaft velocity demand signal;

reading the stored velocity/torque correction signal value stored at the active data point; and storing at the active data point a new velocity/torque correction signal value as a prearranged functional combination of the correction signal value read and the value of the current system error. In this method, the step of calculating a valve position command signal is performed on the basis of a predetermined functional combination of the shaft velocity demand signal, the measured torque signal and the read velocity/torque correction signal value.

(5) Exercise Method Using Rotary Actuator and Control Valve Controlled with Velocity/Torque Predictive Function This invention also features a method for controlled accommodating resistance exercise which begins with the steps of mounting a shaft for rotation about a fixed axis; and coupling a preselected point on a human body portion to the shaft through a rigid lever arm for enabling combined rotation of the lever arm about the fixed axis and the human body portion about an anatomic axis in the vicinity of the fixed axis with a coupling relation comprising a fixed tangential relation and a freely alterable radial relation between the preselected point and the shaft during the combined rotation.

Other steps included in the method are registering an initial lever length comprising the distance from the preselected point on the body portion to the anatomical axis of rotation of the body portion when the anatomical axis is substantially aligned with the fixed axis; registering in at least a substantially continuous manner the distance between the preselected point and the fixed axis during the rotation; and defining an anatomical velocity demand function.

The final step is to limit the instantaneous maximum permitted rotational velocity of the shaft means to a value which is determined in accordance with a prearranged functional combination of the anatomical velocity demand function, the registered initial lever length and the registered distance using a velocity governing system comprising a rotary hydraulic actuator with a rotationally mounted shaft having a rotating vane carried thereon and cooperating with a stationary vane on the interior of the actuator to define two complementarily variable volumetric chambers on opposite sides of the vanes, and a pair of fluid ports each communicating with one of the chambers; a fluid control valve comprising at least a pair of fluid ports communicating with the fluid ports of the actuator, an internal valve spool for controlling the effective orifice size of the fluid ports and regulating the flow of fluid therebetween, and valve position drive means responsive to an input valve position control signal to control the position of the value spool.

This final step includes the steps of measuring the actual torque on the shaft of the actuator; and calculating a valve position command signal based on a predetermined functional combination of the anatomical velocity demand function, the registered initial lever length, the registered distance and the measured actual torque.

This method may further include the velocity calibration method steps described above and the velocity/torque correction factor method steps described above to improve the overall accuracy of the exercise control method. It may also include baseline correction steps for the velocity and torque measurements.

Overall the system and method of this invention improves the manufacturability of exercise systems of the accommodating resistance type. The calibration steps required are reduced or substantially eliminated and the long term stability of the performance of the system is improved. The digital control system and method achieves levels of control and stability that are not achievable in other control schemes together with flexibility in the velocity control function due to the ability to alter the control program in the system.

Other objects, features and advantages of this invention will be apparent from a consideration of the detailed description of various embodiments set forth below in conjunction with the accompanying drawings.

BRIEF DESCRIPTION OF DRAWING FIGURES

FIG. 3 is a partly sectioned elevational view of a lever arm assembly incorporating features of this invention.

FIG. 4 is a partial section view taken along the lines 4—4 in FIG. 3.

FIG. 5 is a elevational view of an alternate version of a lever arm incorporating features of this invention.

FIG. 13–16 are circuit diagrams of an analog computer system implementation of an exercise system in accordance with this invention.

FIGS. 19 and 20 are diagrams of the electrical system components of a digital computer system implementation of the exercise system of this invention.

FIG. 21 is a diagram illustrating the organization of software routines utilized in a programmed digital computer embodiment of this invention.

FIG. 22 is a diagram illustrating the execution sequence of program routines in a digital computer control version of the exercise system of this invention.

FIGS. 25A and 25B illustrate operational features of a programmed digital computer implementation of the system of this invention.

FIG. 26 is a three-dimensional graph illustrating a control function feature of the general system of this invention.

FIGS. 30–33 are mechanical drawings illustrating the preferred features of a hydraulic actuator and flow control valve implementation of a rotational velocity governor system in accordance with this invention.

DETAILED DESCRIPTION OF EMBODIMENTS OF THE INVENTION

1. Incorporation of the Invention in an Isokinetic Station

Figure 1:
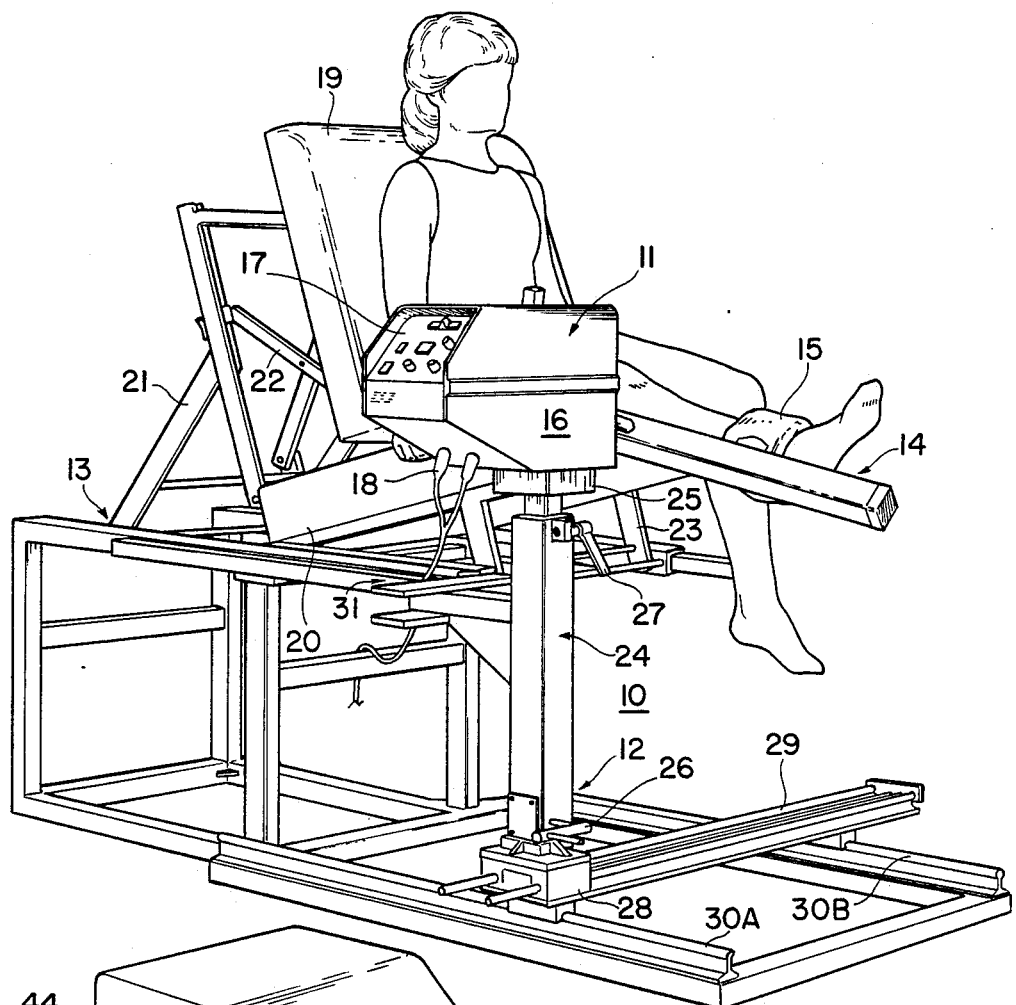
FIG. 1 is an isometric drawing of an isokinetic station incorporating an exercise system in accordance with this invention which is capable of implementing the exercise control method of this invention.

The system and method of this invention is preferably incorporated into a overall isokinetic station which has been designed for maximum utility in patient positioning, optimum flexibility in set up for exercise of various portions of the human body, and minimum involved floor space. Referring to FIG. 1, isokinetic station 10 includes a passive exercise resistance system 11, a mounting arrangement 12 and a patient couch 13. The passive resistance system 11 includes a lever arm assembly 14, a patient attachment cuff 15, a housing 16 which contains the passive resistance component of the system along with electronic controls. The housing 16 further includes a control panel 17 and output leads 18 which feed measurement signal outputs to a chart recorder and/or to a computer data acquisition unit. The details of this passive exercise resistance control system will be given below in connection with other drawing figures.

The patient couch arrangement 13 includes two cushion portions 19 and 20 which, together with various positioning elements, provide for positioning of a patient in a sitting or reclining orientation, which is selected depending on the patient limb being exercised. In the set-up shown in FIG. 1, the cushion portion 19 is serving as a backrest and the cushion portion 20 is serving as a seat. A pair of positioning members 21 controls the angular orientation of the cushion portion 19 and a scissors jack type of positioning arrangement 22 controls the forward and backward position of the cushion portion 19.

Positioning supports 23 control the angle of the cushion element 20. To put the patient in a reclining position, the positioning members 23 and 21 are reoriented so that the cushion elements 19 and 20 are horizontal and in line with each other.

The mounting and positioning system 12 includes a vertical pedestal arrangement 24 which includes a rotary support member 25 to which the housing of the passive resistance system 16 is attached. Preferably a detent arrangement is provided such that the angular orientation of the housing 16 relative to the patient couch can be selectively altered to fixed angles. A height adjustment jacking arrangement operated by the jack handle 26 is provided within the pedestal 24 to raise and lower the housing 16 for positioning of the axis of rotation of the lever arm assembly 14 relative to the patient.

The pedestal assembly 24 is mounted on a bearing slide arrangement 28 which permits side-to-side movement of the pedestal assembly 24 relative to the patient couch. Another bearing and track arrangement 30A and 30B permits front-to-back movement of the pedestal 24 carried on the bearing and track arrangement 28 and 29. A stabilizing arrangement 31 is provided to rigidly fix the pedestal 24 in a particular selected position relative to the patient couch assembly 13.

Figure 2:
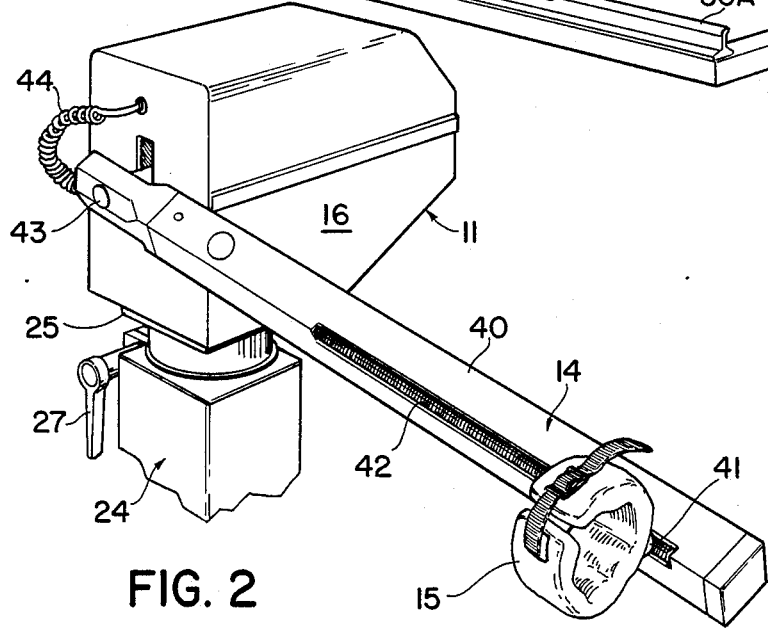
FIG. 2 is an isometric drawing of mechanical portions of the exercise system of this invention.

FIGS. 2-4 illustrate in more detail one embodiment of a lever arm assembly 14 having a patient attachment cuff 15 which is mounted to the lever arm assembly in a manner such that the patient attachment point is free to move radially during an exercise motion. This is provided by the sliding mounting relation between the lever arm assembly 14 and the patient attachment member. In the particular embodiment shown in FIGS. 2-4, the lever arm assembly 14 comprises a hollow square tube 40 having an elongated slot 42 in one corner thereof. An attachment post 41 extends through the slot 42 and, as shown in FIG. 3, is carried on a bearing assembly 50 which traverses the interior of the hollow square tubing 40. At one end of the hollow square tubing 40, a solid end member 56 is attached. This end member 56 includes an aperture 60 therethrough which permits the lever arm assembly 14 to be mounted on a shaft 43 as shown in FIG. 2. Shaft 43 extends into the housing 16 and, in a preferred embodiment, this shaft is part of a hydraulic rotary actuator which provides the resistive component of the exercise system. A cable 44 connects the potentiometer arrangement 51 shown in FIG. 3 to the electronic control circuitry which is provided within the housing 16.

The potentiometer arrangement 51 includes a rotary potentiometer 52 which is coupled to a pulley and belt arrangement involving a pulley 53 on one end of the lever arm assembly 14, a second pulley arrangement 54 mounted on the other end of the lever arm assembly 14 and a belt 55, which is carried on the two pulleys and is driven by fixed connection to the carriage assembly 50 which traverses the interior of the lever arm assembly. Accordingly, as the carriage assembly 50 translates back and forth within the lever arm assembly, the rotary potentiometer 52 is driven to provide a position signal for the electronic circuitry which will be discussed in more detail below. This position signal corresponds to the current lever arm length, i.e. the distance from the center of the shaft to the point of patient attachment which will change during an exercise motion.

The particular arrangement of the lever arm assembly 14 depicted in FIGS. 1 and 2 involves an ankle cuff arrangement 15 attached to the lever arm assembly 14. In a complete system, various types of lever arm assemblies 14 would be provided for exercising different portions of the human body and different patient attachment devices would be provided for mounting to the carriage assembly of the lever arm assembly 40 in order to provide an appropriate type of interface to the portion of the patient's body to be exercised.

FIG. 5 illustrates another embodiment of a lever arm assembly which utilizes a bearing and track arrangement 72 having a bearing block 71 riding on a pair of tracks 73A and 73B. A potentiometer and pulley arrangement 71 is fastened to the tracks 73 at one end and a second pulley arrangement 75 is provided on the opposite end of the lever arm assembly 70. A continuous belt 76 is attached to the bearing block 71 to drive the potentiometer arrangement as the bearing block 71 translates on the tracks 73. A similar coupling element would be provided for coupling the bearing block 71 to a patient attachment device. The aperture 74 would mount on the actuator shaft in the same manner as the corresponding mounting aperture of the lever arm assembly 14.

2. The Passive Resistance System and Method of This Invention

In accordance with various embodiments of this invention, the passive resistance system 11 shown in FIG. 1 may utilize a control system arrangement which uses mainly analog signal processing or one which uses mainly digital signal processing. However, as will be seen in the detailed description given below, the control system arrangement involving basically analog signal processing also advantageously includes some digital signal processing features for effective implementation of the control functions. In addition, the embodiment of this invention involving mostly digital signal processing also incorporates some analog signal processing for convenience of implementing the overall velocity control function. For purposes of convenience of discussion, the first-mentioned form of control system will be called an analog computer control embodiment and the second form of control system will be termed a digital computer control embodiment.

3. Basic System Concepts of the Invention

Figure 6:
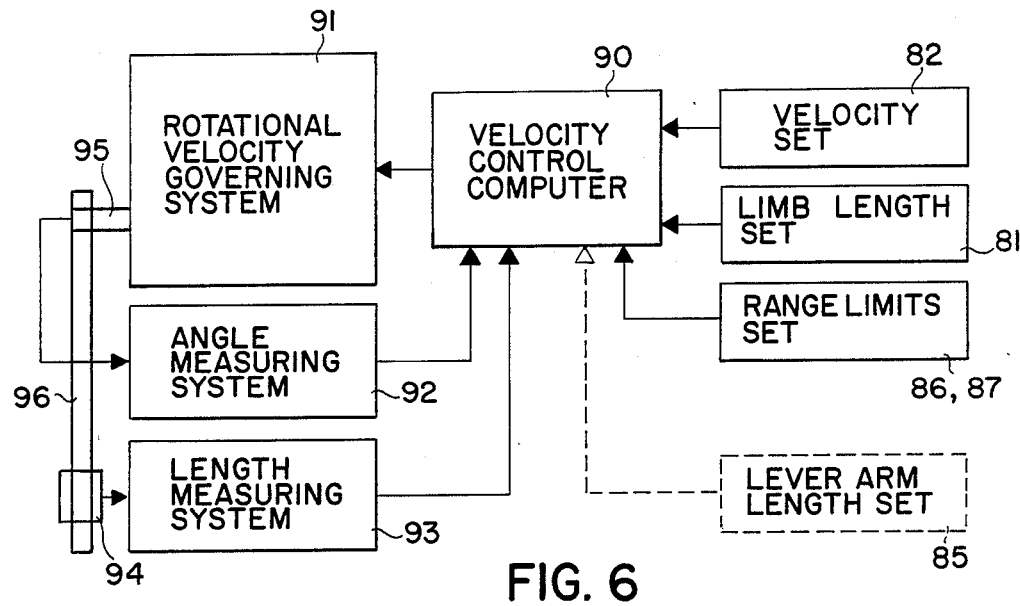
FIG. 6 is a general system block diagram illustrating the elements of an exercise system in accordance with this invention.

FIG. 6 shows in schematic block diagram form the elements of a muscle exercise and diagnostic system in accordance with this invention. Lever arm assembly 96 includes a lever arm which is mounted on a shaft 95 for rotation about the axis of the shaft. The shaft 95 is fixed in space by a stand or support arrangement such as is shown in FIG. 1. Connecting arrangement 94 provides means for connecting a portion of the human body to lever arm 96 using a convenient connection attachment such as the ankle cuff shown in FIG. 1. Other forms of attachment can be provided for other limbs and body parts. Connection arrangement 94 is mounted to lever arm 96 utilizing a mounting arrangement which provides a sliding radial mounting relation, but a fixed tangential mounting relation as discussed above.

A length measuring system 93 is operatively associated with the translating limb attachment arrangement 94 to continuously monitor the distance from the point of attachment of the human body to the axis of the shaft 95 during the exercise motion. This length measuring system may comprise a potentiometer operatively connected to the attachment arrangement 94 to register the length as a proportional resistance as discussed above. The output signal from the length measuring system 93 is coupled into a velocity control computer 90 whose function will be described below.

An angle measuring system 92 is appropriately coupled to shaft 95 via some mechanical linkage to continuously monitor the angle of the lever arm 96. This function can be readily performed by a rotary potentiometer attached to the shaft 95. The output signal from the angle measuring system is also coupled into the velocity control computer 90.

Velocity control computer 90 also receives a limb length input signal from a limb length set control 81, a velocity set input signal from a velocity set control 82, and range limits signals from a range limits setting control 86, 87. The lever arm length set signal from setting control 83 could be used in an optional embodiment when lever length is not continually tracked. All of the lever length and limb length parameters could be deleted in a system which assumes alignment of mechanical and anatomical axes.

Velocity control computer 90 utilizes all of the active input signals to produce an output velocity control signal for controlling a rotational velocity governor system 91 and thereby establishing a maximum permitted angular velocity of the lever arm 96. As will be discussed later, there are a number of simple and complex functions which may be utilized by the velocity control computer 90 in determining the velocity control signal.

The essential function of the velocity control computer is to utilize the lever arm length signal and the limb length set signal to adjust the velocity control signal to compensate for differences between the lever arm length and the limb length, that is, differences due to permitted misalignment of the fixed axis of rotation of lever arm 96 and the anatomical axis of rotation of the limb or other body part attached to the lever arm. The continuous monitoring of the lever arm length enables the velocity control computer to continuously adjust the velocity control signal as the lever arm length changes during the exercise motion due to dynamic changes in the position of the anatomical axis of rotation.

It can be shown that, in the case where an isokinetic velocity of rotation of the human limb about the anatomical axis is desired, the velocity control computer 90 may ratio the monitored lever arm length signal L1 with the measured limb length signal L2 and multiply the ratio by the velocity set value to obtain a velocity control signal which will provide a maximum permitted angular velocity of the lever arm which correspondingly produces a maximum permitted angular velocity of the limb which is closely approximated to the velocity set value. Other factors enter into the velocity correction function, but they are secondary factors, such as translational velocity of the attachment during the exercise motion, which are small and can be ignored.

It will be appreciated that, as the exercise motion progresses and the anatomical axis shifts, the lever arm distance will change and the velocity control computer will compensate by changing the maximum permitted lever arm velocity to keep the maximum human limb velocity more constant. This contrasts with the fixed path lever arm systems of the prior art in which the lever arm rotational velocity is maintained at a fixed maximum permitted value so the rotational velocity of the human limb is necessarily changing during the exercise motion.

The velocity control computer 90 preferably utilizes the angle input as part of a servo control loop to maintain good regulation on the velocity control signal. It may also use the angle input signal together with the range limits signals to control the permitted range of motion of the lever arm. The manner of accomplishment of this function depends on the type of velocity control computer utilized in the system. In an analog computer version, a signal indicating the direction of the motion of the arm may be required and this can be derived in one of the embodiments of the invention described below from a torque signal which has different polarity for different directions of motion. It should be understood that, since this invention utilizes computer circuitry to derive the velocity control signal, other anatomical velocity functions than the isokinetic function could be programmed into the system. For example, the maximum permitted anatomical velocity function could be a sine wave or have some other arbitrary shape of permitted velocity versus angle over the range of exercise motion.

The rotational velocity governor system 91 may comprise a number of different hydraulic, motor and gear train, and motor and clutch arrangements which permit electrical control of the permitted maximum rotational velocity of the lever arm 96. A preferred form of hydraulic actuator and proportional control valve arrangement for accomplishing this function in accordance with this invention is described below.

a. Basic Concept of Radially Floating Patient to Shaft Coupling

Figure 7:
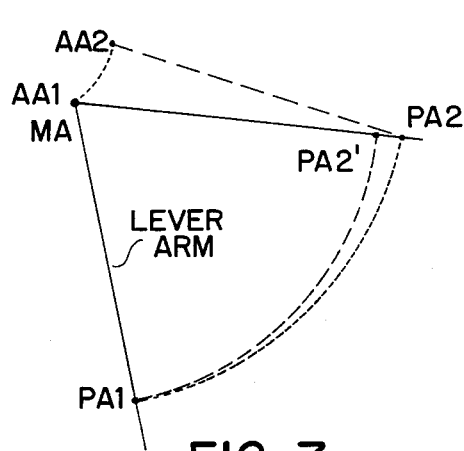
FIGS. 7 and 8 are schematic diagrams useful in explaining the improved functional performance of an exercise system in accordance with this invention.
Figure 8:
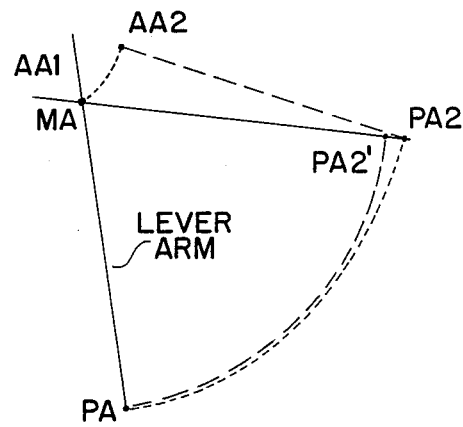

FIGS. 7 and 8 together with FIG. 6 illustrate the basic concepts of the system of this invention. In an exercise system in accordance with this invention a shaft means defines a fixed axis of rotation which is designated in FIGS. 7 and 8 "MA" for mechanical axis. A coupling means which includes a rigid lever arm couples a preselected point on a preselected body portion to the shaft for combined rotation about the fixed axis of rotation MA and an anatomical axis of rotation AA associated with the body portion in a plane orthogonal to the fixed axis. This coupling means provides a fixed tangential coupling relationship between the preselected point of attachment PA and the shaft and a freely alterable radial coupling relation between the preselected point PA and the shaft represented by MA during the rotation.

The velocity control means coupled to the shaft means limits the maximum permitted rotational velocity of the shaft to a predetermined value according to a preselected velocity control function. As shown in FIG. 7, the point of attachment PA of the preselected point on the body to the lever arm is permitted to vary radially during rotation of the lever arm so that instead of describing a fixed arc between points PA1 and PA2′, the point of attachment moves radially relative to the mechanical axis MA of the shaft during the exercise motion. Accordingly the point PA traverses the path of PA1-PA2 as shown in FIG. 7. The reason for this shift in the radial orientation between the point of attachment and the mechanical axis MA is the shift in the anatomical axis during the exercise motion as represented by the endpoints AA1 and AA2. The overall degree of shifting in the anatomic axis relative to the mechanical axis MA is somewhat exaggerated in FIG. 7 for certain exercise motions, but this exaggeration is used to more clearly illustrate the principles of the invention.

It can be readily seen from the diagram in FIG. 7, that permitting the point of attachment to move radially on the lever arm during the rotation produced by the exercise motion provides a comfortable adjustment of the point of attachment to the lever arm as the anatomic axis shifts. Without this radially free movement, substantial and painful joint compression can result as the anatomic axis tries to shift while the fixed attachment constrains the exercise path to a circular arc about the mechanical axis. Programs of investigation utilizing exercise systems in accordance with this invention have demonstrated the value of the free radial floating attachment point concept of this invention in reducing joint compression and patient discomfort during rehabilitative exercise.

b. Case History of Patient Benefits

As an example, consider the case of a patient who is a thirty-four year old male aircraft mechanic with a diagnosis of a torn anterior cruciat and probable lateral meniscal tear referred to the physical therapy department of a clinic. The patient was athletic and in good health with a long history of active involvement in sports. Physical therapy treatment was provided for a period of eight weeks to strengthen the musculature in an effort to provide adequate functional stability. Good results were obtained with the program but continued problems led to a decision to recommend the surgical reconstruction which was later performed. In general, initial progress following surgical reconstruction was excellent. Range of motion of the joint was taken to full limits, in a passive sense, during the first eight weeks after the operation. A program stressing hamstring and hip rehabilitation was initiated early using isokinetic exercise equipment of the prior art involving a fixed attachment of the ankle relative to the mechanical axis of rotation of the system.

Although the patient denied significant pain during the course of the rehabilitation program, progress into the resistive phases of the exercise regimen produced chronic swelling of moderate proportions about the knee area. This problem was not alleviated by anti-inflammatory medications, reductions and modifications in the exercise schedule, and the like.

A renewed, vigorous exercise program on prior art equipment and virtually full range of motion of the involved joint produced severe swelling and joint ache and tenderness for approximately twenty-four hours following each exercise session.

The patient was then switched to an exercise program on the system of this invention. The patient immediately reported a reduced sense of joint stress and during the initial two weeks of exercise decreased achiness of the knee was apparent during the twenty-four hour period following exercise. This was accompanied by reduction in the swelling about the knee. After four weeks of an exercise program on the system of this invention, the patient experienced only trace swelling of the knee and no post-exercise discomfort. The patient returned to work as an aircraft mechanic with virtually no difficulty in performing daily tasks. The success of this patient on the system of this invention resulted in his refusal to work out on the prior art equipment and instead the patient elected to wait his turn for use of the system of this invention rather than risk the discomfort and swelling produced by the prior art system.

In the diagram of FIG. 7, the relative shift in the relationship of the point of attachment to the mechanical axis is accomplished by allowing the point of attachment to move radially on a lever arm which has one end in fixed position relative to the mechanical axis. FIG. 8 illustrates that this same principle of relative free radial movement of the point of attachment to the patient relative to the mechanical axis can be achieved in a system in which the point of attachment is fixed in a position on the lever arm but the point of attachment of the other end of the lever arm to the mechanical axis is allowed to shift radially during the exercise motion.

Referring back to the lever arm embodiment shown in FIG. 5, it should be apparent that the bearing block and track arrangement depicted therein could be adapted such that the bearing block 71 is mounted to the shaft of the rotary actuator arrangement or other accommodating resistance control mechanism with the patient being attached to a fixed point relative to the two tracks 73A and 73B. During the exercise motion, the bearing block would turn with the shaft and the tracks could move radially relative to the shaft in the bearing block to adjust the radial position and to permit freely alterable radial coupling relation between the point of patient attachment and the shaft. The same type of potentiometer and tracking pulley and belt arrangement could be utilized to track the effective lever arm length during the exercise motion.

4. The Analog Computer Control Circuit Embodiment a. Control Panel

FIG. 6 illustrates a form of control panel for an analog computer control system embodiment of this invention. A power switch 80 is provided for controlling application of electrical power to the control unit. A limb length pushbutton 81 is provided for registering the initial lever length or neutral limb length at a time when the anatomic axis of rotation of the human limb or other body portion being exercised is substantially aligned with the axis of rotation of the lever arm assembly 14 which is the center axis of the shaft 43 on which the lever arm assembly 14 is mounted. As will be discussed below, the limb length pushbutton 81 controls storage of a digital signal value corresponding to the currently registered limb length as signalled by the rotary potentiometer 52 in the lever arm assembly 14.

Velocity set control 82 comprises a multiple thumbwheel potentiometer control arrangement for setting an electrical resistance value corresponding to the desired maximum angular velocity of the lever arm. A two-position switch 83 is provided to indicate whether the passive resistance system is positioned relative to the left side or the right side of the patient. The indicator lights 84 and 85 indicate the setting of the switch 83. Potentiometer control settings 86 and 87 are utilized to set the upper and lower limits of range of motion of the lever arm assembly during the exercise motion. To set these limits, the lever arm assembly 14 is placed in the desired upper or lower limit position and the corresponding potentiometer dial is rotated until a tone indicates that a resistance setting corresponding to that limit position has been achieved. The integration of these control settings into the overall electronic control system of this invention will be more clear from the description given below of a specific embodiment of the circuit components of the control system.

b. General Concepts

Figure 10:
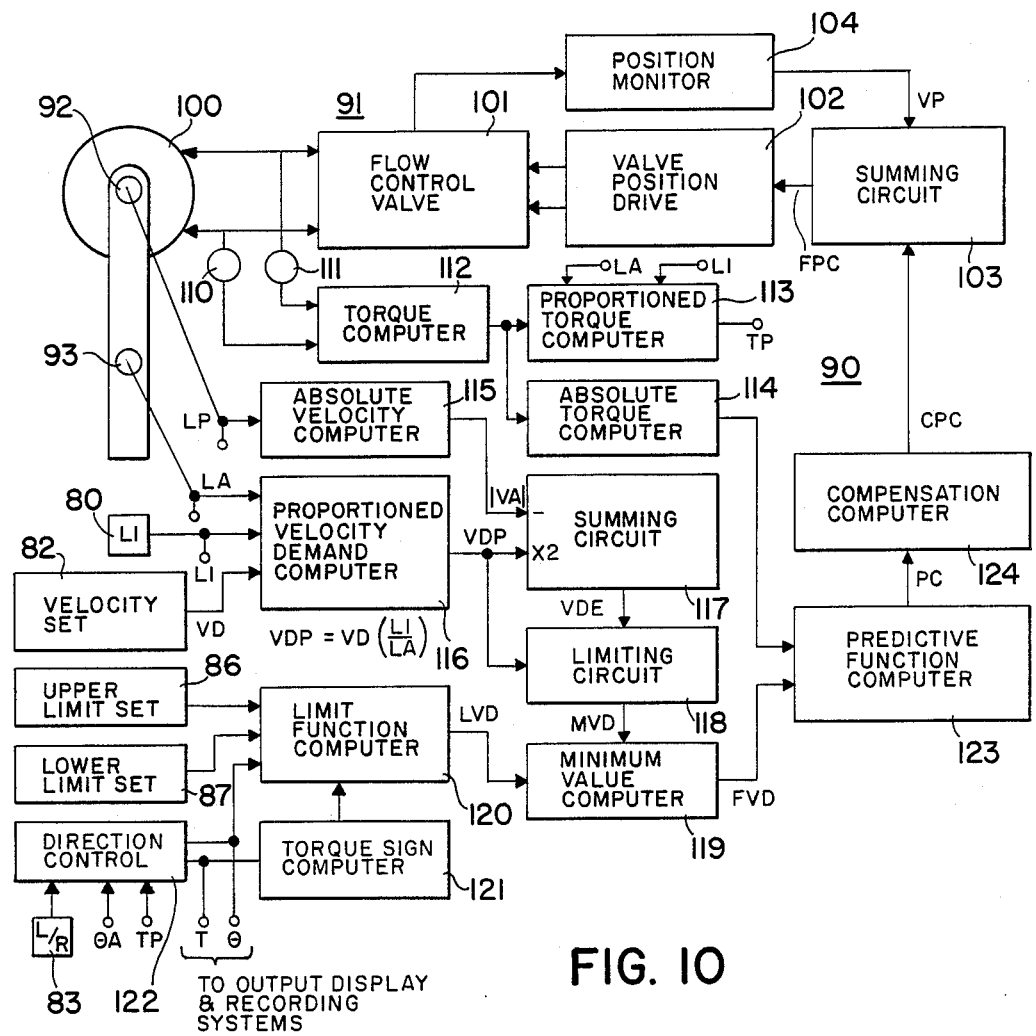
FIG. 10 is a block schematic diagram of an analog computer circuit implementation of the exercise system of this invention.

FIG. 10 illustrates in block diagram form the functional components of a basically analog computer control system in accordance with one embodiment of this invention. The embodiment shown in FIG. 10 constitutes an improvement over the analog computer control system and method depicted in the co-pending parent application referenced above in several respects. The overall hydraulic actuator and flow control valve system is substantially simplified in that the need for a bidirectional flow controller is eliminated. The hydraulic circuitry, which will be described in more detail below, can comprise the combination of a hydraulic actuator and a dual solenoid flow control valve.

This simplification is achieved because the control circuitry of this embodiment involves computing a predictive function for the appropriate valve position based on a turbulent flow mathematical model of the hydraulic flow through the orifices of the flow control system. By utilizing a predictive function arrangement which takes into account the absolute value of the torque experience by the actuator along with the proportioned velocity demand signal provides accurate control of valve position without the compensating function provided by the bidirectional flow controller in the parent application embodiment. In other respects the rotational velocity governing system 91 is the same as that utilized in the parent application embodiment.

A valve position drive 102 controls the position of the flow control valve 101, in this case by driving two solenoids in a push/push relation to the valve spool in the flow control valve. This will be described in more detail below. A position monitor arrangement 104 is used to monitor the position of the flow control valve spool and the output position signal is fed back to an error circuit 103 to provide an inner servo loop which minimizes overshoot and other troublesome operational characteristics of the solenoid flow control valve.

The velocity control computer arrangement 90 includes a torque computer 112 which computes a torque value based on the relative output signals from pressure transducers 111 and 110 coupled into the flow lines between the flow control valve 101 and the hydraulic actuator 100. This computation is basically an analog difference computation. A proportioned torque computer receives the initial lever arm length input signal L1 and the dynamically varying actual lever length signal LA developed from the potentiometer 93 or other length tracking arrangement associated with the lever arm arrangement. The proportioned torque computer 113 provides a proportioned torque signal TP which is fed through a direction control arrangement 122 to provide a direction compensated torque output T to an output display or recording system.

An absolute torque computer 114 takes the output value of the torque computer and computes its absolute value to be fed to the predictive function computer 123. The other input to the predictive function computer is a demand velocity signal whose value may be an arithmetic combination of the measured absolute velocity and a proportion velocity demand signal or it may have a value related to the output of a limit function computer which, in effect, overrides the velocity demand signal which is effective during most of the exercise motion when either an upper or lower limit set into the system is being approached. This limit function control is an optional aspect or feature of the invention. During at least the main portion of the exercise motion, absolute velocity computer 115 takes the angle input from the angle sensing means 92 and computes the absolute angular velocity of the lever arm as the absolute rate of change of the measured angle. This absolute velocity value is fed as a minus input to summing circuit 117.

A proportioned velocity demand computer 116 receives a velocity demand signal input from the velocity set control 82 and an initial length input LI from the limb length set control 80 as well as the actual lever arm length signal LA from the length tracking mechanism 93 on the lever arm itself. The proportioned velocity demand computer computes a proportioned velocity demand signal VDP corresponding to the value of the velocity demand signal VD times the ratio of the limb length signal LI to the actual lever arm length signal LA. This output signal from the proportioned velocity demand computer is fed to the times two input of summing circuit 117. Accordingly, the output of summing circuit 117 is a velocity demand signal adjusted for the current error condition, if any, involving the difference between the proportioned velocity demand signal VDP and the absolute velocity signal. This is part of the outer servo control loop which produces a final velocity demand signal which takes into account the error in the instantaneous actual velocity of the system.

The limiting circuit 118 receives the proportioned velocity demand output signal and limits the final velocity demand signal from the summing circuit 117 to be within a certain range of the proportioned velocity demand signal VDP from the proportioned velocity demand signal computer 116. This is done to minimize the error component present in the final signal. It will be appreciated that when the proportioned velocity demand signal is present but the lever arm is not actually moving, the final velocity demand signal from the summing circuit 117 would be twice the proportioned velocity demand. Since this is not a real error condition, it is best to use a limiting circuit to restrict the final velocity demand signal to be within certain limits expressed as certain fixed percentages of the proportioned velocity demand signal. For example, the upper limit could be 150% of the proportioned velocity demand signal and the lower limit could be 85% of that signal.

c. Optional Electronic Stop or Limit Function

To provide an electronic stopping function for the lever arm, a limit function computer 120 obtains inputs from the upper limits set 86 and the lower limits set 87 as well as the angle input to compute a limit velocity demand signal which will override the main velocity demand signal when its value is less than the main velocity demand signal. The torque sign computer 181 receives the torque signal from the direction control switching system 122 and signals to the limit function computer the direction that the lever arm is moving, namely, either toward the upper limit or toward the lower limit. The limit function computer then computes a limit velocity demand signal based on a prearranged functional difference between the currently active limit and the present position of the lever arm.

One such function may for example be the square root of the difference between the active limit and the present position of the lever arm. The value of this signal is calibrated such that it will have no effect on the final velocity demand signal out of the minimum value computer until the lever arm approaches to a certain point with an associated difference in angular position from the active limit. The final velocity demand signal FVD out of the minimum value computer 119 is fed to the predictive function computer 123 along with the absolute torque output from the absolute torque computer. The predictive function computer 123 functionally combines the final velocity demand signal and the absolute torque signal to produce a position control signal PC. The PC signal is fed to a compensation computer 124 which applies a correction factor to the PC signal based on the known average characteristics of the hydraulic rotary actuator and flow control system. The final compensated position control signal CPC from the compensation computer 124 is fed to the error circuit 103 to be combined with the valve position signal VP from position monitor 104 to produce a final position control signal FPC into the valve position drive circuitry 102.

The velocity control computer system 90 depicted in FIG. 10 eliminates certain of the calibration steps which were required in the velocity control computer system disclosed in the parent application. The velocity control computer in the parent application required a custom set of data points to be generated and stored in a read-only memory in order to compensate for the actual operating characteristics of the actuator and hydraulic flow control system of each actual unit manufactured. While that approach is effective in providing accurate velocity control, it limits the flexibility of manufacturing and repair in terms of marrying the particular components of a system together during initial manufacturing or during repair and replacement of parts in the field. The system disclosed in FIG. 10 eliminates this step of customized compensation and provides a velocity control computer arrangement which may be married with any set of components in the hydraulic system.

d. Specific Circuit Embodiment of the Analog Control System of this Invention

FIGS. 11 and 13-16 illustrate the details of implementation of one version of a velocity control computer system 90 in accordance with this invention. The particular implementation shown in these figures utilizes multiplying digital to analog converters for the computational functions which require multiplication or division. A multiplying digital to analog converter stores a latched digital word value. Depending on the configuration of inputs and outputs, an input analog signal is either multiplied by or divided by the stored digital word value.

In this case, the signal values which are to be multiplied by other signal values originate as analog signal values. Thus, it is necessary to convert these analog signal values to digital signal values and store them into the multiplying analog to digital converters to accomplish the multiplication and division function. Furthermore, in the case of the predictive function computer, in this implementation of the invention the implemented function involves dividing by the square root of the absolute torque value. Accordingly, the converted digital word value of absolute torque must be subjected to a square root functional computation.

Figure 11:
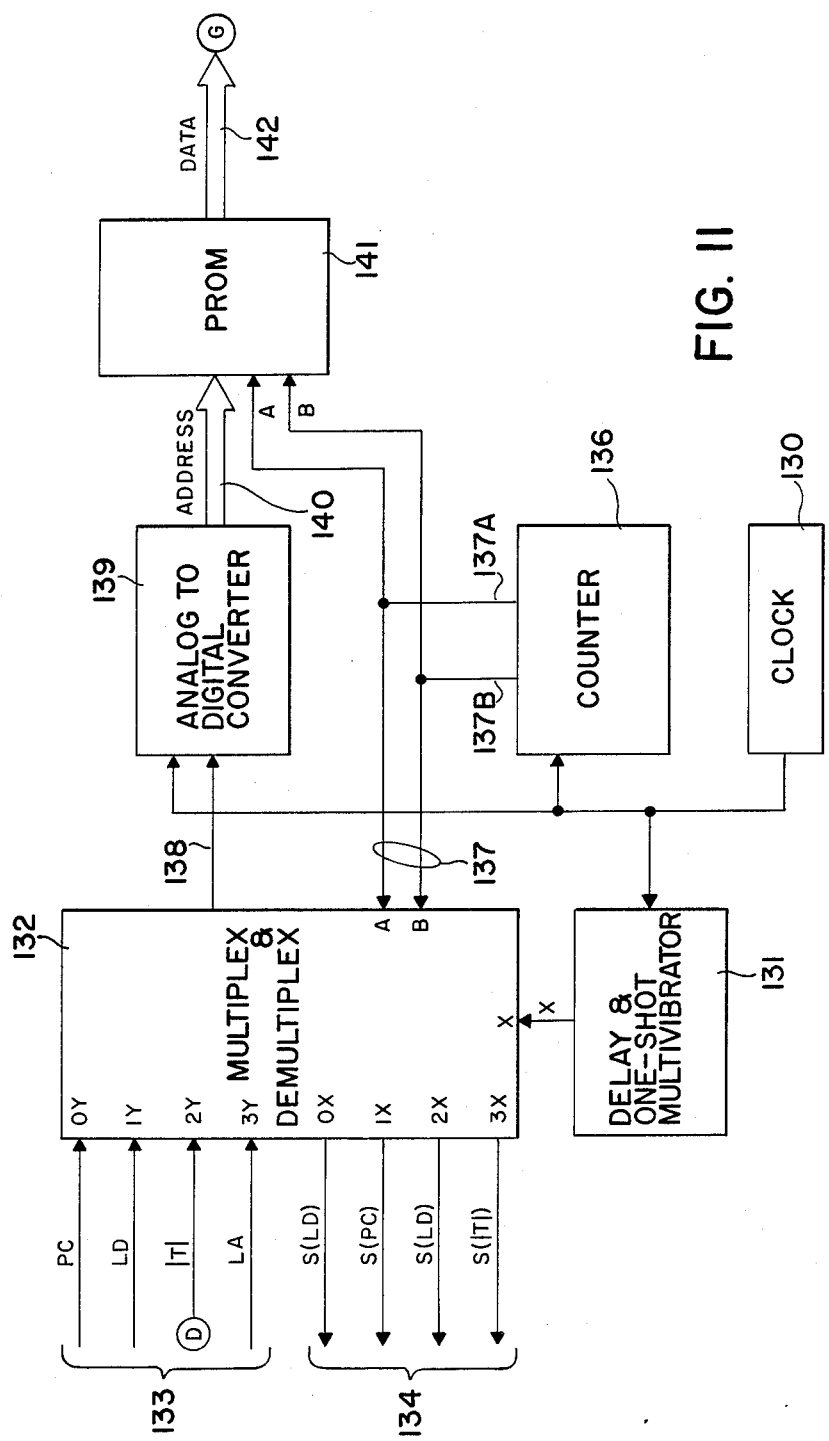
FIG. 11 is a block diagram of a portion of an analog computer system implementation of this invention.

The analog to digital conversion process required on the four separate analog signals involved in multiplication or division as well as the implementation of square root function calculations could be accomplished utilizing individual analog to digital converter circuits and complicated function calculation circuits. However, this would substantially increase the cost of the velocity control computer system. The preferred implementation of the system of this invention utilizes analog multiplexing of the four analog signals into a single analog to digital converter as shown in FIG. 11. A multiplex and demultiplex circuit 132 receives input analog signals 133 and couples a single one of the four input analog signals to an output lead 138 to analog to digital converter 139. The particular analog signal selected depends on the output value stored in counter 136 and thus the values of the digital output signals on leads 137A and 137B. The output of the analog to digital converter 139 is a digital word on address lines 140 to a programmable read-only memory 141. The other address inputs to PROM 141 are the counter outputs 137A and 137B. Accordingly, each of the converted digital word representations of each of the analog signals addresses a particular memory location in PROM 141 to read out a data word on data bus 142.

It can thus be seen that the counter 136 controls both which analog signal is coupled to the analog to digital converter and which section of the PROM memory, or which page in the PROM 141 is utilized as the look-up for converting the address on address bus 140 to a data word value on the data bus 142.

The analog PC signal when multiplexed into the analog to digital converter 139 produces an output digital address on address bus 140 which, along with the counter outputs 137A and 137B, addresses a section of PROM 141 which contains data corresponding to a compensation function. In other words, that particular page in the PROM 141 contains conversion data which changes the value of the address to a digital data value which is equal to multiplying the analog signal by a particular conversion factor. Both of the analog signals involving the limits delta LD and the absolute value of torque produce address signals which read data in PROM 141 which converts the analog input signal value to a digital signal value corresponding to a constant times the square root of the analog signal value. In other words, square root data values are stored in a page in the PROM 141 so that the digital address out of the analog to digital converter corresponding to the analog value of one of these signals looks up a data point on a square root conversion table corresponding to that value and outputs it as a digital word value on the data bus 142. The analog actual lever length signal LA involves a linear analog to digital data transform through the PROM 141.

Figure 12:
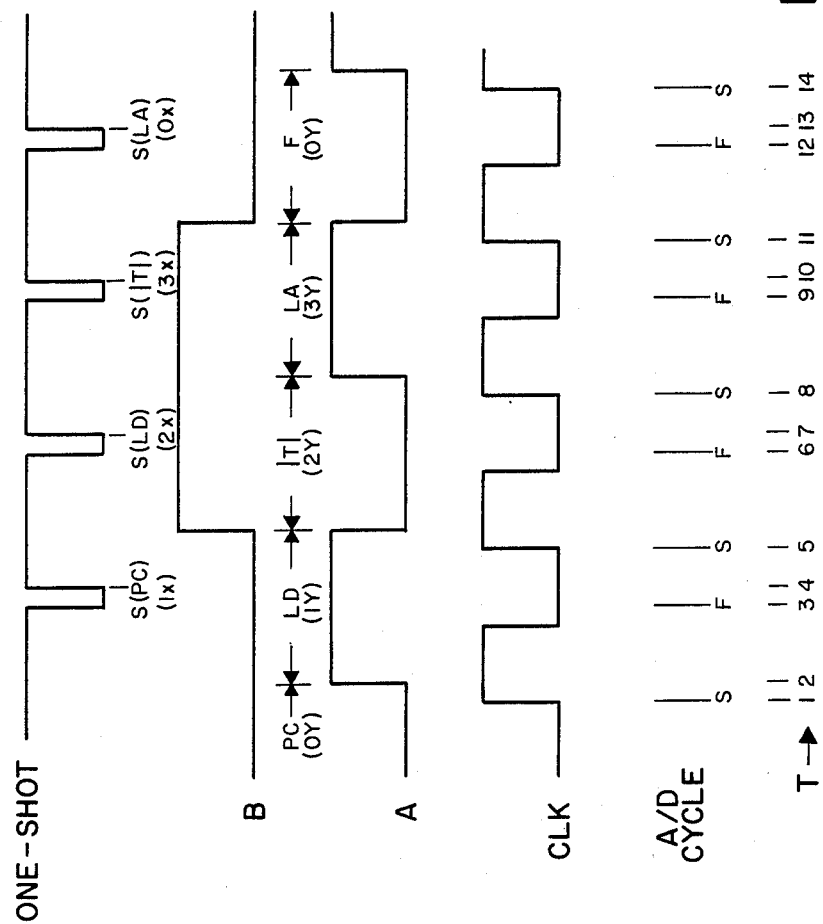
FIG. 12 is a timing and waveform diagram illustrating the operation of the circuitry illustrated in FIG. 11.

Multiplex and demultiplex circuit 132 also demultiplexes the strobing input on input X to four different strobe outputs based on the bit values on the inputs A and B from the counter 136. These strobes are distributed to the various multiplying digital to analog converters so that these strobes are present when data associated with the corresponding analog signal inputs 133 are present on the data bus 132 which is common with all the data inputs of the multiplying digital to analog converters. The operation sequence thus is that shown in FIG. 12 for example.

At time T1, the bit values on leads A and B are both 0 and the clock transition at time T1 causes the OY input of multiplexer 132 to be present on the Y output to analog to digital converter 139. Thus with the clock transition, the PC analog input is communicated to the analog to digital converter and the conversion process starts as represented by the S point on the A to D conversion cycle of the graph of FIG. 12. At time T2, involving a short digital delay cycle, the value stored in counter 136 changes so that the A bit on 137A has a 1 value while the B line stays at 0. This causes the limits delta analog signal to be output on the Y lead 138 to prepare it to be accepted by the analog to digital converter on the next clock transition. At time T3 the analog to digital converter cycle is finished, and at time T4 the output of delay and one-shot and multivibrator circuit 131 strobes the x input which is distributed as the 1X strobe output labelled S(PC). At that point in time the address value on address bus 140 and the corresponding data on data bus 142 are, respectively, the digital value of the PC signal and the corresponding data value read from the corresponding page in the PROM for the PC signal. Note that the address inputs A and B at the time the address corresponding to the PC signal arrives are different from the address values when the PC signal was strobed into the analog to digital converter. This requires that the appropriate sections of PROM 141 be loaded with the appropriate depending on the addresses that will be presented out of the counter 136 in the appropriate timing sequence.

At time T4 the S(PC) strobe causes the data on data bus 142 to be latched into the corresponding multiplying digital to analog converter which is operating on the digital PC signal. Remembering that the digital PC signal is a converted or compensated version of the analog PC signal, the output of the multiplying digital to analog converter is a constant times that converted signal, providing the compensated position control signal CPC.

At time T5 another clock signal arrives and the analog LD signal is strobed into the analog to digital converter 139 and the conversion cycle started. The same sequence of events occurs with respect to the conversion of the LD signal the production of the S(LD) strobe at time T7 after the conversion has completed and the toggling of the counter 136 to its next value to set up the next input to the analog to digital converter, namely the absolute value of torque input.

It should thus be apparent that the circuitry of FIG. 11 is an inexpensive and effective way of combining analog to digital conversion with manipulation of the digital word values to data values which represent either a linear conversion or a complex functional conversion based on stored data values in sections of the PROM 141. In this case the conversion is a square root function conversion, but other functional conversions could also be implemented with this approach. As previously indicated, this same result could be achieved by using separate analog to digital converters and separate PROMs, each dedicated to a particular analog signal conversion process. However, the rate of change value of the analog signals is such that a sampling rate of 1000 Hz is more than sufficient to handle the signal level changes that occur in this system.

Figure 13:
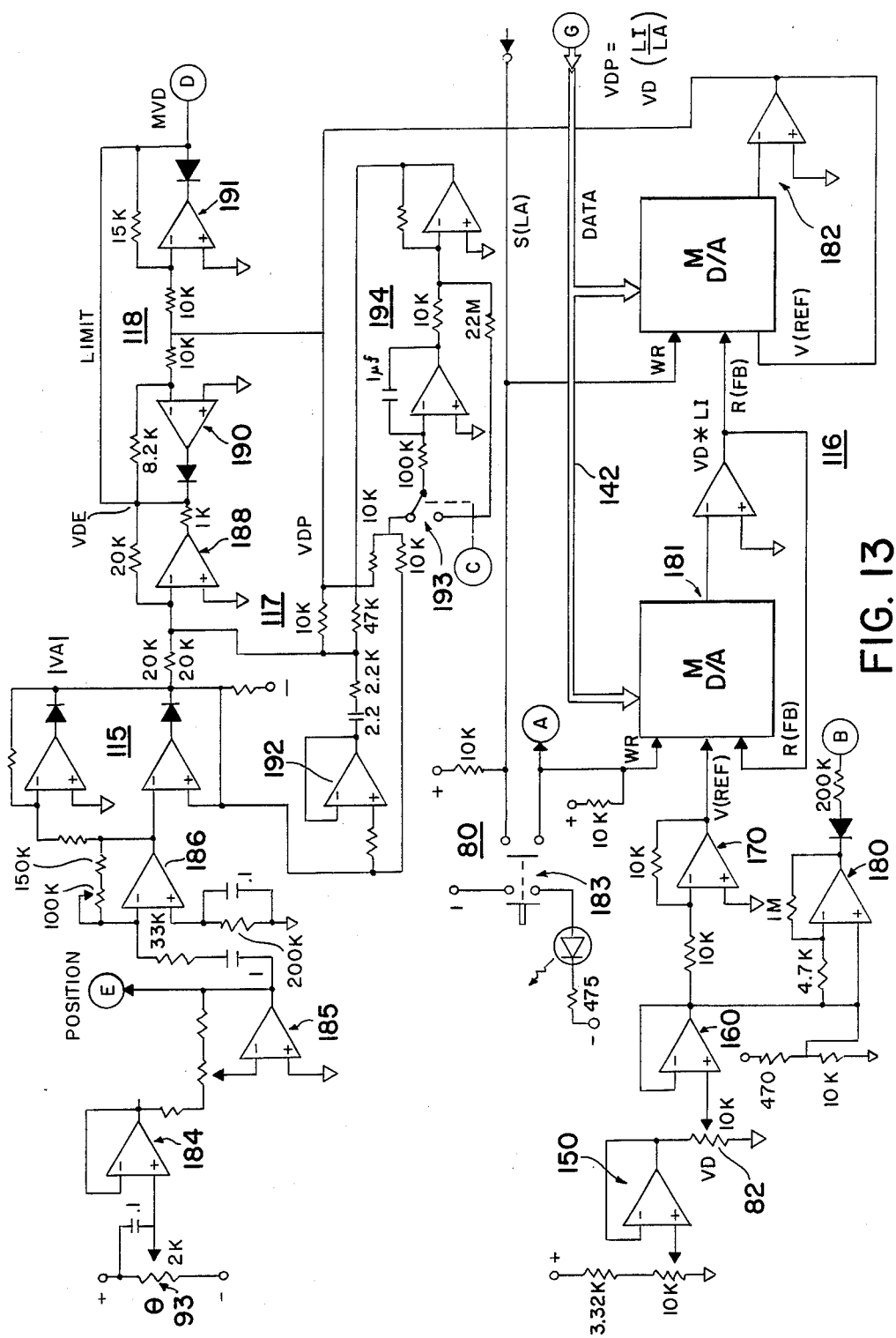
Figure 14:
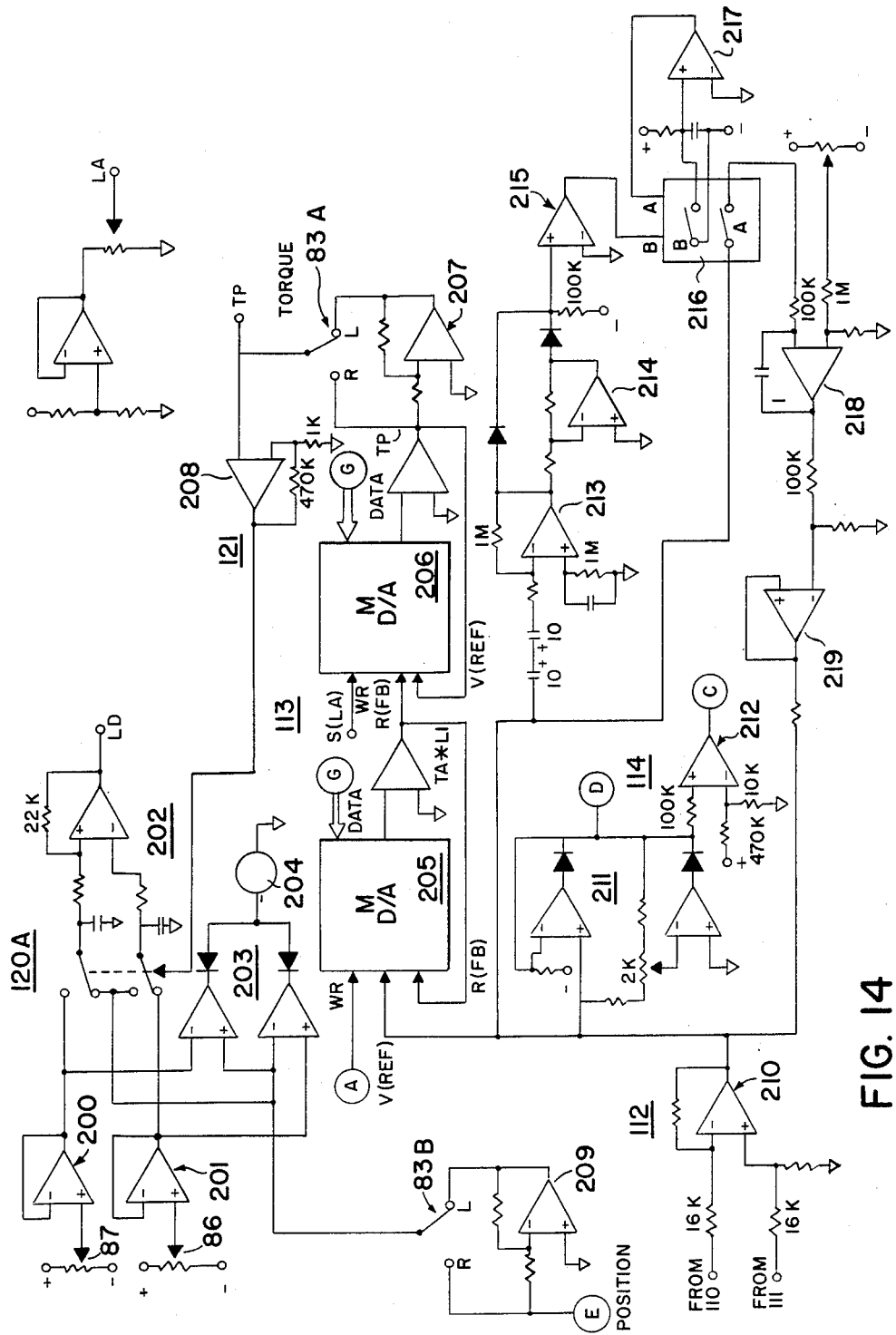

Referring now to FIGS. 13-16 in connection with FIG. 11, a presently preferred implementation of the system concept disclosed in FIG. 10 will be described. FIG. 13 illustrates analog computer circuitry which comprises an absolute velocity computer 115, a proportional velocity demand computer 116, summing circuit 117 and limiting circuit 118. FIG. 14 illustrates circuitry for limit function computer 120, torque computer 112, proportional torque computer 113, and absolute torque computer 114. FIG. 14 also discloses a torque baseline correction circuit similar to the circuit utilized in the embodiment disclosed in the parent application.

FIG. 16 discloses minimum value computer 119, a portion 120B of the limit function computer 120, a predictive function computer 123 and compensation computer 124. FIG. 16 also illustrates position monitor circuit 104, error circuit 103 and valve position drive circuit 102, as well as the electrical aspects of the flow control valve 101.

Referring to FIG. 13, the angle potentiometer 93 which tracks the angular position theta of the lever arm has its output connected to a unity gain buffer amplifier circuit 184, whose output, in turn, is coupled to a variable gain amplifier stage 185 used for calibration of the angular position signal. The output of variable gain amplifier circuit 185 is coupled into a differentiating amplifier circuit 186, whose output in turn is coupled to an absolute value circuit 115. The differentiator circuit 186 produces a signed velocity signal by differentiating the position signal. Here differentiation is used in the mathematical sense of producing a signal which represents the time rate of change of position. In this case, since it is angular position, the differentiated output is angular velocity. The absolute value of the angular velocity, in this case the actual angular velocity of the lever arm, is fed as one input through a 20K resistor to summing amplifier stage 188. The output of summing amplifier stage 188 is fed directly to the output D for use in another part of the circuitry as described below.

The other primary input to the summing amplifier circuit 188 is the proportioned velocity demand signal VDP which is output from the multiplying digital to analog converter stage 182. The VDP input is coupled through a 10K resistor, and its polarity is such that it is summed by the summing circuit as a positive two times input, while the absolute value signal is summed as a negative one times signal. The VDP signal is also fed directly to the limit circuit 118 which comprises a first limit amplifier stage 190 which has a gain value determined by the 8.2K feedback resistance and the 10K input resistance which limits the signal value at point D to be no less than 80% of the value of the VDP signal. In other words, if the value of twice the VDP signal level less the absolute actual velocity is equal to a value less than about 80% of the VDP signal alone, the diode in the limiting amplifier circuit 190 will be forward biased, and a signal equal to about 80% of VDP will be coupled as the MVD signal on output D. The limit amplifier circuit 191 is arranged such that its gain sets a condition such that if the VDP signal is greater than 150% of the VDE signal, the maximum value that can appear on the D output as the MVD signal is 150% or 1.5 times the VDP signal.

Consider the conditions under which these circuits might come into effect. If the proportioned velocity demand signal VDP is set to a certain value, but the lever arm is not moving so that the absolute angular velocity value is zero, the output of the summing amplifier circuit 188 designated VDE would be 200%, or two times the value of the proportioned velocity demand signal VDP. Under this condition, the limiting amplifier circuit 191 limits the value on output D to be 1.5 times the value of VDP. This is the most typical condition under which the limiting circuit 118 would come into effect. The lower limiting circuit is effective during an overshoot condition in which the flow control valve may have opened too wide, permitting the actual velocity signal to rise above the proportioned velocity demand signal by more than 20%. This would tend to cause the final position signal to the valve position drive to close down the flow control valve too far during this overshoot condition. The lower limit circuit 190 prevents the overshoot from taking effect above about 80% of VDP value, and thus prevents too tight a closing of the flow control valve. Thus the limit circuit provides for more smooth transitions and improves the dynamic response of the system.

It is also seen in FIG. 13 that the absolute velocity value is fed through a unity gain buffer 192 and a differentiating capacitor-resistor network into the summing junction at the input of summing amplifier circuit 188. This provides a second derivative of the velocity function or, in other words, measures the acceleration of the system. This acceleration value signal is used to limit the rate of acceleration of the lever arm to a certain maximum value. Under high acceleration, the negative second derivative signal, or negative acceleration signal value is additive to the absolute value of angular velocity, and tends to create a reduced final velocity demand signal at the modified velocity demand output D.

FIG. 13 also shows another correction circuit which involves summing the opposite polarity proportioned velocity demand signal and the absolute velocity signal at the input to a integrating amplifier stage 194 when the switch 193 is in the position shown. Switch 193 is in the position shown when the magnitude of the absolute torque value exceeds a certain threshold setting at the amplifier stage 212 in FIG. 14. If control system has drifted out of calibration so that the average value of the proportioned velocity demand signal varies substantially from the absolute velocity value, this difference will be integrated on the capacitor in the integrating amplifier circuit and the output will be fed back as a correcting signal through a higher resistance value 47K, to provide a very sensitive correction to a drift in calibration. Since this integration of differences between these two signals should only occur when the lever arm is moving with fairly substantial torque applied, i.e. so that the actual velocity is near the demand velocity signal, the switch 193 will open and begin to discharge the integrating capacitor when the torque falls below a certain value.

The proportioned velocity demand signal is developed in the proportioned velocity demand computer circuit 116 which utilizes two multiplying digital to analog converter stages 181 and 182. First consider the multiplying digital to analog conversion stage 181. The limb length pushbutton 183, when pushed, couples the strobe signal for the actual lever length signal, designated S(LA) to the write input WR to the multiplying digital to analog converter stage 181. Accordingly, the actual length of the lever arm which is represented by the digital word value on the data bus 142 at the time of the S(LA) strobe signal is loaded into the multiplying digital to analog converter stage 181. This pushbutton is pressed once, as previously explained, to store the neutral limb length value into the system. As shown in FIG. 14, this same pushbutton controls the coupling of the S(LA) strobe signal into the multiplying digital to analog converter 205 which is used for proportioning the torque signal. Thus a single press of the initial limb length pushbutton 80 loads the initial digital word value corresponding to the initial limb length on the data bus 142 into the digital storage of the multiplying digital to analog converters.

The analog input to the multiplying digital to analog converter 181 is the velocity demand signal VD set by the velocity set potentiometer 82 which is fed by unity gain amplifier stage 150 forming part of a calibration circuit. A buffer stage 160 and a inverting amplifier stage 170 are used to couple the velocity demand signal into the V(REF) input to multiplying analog to digital converter 181. The output amplifier stage on the multiplying digital to analog converter and the feedback of the output into the R(FB) input organizes the D/A converter 181 such that the analog velocity demand signal input is multiplied by the stored digital word value representing the initial limb length LI.

The output of the D/A circuit 181 is fed to the R(FB) input of the D/A circuit 182. The output of the output amplifier stage of the D/A circuit 182 is fed back to the V(REF) input so that the D/A circuit 182 operates to divide the analog signal representing VD times LI by the value of the actual limb length which is stored into D/A circuit 182 each time the strobe signal S(LA) appears to write the digital data word value on the data line 142 into the D/A circuit 182. The output of the D/A circuit 182 is thus the proportioned velocity demand signal which comprises the velocity demand value ratioed by the initial lever arm length and the actual lever arm length at each instant in time.

As discussed above, the sampling of the actual limb length signal is occurring fast enough that the D/A converter stage 182 will effectively respond to any changes in the actual lever arm length. As shown in FIG. 14 the lever arm length is measured by a potentiometer circuit fed by a unity gain amplifier stage. The output from the potentiometer feeds the multiplexer circuit shown in FIG. 11.

A difference amplifier circuit 180 is also provided with an input of the velocity demand signal VD from the buffer stage 160 to produce an output signal at point B. The output signal at point B is coupled to the error circuit 103 in FIG. 16 directly. Thus when the velocity demand setting is very low, this direct coupling of the velocity demand signal to the input of the error circuit 103 will produce a very tight closing of the flow control valve. This produces a discontinuity in the velocity demand signal so that at very low settings the arm cannot be set into motion except under extremely high torque conditions. Thus this circuit does not usually come into play during the actual use of the system.

Referring now to FIG. 14, the torque computer circuit 112 comprises a differential amplifier stage 210 receiving the individual torque inputs from the pressure transducer systems 110 and 111. The difference circuit stage 210 produces an output which represents the signed torque value which is fed as an input to the multiplying digital to analog converter stage 205 and to an absolute torque computer 114. The output of the absolute value circuit 114 at point D is coupled into the multiplexer circuit 132 shown in FIG. 11.

As described above, the multiplying digital to analog converter stage 205 has stored in it the initial limb length. Accordingly, the output of the D/A stage 205 is the value of actual torque TA times the initial limb length LI. This output is fed to D/A stage 206 which is configured such that it divides the output signal from the previous stage by the digital data word stored in that D/A stage which is the last value loaded in corresponding to the actual lever arm length setting. The output of this D/A stage 206 is the proportioned torque signal TP which is fed to the right/left switch stage 83A directly and through an inverting amplifier stage 207.

The switch output becomes the proportioned torque signal having its sign corrected for the particular position of the exercise system relative to the patient exercising. The amplifier stage 208 is configured such that it has an output which is positive when the proportioned torque signal is positive an negative when the proportioned torque signal output is negative. Accordingly, this circuit computes the sign of the torque and is the torque sign computer 121 shown in FIG. 10. The output is fed to a digitally controlled switch stage 120A which is part of a limit function computer 120 whose operation will be described below.

The position signal at point E in FIG. 13 is fed through the right/left switch stage 83B both directly and through an inverter 209 so that the output of the switch stage 83B will be a corrected position signal depending on the setting of the right/left switch. This corrected position signal is fed to a pair of amplifiers comprising a window circuit stage 203 with this pair of difference amplifiers also receiving inputs from the lower and upper limit set potentiometers 87 through unity gain buffer stages 200 and 201. The window circuit 203 sounds the buzzer 204 when the position signal is equal to either the value of the upper limit set circuit or the lower limit set circuit. The position signal is also fed to the digitally controlled switch stage 120A, where depending on the setting of that switch stage, it is either coupled into the plus input of the difference amplifier stage 202 or into the minus input of that stage. In the switch position shown in FIG. 14, coupling of the position signal into the plus side of the difference amplifier 202 along with the upper limit set signal being coupled into the negative input of the difference amplifier produces a limit difference signal LD which is equal to the actual position minus the upper limit set value. This signal is fed directly to the multiplexer 132 in FIG. 11 so that it can be converted to a digital signal value which addresses a section of the PROM 141 which converts it to a square root output data value.

Alternatively, if the sign of the torque circuit 121 places the switch 120A in the other position, the lower limit set signal is coupled to the positive side of the difference amplifier and the actual position is coupled to the negative side of the difference amplifier which produces a limits difference signal LD equal to the lower limit set minus the actual position. It is thus seen that this limits difference signal will be very large when the lever arm position is far from the upper or lower limits set and will be very small when the lever arm approaches one of the upper or lower limit.

The other circuitry shown in FIG. 14 is a torque baseline correction circuit which functions when the lever arm is quiescent for a several seconds to readjust the baseline to a zero reading.

A differentiator circuit 213 is used to determine when there is motion of the lever arm and thus some variation in the torque signal output. The output of differentiator circuit 213 is coupled through an absolute value circuit 214 into a comparator circuit 215 with a threshold established by a single diode drop (about 0.6 volts) so that the comparator is triggered by any significant change in torque value which in turn indicates that the lever arm is in motion. The output of the comparator 215 operates gate B in gating circuit 216 to reset timer 217 and thus keep it from closing gate A to couple the torque output signal value into the baseline setting circuitry.

However, during a quiescent condition of the lever arm, the timer circuit 217 will time out and close the gate A. Any nonzero output value of the torque signal at such time is detected in comparator 215 and fed as a baseline error signal to integrator 218 whose output changes in a direction to reduce the detected error. When gate A is later opened, the signal value at the output of integrator 218 remains constant as the current baseline correction value.

Referring now to FIG. 15, embodiments of minimum value computer 119 and predictive function computer 123 will be described together with a portion of the limit function computer 120. D/A converter 120B receives the strobe signal S(LD) to load data corresponding to the limits difference signal LD. The V(REF) input of D/A 120B is connected to a reference voltage RV. The configuration of D/A converter 120B is such that the input reference voltage is multiplied by the stored digital data word value. It will be remembered that the digital data value corresponding to the limits delta signal is, in accordance with this embodiment, a value equal to the square root of the analog value of the limits delta signal LD produced by circuitry shown in FIG. 14. Thus the output of the D/A converter system 120B is proportional to the square root of the value LD.

Minimum value computer 119 involves an arrangement of amplifiers and diodes at their outputs so that the output analog signal is the smallest of the two input signals. Accordingly, when the limits velocity demand signal LVD is smaller than the modified velocity demand signal from the limiting circuit 118, the limit velocity demand signal LVD will be present as the final velocity demand signal FVD. Otherwise, the final velocity demand signal FVD will be the modified velocity demand signal MVD from the limit circuit 118. This final velocity demand signal is fed to a D/A converter arrangement which serves as the predictive function computer 123. The write input of this D/A converter receives the strobe signal for the absolute value of torque. At the time of that strobe signal, the data value input to D/A converter 123 is a digital word value corresponding to the square root of the absolute value of the torque. The D/A converter arrangement 123 is configured such that the final velocity demand signal V is divided by the digital word value representing the square root of the absolute torque value.

Thus the final position control output signal PC is proportional to the final velocity demand signal divided by square root of the absolute torque. This position control signal PC is one of the inputs to the multiplexer 132 shown in FIG. 11. Its converted digital value addresses a portion of the PROM 141 which contains compensation values for nonlinearities in the relationship between the position control signal value and the flow control valve spool position required to produce the appropriate restriction on flow which will limit the maximum permitted angular velocity of the system to the values set by the final velocity demand signal.

FIG. 16 illustrates actual circuitry of the compensation computer 124, the error circuit 103, the valve position circuit 102 and the position monitor circuit 104. The compensation computer 124 involves a multiplying digital to analog converter which is arranged to multiply the analog reference voltage RV input by the data word value strobed into the D/A converter by the PC strobe signal. This data value represents a compensation data word value so that the final output signal is a compensated position control signal CPC which is fed to the summing circuit 103.

The summing circuit 103 sums the compensated position control signal and the output signal of the position monitor 104 to produce a final position control signal FPC input to the valve position drive circuit 102. It is seen in FIG. 16 that the input of the absolute value of torque is differentiated in a capacitor/resistor network 260 and fed at the input of the summing circuit 103. This differentiation of the absolute torque signal responds to the rate of change in the absolute torque value such that if the torque signal is rapidly increasing, it will cause the valve to open a little more. This improves the overall dynamic response of the system.

The summing circuit 103 includes a diode network 241 which limits size of the error signal and improves the recovery characteristics of the servo loop. The final position control signal FPC is coupled to a pair of respective minus and plus inputs of the difference amplifiers 246 and 247 in the valve position drive circuit 102. The other inputs to these difference amplifiers are modified sawtooth waveforms from a triangular waveform oscillator 243 coupled through the amplifier stages 244 and 245. The complementary comparators 246 and 247 drive field effect transistors 248 and 249 with duty cycles of the drive signals which depend on the value of the final position control signal.

The outputs of the field effect transistors 248 and 249 are coupled to the solenoids 250 and 251 which drive the valve spool in the flow control valve 101 in a push-/push relation. With this arrangement the final position control signal FPC controls the amount of time that each of the complementary comparator stages 246 and 247 are turned on to drive their respective field effect transistors. The differential duty cycle pulsing of the operation of the solenoids controls the average energization of the solenoids and thus the final position of the valve spool which is in a push/push relation with the solenoids. A temperature sensor 260 mounted on the housing of the rotary actuator has its output coupled through an amplifier stage 242 into the input of the summing circuit 103 to provide a correction signal for the temperature of the actuator. This assists in maintaining overall calibration of the system with changes in temperature of the actuator which can affect the flow characteristics of the hydraulic fluid in the hydraulic circuit thereof due to changes in viscosity with temperature.

The position monitor circuit 104 functions in the following manner. The proportional solenoid includes a transformer system including a primary winding PRI and a pair of secondary windings SEC1 and SEC2 which are coupled in complementary manner to the primary winding. Thus, for a fixed AC signal input to the primary winding the output from the secondary windings coupled in series as shown will be a signal proportional to solenoid position. The primary winding is coupled to a square wave oscillator 235 through an amplifier circuit 236. The output of the square wave oscillator 235 also operates signal sampling gates A and B within gate circuit 238 to sample the value of the signal output from the secondary windings through unity gain amplifier 237. The sampled signal is stored in hold circuit 239 and fed to summing circuit 240. The square wave oscillator 235 may operate at a frequency in the range of 2 to 10 kHz.

In the circuits shown in FIGS. 13–16, all of the resistors are 10K resistors, unless otherwise specified. All of the capacitors have a value of 0.1 microfarad, unless otherwise indicated on the drawing.

5. The Digital Computer Control Circuit Embodiment

The same basic function of a velocity control computer of the essentially analog computer type shown in FIGS. 10–16 can be provided in a velocity control computer which is basically performing digital signal processing and computation. FIGS. 17–20 illustrate the hardware of such a digital signal processing version of this invention.

A preferred version of the software program running in the programmed computer which is at the heart of the processing type is depicted in FIGS. 21–28.

a. Control Panel Arrangement

Figure 17:
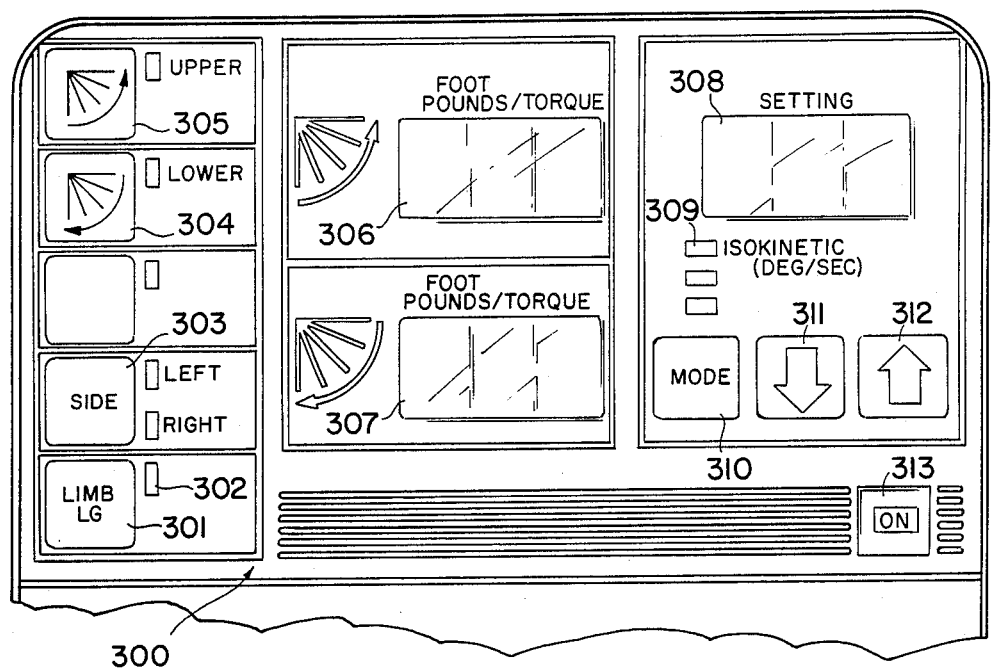
FIG. 17 is a drawing illustrating a control panel for a digital version of an exercise system in accordance with this invention.
Figure 9:
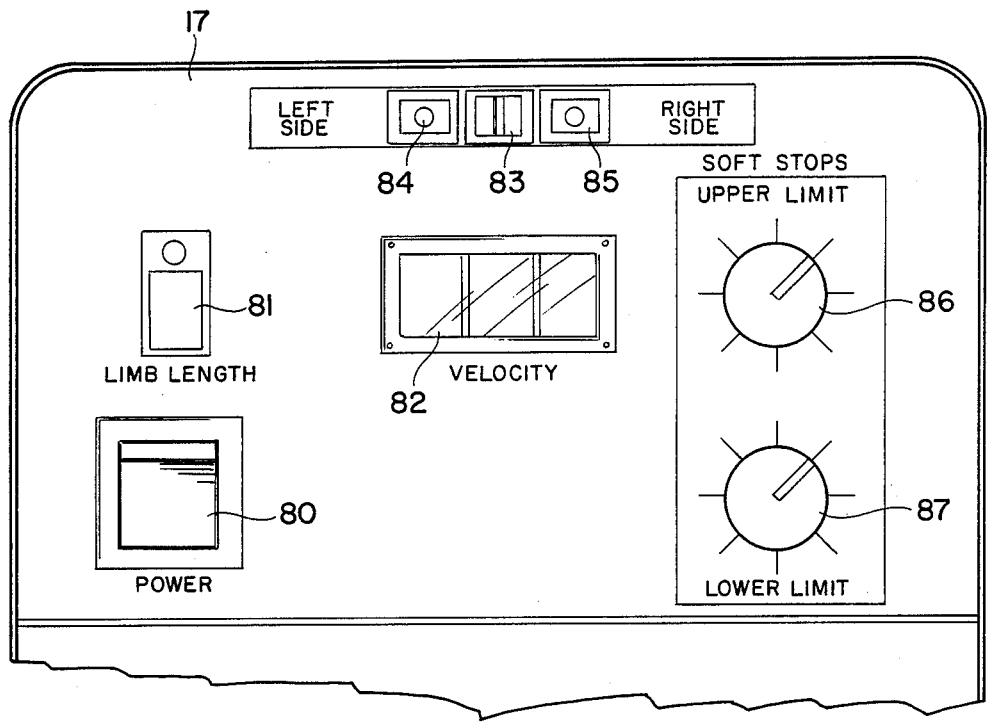
FIG. 9 is a drawing illustrating a control panel for an analog version of an exercise system in accordance with this invention.

Referring now to FIG. 17, an embodiment of a control panel for a digital signal processing version is depicted. Each of the setting controls in the digital version control panel 300 is a single make contact pushbutton. Each of the controls has an associated LED display indicating when that control has been set. The limb length pushbutton 301 is used to signal the computer to set the initial limb length and light the LED 302 when that has been accomplished. The side pushbutton 303 toggles the setting in the computer between LEFT and RIGHT each time it is pushed. The initial default condition is RIGHT and a single push of the side button toggles the stored input to the LEFT condition. The upper and lower limits set pushbuttons 304 and 305 are depressed when the lever arm is at the limit condition desired for the relative upper and lower excursion of the lever arm.

The mode pushbutton 310 toggles the control mode of the digital computer program between the various modes of control, only one of which, namely the isokinetic mode, is illustrated. Other modes can be provided as will be discussed below. The pushbuttons 311 and 312 toggle the setting of the control parameter associated with the particular mode either up or down. Thus in the isokinetic mode, the pushbuttons 311 and 312 respectively control the lowering or raising of the velocity setting in degrees per second. As that setting is toggled, the LED display 308 shows the current setting. The two LED displays 306 and 307 display the torque values during flexion and extension of the body portion being exercised. Pushbutton 313 is an on-off pushbutton which controls power to the system.

b. General Digital System Concepts

Figure 18:
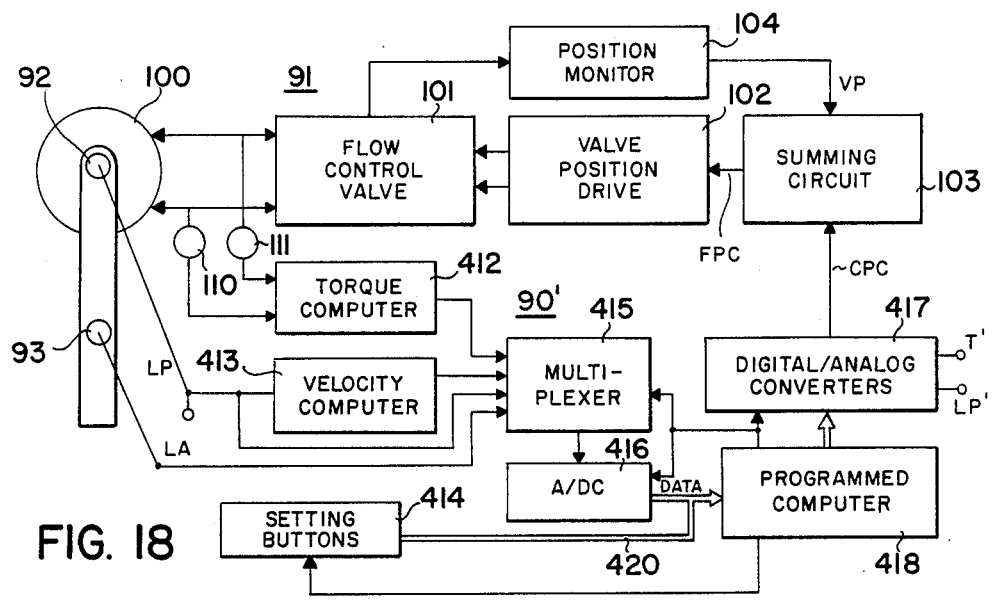
FIG. 18 is a block schematic diagram of a digital computer system implementation of the exercise system of this invention.

FIG. 18 is a block diagram which illustrates a digital signal processing version of a velocity control computer 90' in accordance with this invention. A torque computer 412 and a velocity computer 413 have their outputs coupled into multiplexer 415 along with the actual limb length signal LA and the lever position signal LP. The setting buttons 414 provide data on a dataline 420 under programmed computer control. Multiplexer 415 functions under the control of programmed computer 418 to multiplex one of the input analog signals to the analog to digital converter 416. Analog to digital converter 416 functions under computer control to convert the analog signal at its input to a digital data signal for input to the programmed computer 418. Digital to analog converters 417 receive output data from the programmed computer 418 and function under its control to provide output analog signals. One of these output analog signals is the compensated position control signal CPC. The other two output signals are torque T' and lever position LP' representing correct values for these parameters.

It is seen from FIG. 18 that there are two analog computer circuit systems remaining in the velocity control computer system in this particular implementation. The torque computer 412 and the velocity computer 413 are conveniently implemented in analog computer circuitry to reduce the number of digital inputs that have to be taken into the programmed computer. It should be understood that the torque computation could be accomplished by separately multiplexing and converting the outputs of the pressure transducer subsystems 110 and 111. It should also be understood that the velocity computation could be made by the programmed computer instead of utilizing an analog version of that computational function.

Figure 19A:
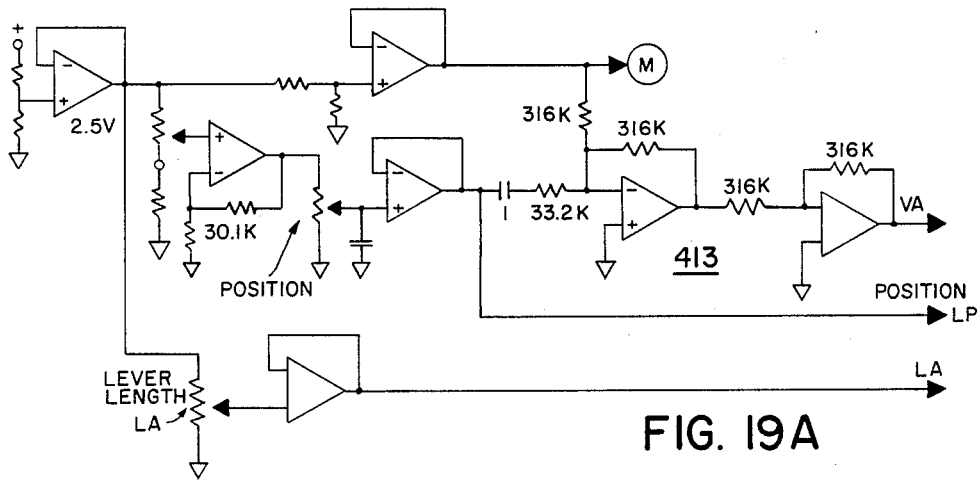
Figure 19B:
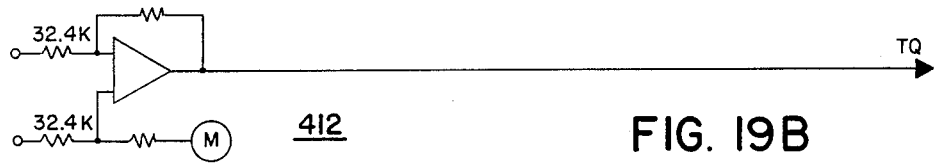

FIGS. 19A and 19B illustrate the torque computer 412 and velocity computer 413. For convenience, the actual velocity signal VA and the torque signal are level-shifted to be unipolar signals with the midpoint of the signal excursion equal to one-half of the maximum input signal range of the analog to digital converter. This shifts the digital zero value for bipolar analog signals to a ten-bit digital word value equal to 512 where the total range of digital values is between 0 and 1023. All of the resistor values shown in FIGS. 19A and 19B are 10K unless otherwise indicated. All of the capacitor values are 0.1 microfarads unless otherwise indicated.

FIGS. 20A-20E illustrate the remainder of the velocity control computer circuitry. The programmed computer 418 is a off-the-shelf single board computer system available from DY-4 Systems, Inc. of Campbell, Calif., and is known as the DSTD-102 CPU and Serial IO System. As an alternative, another computer system, the Ziatech ZT8806 CPU Board can be used. The construction and operation of these single board computer systems are very standard, are well understood by persons knowledgeable in this art and need not be described in detail here. Other forms of computer systems could be used.

The address decode circuit 422 receives address signals from computer 418 and decodes those address signals to provide control signals which select certain components to become functionally active for data input or output. For example, the decoded address DA0 is coupled to analog to digital converter 416 and controls its operation along with the read RD and write WR inputs from the control bus of the computer 418.

The decoded address line DA1 is fed to the digital to analog converter 417A to select it as the active element. When DAC 417A then receives a write WR, the data currently on the data bus is strobed into DAC 417A and converted to an output torque signal. Thus the computer system 418 has total control over the operation of the DAC 417A and the analog output which it provides by outputting digital data word values on the dataline at the time the decoded address DA1 is present and a write signal is issued. Similarly, the decoded address signals DA2 and DA4 control the selection of DACs 417B and 417C. Decoded address line DA3 controls the clocking of data into latches 421 with the latch outputs being communicated to multiplexer 415 to control which of the four analog input signals are coupled to the input of ADC 416. In this manner, computer 418 has complete control over the analog signal to be set up for conversion to digital data and complete control over the starting of the conversion process and reading of the converted digital data onto the output data bus for communication back to the computer 418.

Decoded address line DA1 selects the tri-state buffer 424 to be active for reading the condition of the pushbuttons 414 by way of the data bus. Decoded address lines DA5, DA6 and DA7 selectively control the operation of latches 430 and display drivers 431 so that data values on the data bus can be latched into storage and then displayed on the front panel displays of the system. The components required to do this are very standard and need no detailed explanation here.

From the above, it will be seen that computer 418 has functional control over all inputting and outputting of data and control signals for operating the exercise system of this invention. There are variations which could be introduced into this overall approach. For example, separate analog to digital converters could be used for each of the analog signals if desired. All of the pushbutton signals could be multiplexed into the analog to digital converter if there were some reason to acquire actual control setting data rather than simple switch position indications.

Comparing the mostly digital embodiment of this invention shown in FIG. 18 with the principally analog version shown in FIG. 10, it is seen that the overall circuit complexity of the digital version is substantially reduced. Functional computations are provided by the programmed computer 418 which processes the input analog signals to produce an appropriate compensated position control signal, first as a digital word value which is then output to a digital to analog converter which converts it to an appropriate analog signal for use by the summing circuit 103 to control the actual flow control valve position. As will be discussed in more detail below, this approach provides for substantially greater flexibility in the velocity control algorithms which can be implemented in the system. The digital version also makes it relatively simple to control the exercise and diagnostic system of this invention from a remote computer system by communicating the program parameters to programmed computer 418 instead of setting those parameters from the front panel.

c. The Software Control System and Method (1) Interwoven Interrupt Program Structure FIGS. 21 and 22 illustrate the structure of the software routines which comprise one implementation of the system and method of this invention. A power on or MAIN routine executes when the system is first powered up to set certain flags and to initialize the system. After this is done, the BACKGROUND routine executes in a continuing loop unless and until there is a 100 Hz interrupt. Upon the receipt of each 100 Hz interrupt, the 100 Hz routine begins to execute and continues execution unless and until there is a data transmission interrupt which has the highest interrupt priority. The 100 Hz routine performs basic data capture operations and executes math routines to calculate the COR.-POS.CMD signal to send to the summing circuit and the TORQ.OUT and LEV.POS.OUT signals which are sent to DACS whose outputs may be coupled to a chart recorder or other data display device.

After every sixteen executions of the 100 Hz routine, the 6.25 Hz routine will execute. The 6.25 Hz routine performs torque and velocity baseline measurements, executes front panel routines and calculates the PRI- OR.VEL.ERR value. The values of the parameters which are read and/or calculated in the 6.25 Hz routine are held and passed to the 100 Hz routine for use in sections of that routine. The data transmission routines performs basic serial data communications between the on-board, real-time control computer system and the remote computer system which performs data processing and display functions and/or downloads control information to the on-board computer system.

FIG. 22 illustrates the interweaving of program execution among the various routines. At each 100 Hz. interrupt tick, the 100 Hz routine begins execution. It may be interrupted as shown by data transmission interrupts which will grab small pieces of processor time to perform data transmission functions. After the 100 Hz routine is finished execution, the 6.25 Hz routine or the BACKGROUND routine will execute depending on the number of executions of the 100 Hz routine which have occurred. The 6.25 Hz routine may not complete executing before the next 100 Hz interrupt tick occurs. The status of the 6.25 Hz routine is saved while the 100 Hz routine again executes to completion and then the 6.25 Hz routine continues where it left off. Depending on the length of the 6.25 Hz routine, it may take several cycles between 100 Hz ticks before it has had sufficient time to complete its execution. When the time between the end of the 100 Hz routine and the receipt of the next tick is not used to process the 6.25 Hz routine, the BACKGROUND routine is processed. The BACKGROUND routine is interrupted many times before it completes its execution, but its place of execution is saved and it returns to that place when it again is allocated processor time.

(2) The MAIN Software Routine

Figure 23:
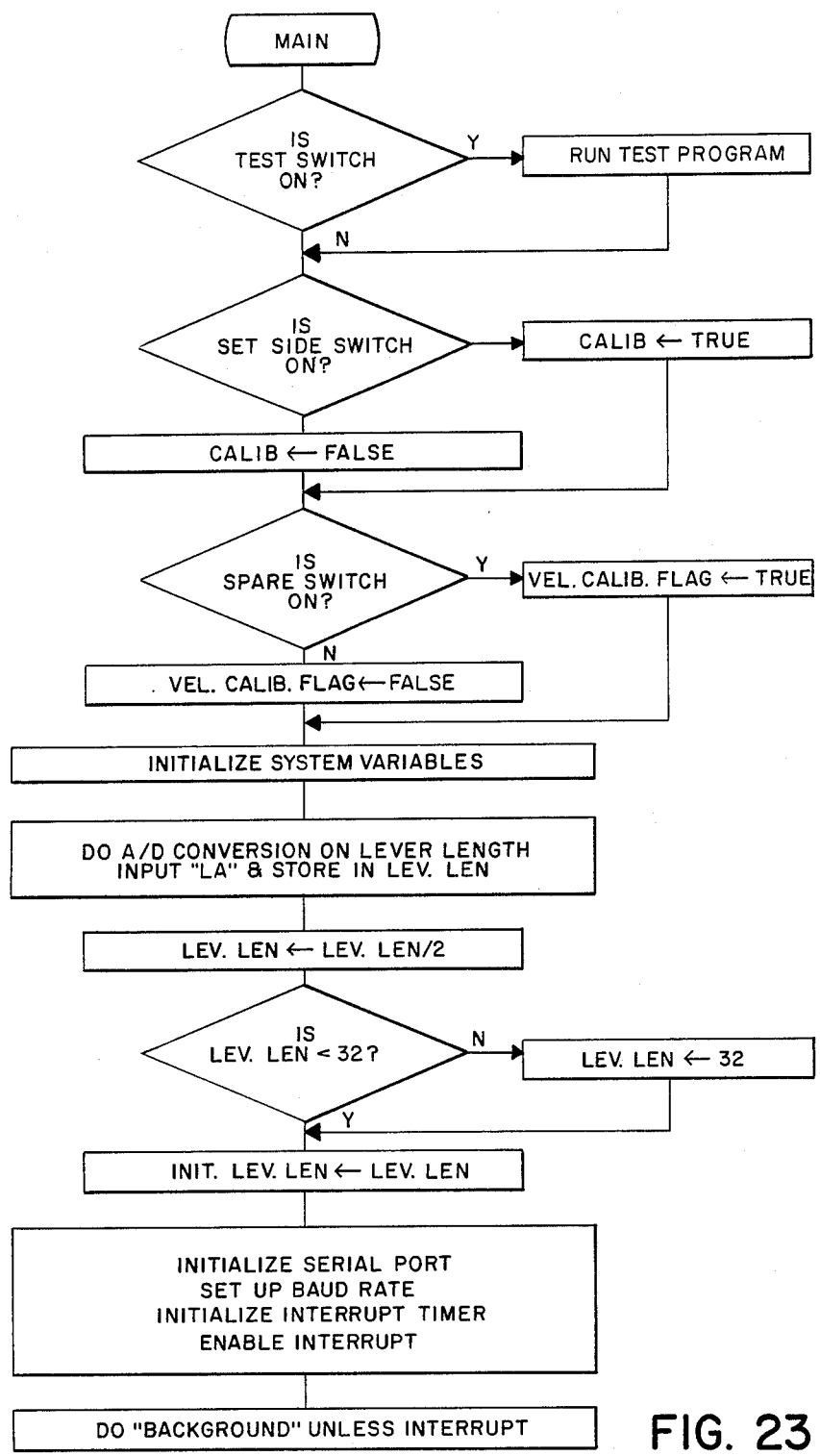
FIGS. 23 and 24 illustrate software control routines useful in a programmed digital computer version of the system of this invention.

FIG. 23 illustrates the main software routine which executes on initial power-up of the system. This main routine begins with a checking step to determine whether the test switch on the input-output board is ON to indicate that a test program should be run. The test program runs certain diagnostic tests on the system in order to determine whether it is functioning correctly. This is not a part of this invention and will not be described here.

The MAIN routine then executes a checking step to determine whether the SET SIDE switch is ON. This checking step is present to enable the system to be put into a calibration mode on power-up. Typically, this would be done at the factory or by service personnel doing a calibration function on the system. In other words, if the SET SIDE switch is pressed when the power is turned on, the calibration variable is set TRUE. If the set side switch is not on, the calibration variable is set FALSE.

The next checking step is to determine whether the spare switch is depressed. If this checking step returns a YES, the VEL.CALIB.FLAG is set TRUE. If this checking step returns a NO, that flag is set FALSE. The purpose of this is to enable certain tests or diagnostic functions to be performed on the system. Under normal operation of the overall system by the end user, none of these checking steps would return a YES condition and the MAIN software routine would directly progress to initializing the system variables to startup values.

Following this a series of steps are performed to set an initial value for the INIT.LEV.LEN parameter which will not yet have been set by the user. Since the 100 Hz interrupt routine will execute a number of times before the 6.25 Hz interrupt routine is executed to accept front panel settings, this setting of the initial lever length parameter value puts the system into a definite condition which enables the lever arm to be easily moved to attach it to the patient prior to inputting the appropriate parameter settings for the system on the front panel. To accomplish this initial setting of initial lever length parameter value an analog to digital conversion step is performed on the lever length input "LA" and the digital word value is stored in LEV.LEN.

The next step is to make a scale adjustment on the LEV.LEN signal by dividing its value by two. Following this a checking step is executed to determine whether LEV.LEN has a value less than 32. If this checking step returns a YES, LEV.LEN is set to 32 in order to give it a minimum value. The purpose of this is to make sure that the INIT.LEV.LEN parameter is set to a certain minimum value for use in routines which follow. The next step in the routine is to set the INIT.LEV.LEN value to the LEV.LEN value to give that parameter or definite setting until change by use of the front panel control.

The next step is to initialize the serial port of the computer system, to set up the baud rate for the serial port, to initialize the interrupt timer for the 100 Hz interrupt and then to enable that interrupt so that the interrupt tick will occur at a 100 Hz rate. Following this, the program goes into a loop to do the BACKGROUND routine which is performed except when there is an interrupt routine being done at some interrupt level.

(3) The 100 Hz Routine

Figure 24A:
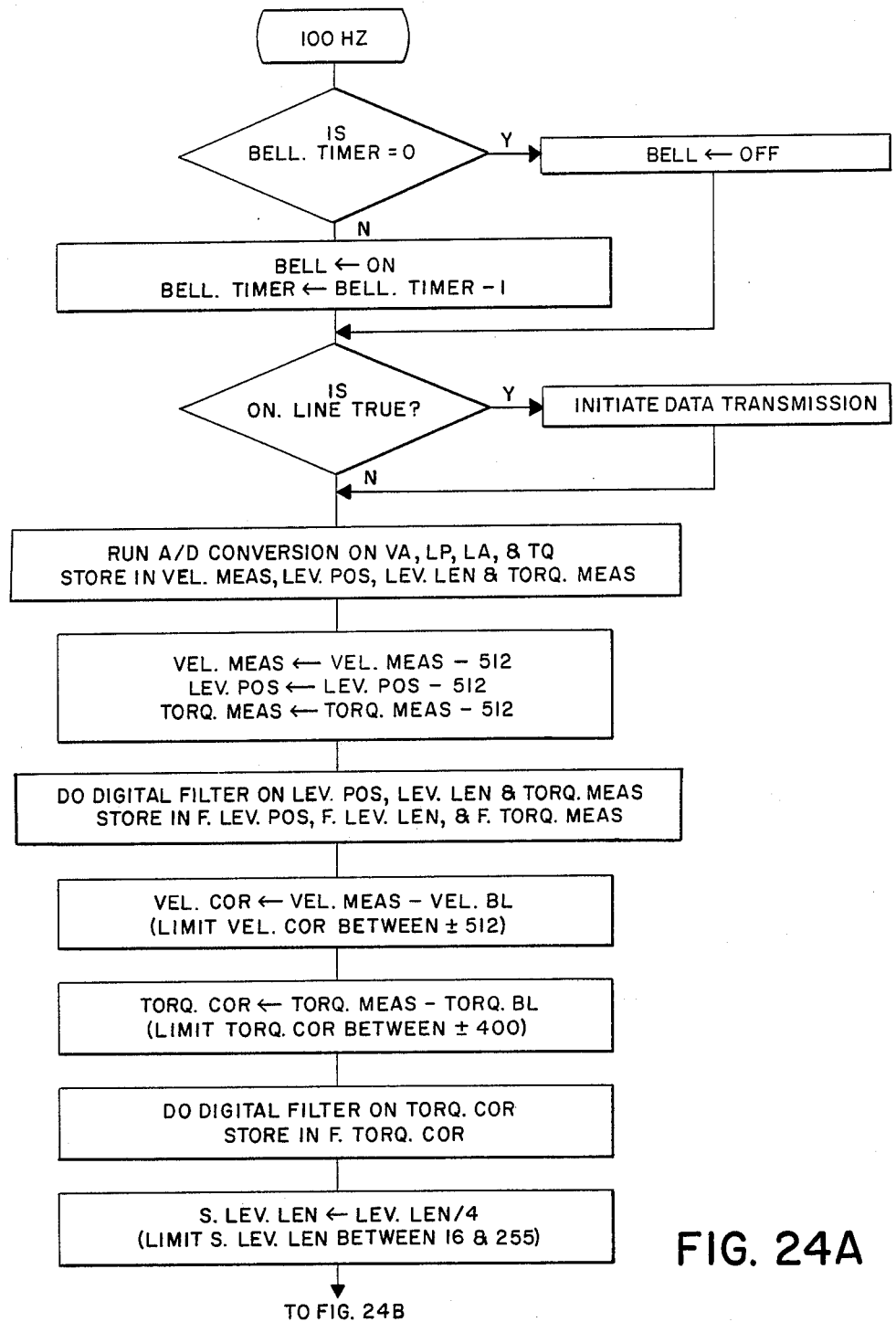
Figure 24B:
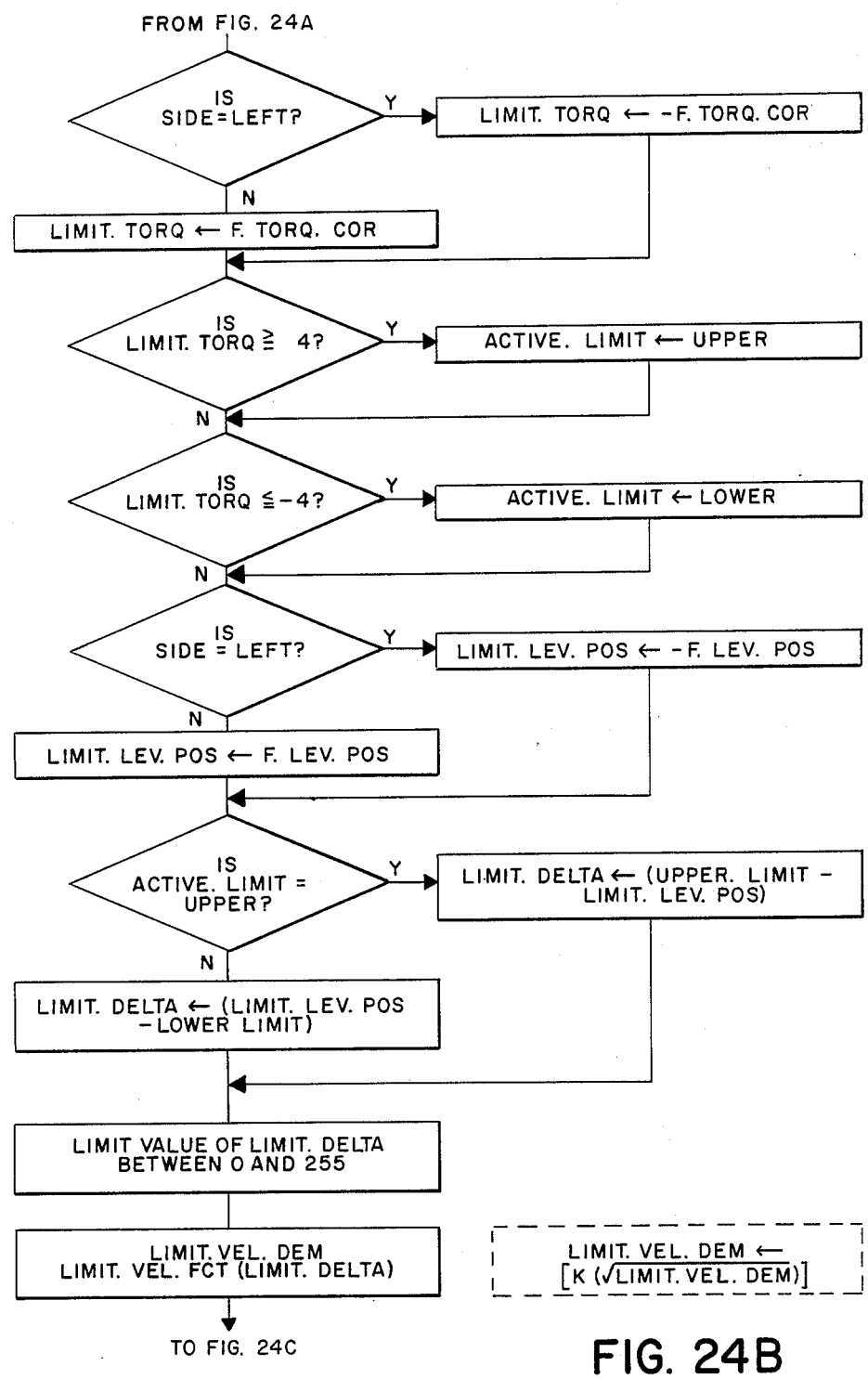
Figure 24C:
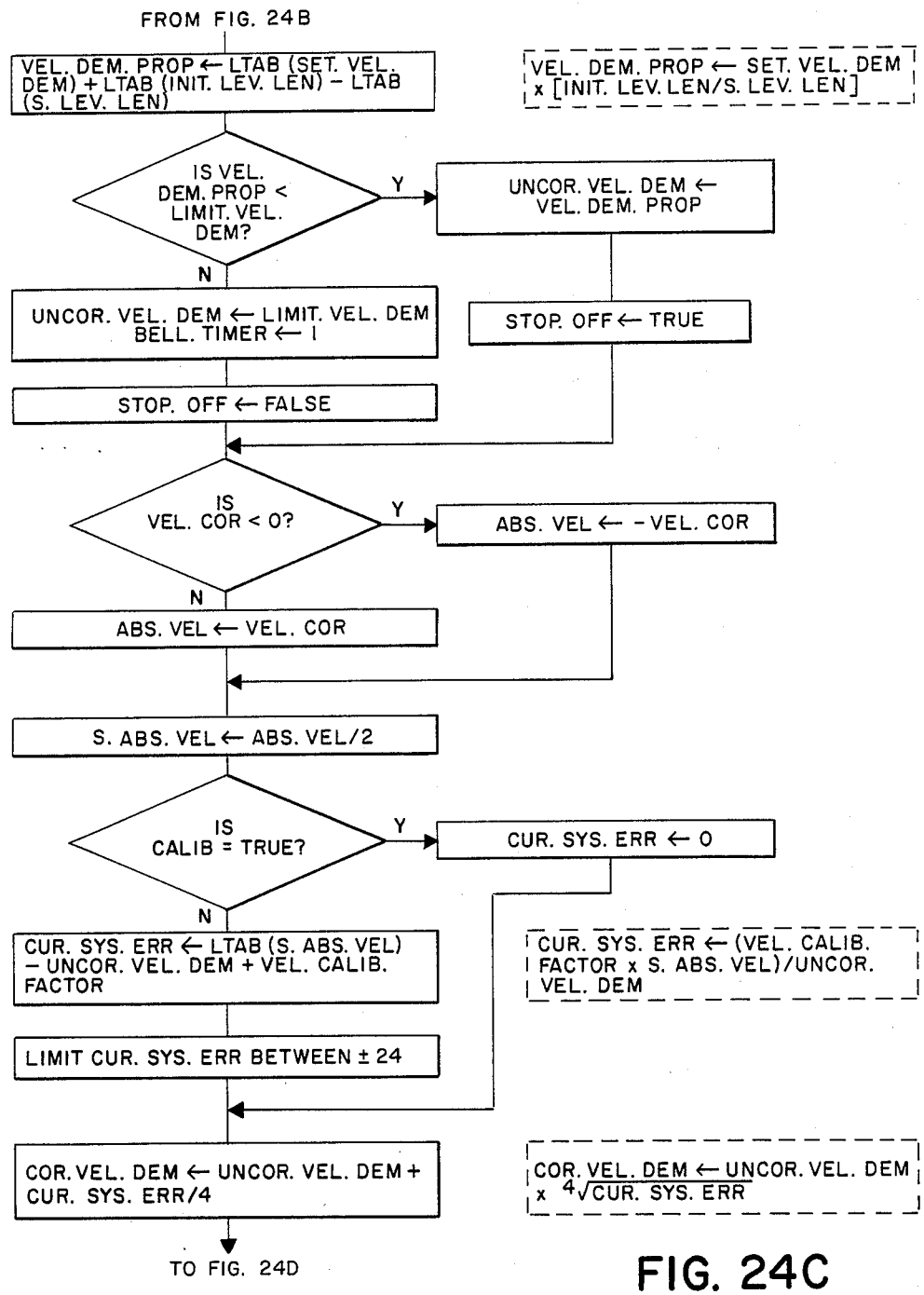
Figure 24D:
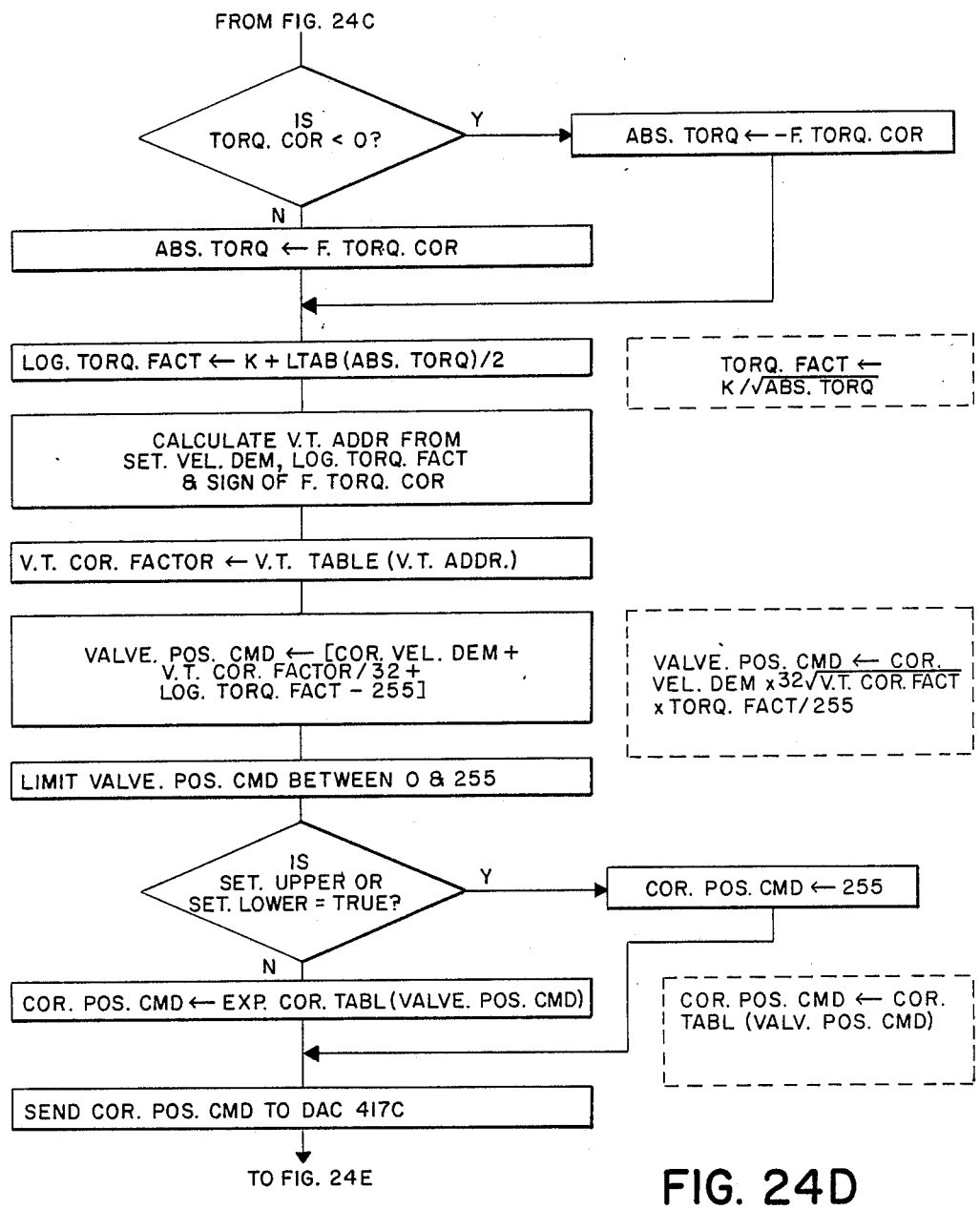
Figure 24:
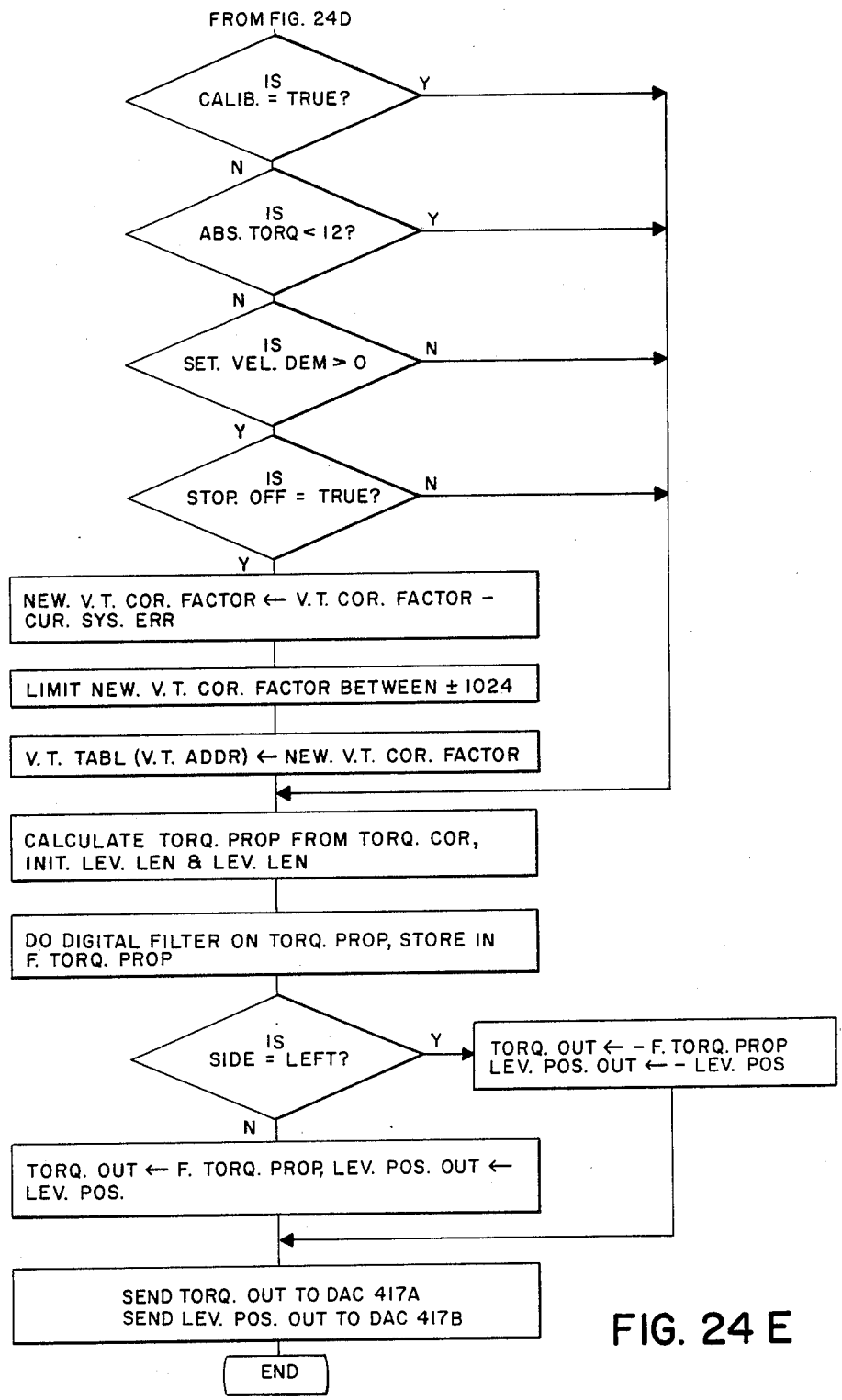

The 100 Hz interrupt routine is depicted in FIGS. 24A–24. Referring first to FIG. 24A, the first steps of the routine involve a bell sounding function. At other places in this routine or in other interrupt routines, a parameter called BELL.TIMER may be set to a certain value based on the number of times at the 100 Hz frequency of execution of the 100 Hz routine that a signal should be sent to a bell or buzzer by the computer. Thus the first step of the 100 Hz routine is a checking step to determine if BELL.TIMER is zero. If this checking step returns a YES value, the BELL parameter is set OFF so that the bell or buzzer will not sound. If this checking step returns a NO value, the BELL parameter is set to ON so that the bell will sound. Also the BELL.TIMER parameter is decremented by one to count down the number of times that the bell is to be sounded.

What actually happens with setting the value of the BELL parameter ON is that this parameter is later used in an assembly language routine which is called during the time that analog to digital conversion is being performed on inputs. During that analog to digital conversion routine, data word values are sent to the latches 423 shown in FIG. 20B. One of the latches has an output to a buzzer and that latch value will be set ON to sound the buzzer if the BELL parameter is ON. If the BELL parameter is OFF that latch will not be set and the buzzer will not sound.

The next step in the 100 Hz routine is a checking step to determine whether the ON.LINE parameter is set TRUE or not. This is a data register value which is set by other routines to signal whether data transmission should be performed. If the checking step returns a YES, a data transmission routine is initiated. This data transmission routine runs at a higher interrupt level and interrupts the 100 Hz routine every time it needs to perform certain of its functions and then releases the computer to continue with execution of the 100 Hz routine.

The next step in the 100 Hz routine is to do the analog to digital conversion of the analog inputs. As previously mentioned, this is done in an assembly language routine which sends a series of data and control signals to the latches and the analog to digital converter shown in FIG. 20B to sequentially convert all of the input analog signals to digital data values and store them in registers in the computer designated LEV.POS, TORQ.MEAS, LEV.LEN and VEL.MEAS. Following this, the VEL.MEAS, LEV.POS, and TORQ.MEAS signals are made bipolar by subtracting 512 (one half full scale). This is followed by running a digital filter routine on LEV.POS, TORQ.MEAS and LEV.LEN. Digital filtering is a standard software routine which basically involves storing multiple sequential values of these parameters in data arrays, adding the multiple stored parameter values together and dividing by the number of parameters stored. For example, eight values may be stored and the total sum of the eight values divided by eight to get the filtered digital word value. This digital filtering routine filters out some of the noise which is otherwise present in the digital word values due to noise which may be present in the analog signal processing circuitry.

(a) Baseline Correction on Velocity and Torque

The next sequence of steps in the routine perform baseline correction on the velocity values and torque values and maintains those values within prearranged limits. To obtain the baseline corrected velocity value the parameter VEL.COR is set to the value of VEL.MEAS minus the value of VEL.BL. VEL.BL is the value of the velocity baseline correction which is determined in the 6.25 Hz routine when the lever arm is not moving. Velocity baseline errors can occur due to errors in the analog circuitry or in the analog to digital conversion process. The purpose of performing this step is to make the measured velocity signal more accurate since later on in the routine the VEL.MEAS signal will be used to determine a system error in parameter. Thus it is preferable to normalize out of the measured velocity value any velocity baseline errors which are detected in the system by the software. The next step in the routine is to limit VEL.COR to be within the maximum limits of +512 and −512.

The next step is to do a torque baseline correction by subtracting the TORQ.BL value from TORQ.MEAS and setting the result in TORQ.COR. Following this TORQ.COR is limited to its upper and lower limit values of +400 and −400 and then filtered and stored in F.TORQ.COR.

The next steps of the routine involve performing a scale change on LEV.LEN to bring it within the range of values needed in later calculation steps and then limiting that adjusted lever arm length to a certain minimum value. Accordingly, the next step is to calculate the value of LEV.LEN divided by four and then setting that as S.LEV.LEN value representing "Scaled LEVer LENgth". Following this, a checking step is performed to determine whether S.LEV.LEN is less than 32. If this checking step returns a YES value, S.LEV.LEN is set to a predetermined minimum value, in this case 32.

(b) Determining a Limit Velocity Demand Signal LIM.VEL.DEM Based on the Active Limit and the Current Lever Arm Position The next portion of the 100 Hz routine is shown in FIG. 24B and involves determining a limit velocity demand value based on the current position of the lever arm relative to the currently active one of the UPPER.LIMIT and LOWER.LIMIT. To understand the steps of this portion of the routine, some conventions which have been adopted for the system need to be discussed. Referring back to FIG. 18, it should be understood that the pressure transducers 110 and 111 are coupled into the torque computer in a manner such that the analog torque output value will be positive if the lever arm is moving clockwise and will correspondingly be negative if the lever arm is moving counterclockwise.

Referring to the limits setting switches on the control panel 300 shown in FIG. 17, the UPPER LIMIT and LOWER LIMIT stop settings are, for convenience of the user, independent of whether the lever arm is moving counterclockwise toward the upper limit or clockwise toward the lower limit. If the patient is exercising the right side and RIGHT is set into the system using the SIDE button, then clockwise motion will be towards the UPPER LIMIT and counterclockwise motion will be toward the LOWER LIMIT of the lever arm. On the other hand, if the left side of the body is being exercised, the movement of the lever arm toward the upper limit is counterclockwise and the movement of the lever arm toward the lower limit set is clockwise. Accordingly, to properly sort out signal polarities relative to the side of the body being exercised and for maintaining correlation with the limit settings, torque and lever position signals must be inverted in sign when the side switch is set to LEFT, since all of the calculations in the software are based on the right side being the default side. When side is set to LEFT, the UPPER LIMIT and LOWER LIMIT values are inverted in sign when the settings are input and read in the 6.25 Hz routine.

(b.1) Determining the Active Limit

For purposes of an illustrative discussion of the section of this routine for determining a value for LIM.VEL.DEM, it will be assumed first that the SIDE mode is set to RIGHT. Thus the checking step to determine whether SIDE is equal to LEFT will return a NO value and LIMIT.TORQ will be set to F.TORQ.COR. The next two checking steps in the routine are used to determine the direction that the lever arm is moving relative to the upper and lower limits and thus which limit is the currently active limit. If LIMIT.TORQ has a positive value greater than or equal to 4, this means that the lever arm is moving toward the upper limit set and the value of ACTIVE.LIMIT is set to UPPER. On the other hand, if LIMIT.TORQ has a negative value less than or equal to −4, this means that the lever arm is moving toward the lower limit set and the value of ACTIVE.LIMIT is set to LOWER. If the value of LIMIT.TORQ is between +4 and −4, this means that the lever arm is in a turn-around state after reaching one of the limits or is stationary and is not moving toward either of the limits. Thus there is hysteresis in the value of ACTIVE.LIMIT, i.e. its value is not changed until there is a reversal in the polarity of the LIMIT.TORQ signal and the magnitude of the LIMIT.TORQ signal has increased to the point that is is clear that the arm is being urged actively toward the opposite limit position. The torque value of +4 and −4 is not critical and can be set to a value in the range of +/−1 to +/−10.

The overall cycle is as thus as follows. With SIDE set to RIGHT, and assuming that the exercise motion begins by movement toward the upper limit, the value of LIMIT.TORQ will be set to TORQ.COR as a result of the first checking step. The second checking step will return a YES value and ACTIVE.LIMIT will be set to UPPER. As will later be seen, when the UPPER.LIMIT setting of the lever arm position is approached, the velocity demand signal is reduced toward zero value so that the upper limit is not exceeded by the patient. As the patient experiences the increased resistance to movement of the lever arm (and a sounding of the buzzer to warn audibly of the approach to the limit), the patient will stop pushing the arm toward the upper limit and the value of F.TORQ.COR will drop toward 0.

Assume that during the next execution of the 100 Hz routine, the value of F.TORQ.COR is still at 0. The value of LIMIT.TORQ will be 0 and the first and second checking steps related to the value of LIMIT.TORQ will both return NO values. Thus there will be no change in the setting of ACTIVE.LIMIT. However, as the patient begins pulling the lever arm away from the position corresponding to the value of UPPER.LIMIT, the polarity of the F.TORQ.COR signal value will change to negative and build up rapidly to value exceeding 4 (foot pounds). Thus during some subsequent execution of the 100 Hz routine, LIMIT.TORQ will have a substantial negative value, the first checking step will return a NO value, but the second checking step will return a YES value. As a result, ACTIVE.LIMIT will be set to LOWER, indicating that the now active limit is the lower limit.

If the left side of the body were being exercised, the inversion of the F.TORQ.COR value in setting the LIMIT.TORQ value keeps the LIMIT.TORQ value positive when the UPPER.LIMIT is the ACTIVE.LIMIT and keeps the LIMIT.TORQ value negative when the LOWER.LIMIT is the ACTIVE.LIMIT. It should be appreciated that there are other ways that the 100 Hz routine could determine the active limit. For example the sign and value of VEL.COR could be used in substantially the same way that TORQ.COR is used. The LEV.POS signal could also be used by executing a routine that determines when the lever arm has reversed direction based on a change in the direction of alteration of its value from one execution of the 100 Hz routine to the next. It is important, however, that the determination of the currently active limit be done accurately so that the LIM.VEL.DEM signal will be accurately calculated.

(b.2) Calculating the LIMIT.DELTA Value

After the checking steps for determining the active limit have been executed, the checking step to determine whether SIDE is LEFT is again executed to determined whether the value of the LEV.POS signal must be inverted for the proper calculation of the LIMIT.DELTA value. If this checking step returns a YES value, LIMIT.LEV.POS is set to −LEV.POS. Otherwise, LIMIT.LEV.POS is set to LEV.POS. Following this a checking step is provided to determine whether the value of ACTIVE.LIMIT is UPPER. If this returns a YES value, LIMIT.DELTA is set to the value of UPPER.LIMIT minus LEV.POS. Otherwise LIMIT.DELTA is set to the value of LIMIT.LEV.POS minus LOWER.LIMIT. Then the value of LIMIT.DELTA is limited to be between 0 and 255. Finally, LIM.VEL.DEM is determined from a lookup table using LIMIT.DELTA as the address to obtain a value from the LIMIT.VEL.FCT table.

The LIMIT.VEL.FCT table is set up so that LIMIT.VEL.FCT (LIMIT.DELTA) is equal approximately to the logarithm of the square root of a constant times the value of LIMIT.DELTA. The log value is used because this parameter will later be used in a calculation using log arithmetic for multiplication and division. If log arithmetic were not later used, the table would have values approximating the square root of a constant times the value of LIMIT.DELTA. The actual table values for LIMIT.VEL.FCT are given in Table 1. A graph showing the relation between LIMIT.DELTA and LIMIT.VEL.FCT(LIMIT.DELTA) is given in FIG. 25. (obtain Table 1 and FIG. 30A. LIMIT.VEL.FCT is basically the square root of LIMIT.DELTA times a constant. Thus as shown in the dashed rectangle, this value could be calculated as an alternative to using a look up table. The look up table is preferable when the system does not have a fast processor available to do complex math functions.

Referring to FIGS. 25A and 25B, the lever position limiting function of this section of the software is illustrated and will be described. FIG. 25A illustrates the parameters that are involved when the SIDE switch is set equal to RIGHT and FIG. 25B illustrates the parameters when the SIDE switch is set equal to LEFT. In the 6.25 Hz routine, the upper and lower limit values are set utilizing the upper and lower limit pushbuttons on the control panel. As shown in FIG. 25A the zero position for the lever arm is straight down for purposes of this example Excursions of the lever arm counterclockwise produce negative values of the lever position signal F.LEV.POS, whereas clockwise excursions produce positive values Assume that the SIDE switch is set equal to RIGHT. During the setting of the upper and lower limit values (by positioning the lever arm at the desired limit value and depressing the corresponding pushbutton), the lever position values present at the pushbutton switch are directly read without inversion Accordingly the UPPER.LIMIT value has a positive number and the LOWER.LIMIT value has a negative number as shown in the example in FIG. 25A.

Referring back to the flow chart in FIG. 24B, if the checking step regarding whether SIDE is equal to LEFT returns a NO value, then the LIMIT.LEV.POS signal is set to the filtered lever position signal F.LEV.POS The result of the checking step as to whether the ACTIVE.LIMIT is UPPER determines whether the LIMIT.LEV.POS position is subtracted from the UPPER.LIMIT or has the LOWER.LIMIT value subtracted from it. Referring to FIG. 25A, if the lever arm is moving toward the upper limit so that ACTIVE.LIMIT is equal to UPPER, the LIMIT.DELTA value representing the difference between the upper limit value and the lever position is obtained by subtracting the upper limit value from the current lever position. Similarly, if the lever arm is moving counterclockwise toward the active lower limit, the subtraction of the higher value LOWER.LIMIT from the negative value of the LIMIT.LEV.POS signal produces a LIMIT.DELTA value which is a positive number. Thus the LIMIT.DELTA value is always an absolute value (i.e. always a positive number) representing the angle difference between the lever arm and the currently active limit.

Referring to FIG. 25B, when the SIDE switch is equal to LEFT the upper and lower limit values set by the pushbuttons are inverted so that the UPPER.LIMIT value which corresponds to a negative lever arm position is inverted to a positive number. Similarly, the LOWER.LIMIT value which is corresponds to a positive position of the lever arm is inverted to a negative value. This makes the algorithm for calculating the LIMIT.DELTA a correct one, since the LIMIT.LEV.-POS signal represents a negative version of the F.LEV.POS signal when the SIDE button is set equal to LEFT. This makes the arithmetic work out correctly for either side being exercised.

(c) Determining a Corrected Velocity Demand Signal (c.1) Proportioning the Velocity Demand Signal FIG. 24C illustrates the portion of the 100 Hz routine which involves determining a corrected velocity demand signal designated COR.VEL.DEM. The first step of this portion of the routine is to obtain a proportioned velocity demand signal designated VEL.DEM.PROP, by multiplying SET.VEL.DEM by the ratio of INIT.-LEV.LEN and LEV.LEN. This could be done in the computer by actually doing multiplication and division routines, but this takes substantial processor time unless a high speed math coprocessor is used.

To save processor time and make the execution of the 100 Hz routine as fast as possible, the multiplication and division is done using logarithms. This permits multiplication to be done by addition of log values and division to be done by subtraction of log values. The log values are obtained from a simple lookup table LTAB having 255 values stored in it. The values are shown in Table 2 and the shape of the log function is shown in FIG. 30B.

Thus the next step of the 100 Hz routine as shown in FIG. 24C is to look up the values of SET.VEL.DEM, INIT.LEV.LEN and LEV.LEN in the log table LTAB and then to set the value of VEL.DEM.PROP using the equation shown in FIG. 24C.

(c.2) Selecting the Minimum of VEL.DEM.PROP and LIM.VEL.DEM

The next steps of the routine set the uncorrected velocity demand signal to be the minimum of VEL.-DEM.PROP and LIM.VEL.DEM. The checking step determines whether VEL.DEM.PROP is less than LIM.VEL.DEM and if a YES value is returned, UNCOR.VEL.DEM is set to VEL.DEM.PROP. Otherwise UNCOR.VEL.DEM is set to LIM.VEL.DEM and BELL.TIMER is set to 1 so that the bell will ring at the beginning of the next execution of the 100 Hz routine. This indicates to the person exercising that the active limit has been reached.

(c.3) Calculating the Current System Error

It will be remembered that, in the analog signal computation version of this invention, the current system error was factored into the velocity demand signal in two ways. The first way involved developing a fast correction based on subtracting the absolute value of the measured velocity of the system from a signal value representing twice the value of the proportioned velocity demand. Thus the difference between the value of VDP and the absolute value of absolute V which is a measure of the current system error in velocity is taken into account in developing a corrected velocity demand signal VDC. Also a slow correction signal is developed by adding into VDC a small fraction of the integrated system error value determined from the difference between VDP and the absolute velocity value.

In the digital computation embodiment, a somewhat different approach is taken to incorporating the current system error into the velocity demand signal. In this case the current system error is expressed in the form of a ratio of the absolute value of measured velocity multiplied by a velocity calibration to increase accuracy and the uncorrected velocity demand signal. The function of and calculation of this velocity calibration factor will be discussed in detail below.

Since one of the factors used in determining the current system error is the absolute value of the measured velocity, the next group of steps in the routine determine the absolute value of the VEL.COR parameter. This is done by first executing a checking step to determine if VEL.COR is negative. If a YES value is returned, ABS.VEL is set to −VEL.COR. Otherwise ABS.VEL is set to VEL.COR. Next a scale change is made in ABS.VEL by dividing it by two and setting it into S.ABS.VEL.

The next checking step determines whether the value of CALIB was set TRUE during execution of the MAIN routine on power up. If a YES value is returned, CUR.SYS.ERR is set to 0 so that it will not affect the calibration performed on the system and a series of steps of the program are bypassed. During normal operation of the system, the CALIB flag will not be TRUE. Thus the routine will continue by calculating the current system error designated CUR.SYS.ERR. This is also done with log values. The basic equation is

CUR.SYS.ERR=(VEL.CALIB.FACTOR)×-S.ABS.VEL)/UNCOR.VEL.DEM.

When this is done in logarithms, the equation is as shown in FIG. 24C, remembering that UNCOR.VEL.-DEM is already a log number and PRIOR.VEL.ERR is calculated during the 6.25 Hz routine as a log number.

(c.4) Calculating Corrected Velocity Demand

The routine then limits the value of CUR.SYS.ERR to be between +24 and −24 and then determines a COR.VEL.DEM signal value by adding ¼ of the CUR.-SYS.ERR value to the value of UNCOR.VEL.DEM. Remembering that log values are being used here, this is equivalent to multiplying UNCOR.VEL.DEM by the fourth root of the CUR.SYS.ERR. In other words the mathematical calculation for COR.VEL.DEM as a function of UNCOR.VEL.DEM and CUR.SYS.ERR is shown in the dashed rectangle opposite:

(d) Determining a Value Position Command Signal For the Flow Control Valve (d.1) Determining the Torque Factor The next portion of the 100 Hz routine is shown in FIG. 24D and involves the program steps for determining a corrected position command signal for the flow control valve. The basic algorithm used in this digital computer implementation is the same as that used in the analog computation implementation discussed above. Thus the basic predictive function is used and the corrected velocity demand signal is multiplied by a torque factor which is basically a predetermined constant divided by the square root of the absolute value of the measured torque. The corrected velocity demand signal is in log form as calculated in this embodiment. Thus, as will be discussed below, it is convenient to use log arithmetic to multiply by the torque factor of the predictive function. To simplify and speed the processing, the value of LOG.TORQ.FACT is calculated using the logarithm equation

LOG.TORQ.FACT=K+LTAB (ABS.TORQ)/2.

The constant K is 1275 for this case but might be different for other designs of actuators and flow control valves.

In addition, in this digital computation embodiment, an additional correction factor is preferably incorporated into the predictive function to increase the accuracy of the position command signal. This additional factor is an actual system experience correction factor which is built up over time that the system is actually being used.

(d.2) Determining a Velocity/Torque Correction Factor

The use of digital computer technology permits the actual system errors which are computed by the software to be used as inputs to an experience table which is stored in memory. The two factors which are used in the predictive function are velocity demand and measured torque. For best results it is preferable to construct the experience table as a two dimensional array of data points with one of the two dimensions being related to torque and the other being related to velocity demand. Since in this particular embodiment of the invention, the mathematical computations are done in logarithms, it is convenient to declare one of the dimensions of the array as the LOG.TORQ.FACT. It is also convenient to declare the other dimension of the array as SET.VEL.DEM.

The number of data points which are used in each dimension may be chosen on the basis of several factors including the fineness of resolution desired on the correction function relative to two dimensions and the amount of memory that is available to be devoted to storage of the array. In this embodiment, both the LOG.TORQ.FACT and SET.VEL.DEM parameters take on values which are limited to be between 0 and 255. It has been determined that a good working number of data points for the array is 32×32 for each direction of movement of the lever arm. This means that the correction factor stored at each location is shared by eight possible values of each of the parameters LOG.TORQ.FACT and UNCOR.VEL.DEM.

At each of the data points in this array, an experience correction factor is accumulated based on updating the data value stored in the active data point each time the 100 Hz routine is executed. The active data point is addressed based on the values of LOG.TORQ.FACT and SET.VEL.DEM which are calculated. The updating is done by adding to the value stored at the active data point the value of CUR.SYS.ERR as earlier determined by the software routine Prior to the updating of the data point value, the previously stored value is read and used in the predictive function calculation in a manner which will be described below. The actual value read is not used, but is divided down by a psuedo-averaging factor to limit the effective gain of this correction factor.

It should thus be apparent that, over a period of time of actual operation of the exercise system of this invention, the data value stored in each location of the array will gradually accumulate a value which indicates the magnitude of average system error actually experienced by the system when the related torque and velocity demand values were present. This then becomes an effective correction factor which will increase the accuracy of the valve position command signal when incorporated into the predictive function calculation. Moreover, this correction factor will slowly track changes in the system errors that occur due to changes in environmental or other factors which affect the system performance, such as temperature changes in the hydraulic fluid in the actuator system which affect the torque factor in the predictive function.

The actual steps executed in one embodiment of a software routine for implementing this feature will now be described with reference to FIG. 24D. The initial steps of this portion of the routine determine the absolute value of TORQ.COR and sets it into ABS.TORQ. Then the value of ABS.TORQ is used to look up a value in a table called LTAB for use in calculating LOG.TORQ.FACT.

The next step involves calculating an address value VT.ADDR based on SET.VEL.DE14, LOG.TORQ.FACT and the sign of F.TORQ.COR for locating the appropriate active data point in the V.T.TABL array. This data value stored in V.T.TABL[VT.ADDR] is then read and set into a parameter designated V.T.CORR.FACTOR. Then the value of VALVE.POS.CMD is computed in accordance with the math equation shown in FIG. 24D. Remembering that this is done in log arithmetic the equation actually implemented is

VALVE.POS.CMD=COR.VEL.DEM+V.T.CORR.FACTOR/32+LOG.TORQ.FACT-255 with the subtraction of 255 in the log arithmetic version being a scale adjustment factor. The non-log math version is shown in the drawing figure. Following this log arithmetic step, the final calculated value of VALVE.POS.CMD is limited to be a value between 0 and 255.

(e) Determining a Corrected Valve Position Command

The next portion of the software routine involves determining a corrected position command signal to be converted back to an analog signal value to send to the error summing circuit for actual control of the valve position. However, first a checking step is performed to determine if the user is currently in the process of setting one of the upper or lower limits. The SET.UPPER and SET.LOWER values are determined during the 6.25 Hz routine and become TRUE where the corresponding limit pushbutton is depressed. When either of the pushbuttons for setting UPPER.LIMIT or LOWER.LIMIT is depressed, the checking step will return a YES value and the COR.POS.CMD parameter will be set to its maximum value of 255 which corresponds to a wide open valve setting. This is done so that the lever arm will be totally unrestricted in its movement during the limits setting operation. During normal exercise on the system, this checking step will return a NO value.

The COR.POS.CMD parameter will then be determined by looking up its value in a table designated EXP.COR.TABL using VALVE.POS.CMD as the address of a data point in the table. The data values stored in this table convert the log value of COR.-POS.CMD back to the binary equivalent of a decimal number and apply a prearranged correction factor based on the known non-linearity of relationship between COR.POS.CMD values and appropriate actual valve position command signals. The data stored in EXP.COR.TABL is given in Table 3 and the functional relationship is illustrated in the curve of FIG. 30C. After the COR.POS.CMD is obtained, it is sent to the appropriate digital to analog converter for input to the error summing circuit to control the valve position setting.

(f) Updating V.T.TABL Based On CUR.SYS.ERR

The following portion of the software routine involves updating the stored value in the V.T.TABL provided certain conditions in the four successive checking steps shown are satisfied. Updating of V.T.TABL is bypassed if the value of CALIB has been set TRUE or if the value of ABS.TORQ is less than 12 or if the value of SET.VEL.DEM is not greater than 0. It is also bypassed if STOP.OFF does not have a TRUE value.

During calibration of the system, there is no need to update the V.T.TABL data point. Also, it is preferable to bypass updating of the V.T.TABL under conditions of very low torque and zero demand velocity. Updating should also be bypassed if the lever arm is being pushed against an active limit.

When the update step is performed on V.T.TABL, it involves subtracting the value of CUR.SYS.ERR from the currently stored value at the active data point in the table. This may be done with one command in the software routine, but conceptually, this is most easily understood by considering the process to involve the following steps. First, a new correction factor designated NEW.VT.COR.FACTOR is determined by subtracting the value of CUR.SYS.ERR from the value of VT.COR.FACTOR. Then NEW.VT.COR.FACTOR is limited to have values between +1024 and −1024. The purpose of this is to place some practical limits on the size of the correction factor. The final step is to store the value of NEW.VT.COR.FACTOR in V.T.TABL at the address specified by VT.ADDR.

The reason for setting new correction factor based on subtracting the current system error from the stored value is that CUR.SYS.ERR is a log value and a subtraction of this log value is equivalent to dividing or multiplying in normal arithmetic depending on the sign of CUR.SYS.ERR. If CUR.SYS.ERR is a positive number, this means that the measured velocity ABS.VEL corrected by the velocity calibration factor VEL.CALIB.FACTOR is greater than the uncorrected velocity demand UNCOR.VEL.DEM and the value of VALVE.POS.CMD should be reduced to decrease the value opening the next time these same operating conditions of torque and velocity demand are encountered. The correction factor stored in V.T.TABL for the active data point should correspondingly be reduced since its value is additive in the equation for determining VALVE.POS.CMD.

The opposite is true if the value of CUR.SYS.ERR is negative. This condition will occur when the value of (ABS.VEL×VEL.CALIB.FACTOR) is less than the uncorrected velocity demand. In this case, the value of VALVE.POS.CMD should be increased the next time these same operating conditions are encountered. Subtracting the value of CUR.SYS.ERR when it is negative, increases the value stored at the active data point in the V.T.TABL and this will have the effect of increasing the value of VALVE.POS.CMD the next time this data point is actively involved in calculation of that parameter.

(g) Determining the Output Analog Signals for Torque and Lever Position

After the correction factor update steps are performed, the final section of the 100 Hz routine determines the appropriate output analog signals for the torque and lever position first, a proportioned torque value is determined and set into parameter TORQ.-PROP based on the values of INIT.LEV.LEN and LEV.LEN. This can be performed using the same log arithmetic that was used to proportion the velocity demand signal as described above.

After determining the value of TORQ.PROP, the value is filtered and the appropriate values of the analog output signals for torque and lever position are determined based on the setting of the SIDE mode switch. A checking step is performed to determine whether SIDE=LEFT, and if this returns a YES value, then TORQ.OUT and LEV.POS.OUT are set by inverting F.TORQ.PROP and LEV.POS, respectively. If the checking step returns a NO value, then TORQ.OUT and LEV.POS.OUT set equal to F.TORQ.PROP and LEV.POS, respectively.

The final step of the 100 Hz routine is to send TORQ.OUT and LEV.POS.OUT to their respective dedicated digital to analog converters to generate the corresponding analog signal values to be coupled to analog display and/or chart recording system components. The digital values are sent to a remote computer in the data transmission routine.

(h) The Valve Position Command Algorithm

FIG. 26 illustrates the shape of the valve position command signal as a function of velocity demand and torque. As shown in FIG. 26, there are a family of valve opening versus velocity demand curves which depend on the actual torque value experienced by the system. When the torque value is large, the slope of the curve which represents valve opening versus velocity demand is smaller than it is at smaller torque values.

Referring now to FIG. 24E and the discussion of the velocity torque correction factor designated V.T.COR.FACTOR, as previously explained, the velocity torque correction table array provides a two-dimensional correction factor on valve opening at each of a number of torque and velocity set points. Thus this correction table can be viewed as superimposing on the topography of the valve opening versus torque and velocity shape shown in FIG. 26, localized undulations in that curve which are tracked and corrected based on actual system experience with the valve opening that is correct for that particular combination of torque and velocity.

For example these correction values may be stored in a 32×32×2 matrix array. As discussed above in connection with the software flow chart shown in FIG. 24E, these velocity/torque correction factors are updated based on the current system error. Thus the velocity torque correction factors provide an overlay of variation in the valve opening command value for each region of torque and velocity based on actual system experience. The system thus learns what the valve opening command should be at various regions of torque and velocity demand parameters so that the system effectively teaches itself based on recent experience what the appropriate valve opening algorithm should be for accurate control.

Another software routine that is running in the system is a smoothing algorithm that runs in BACKGROUND routine to avoid too large a difference between the velocity torque correction factor between one region of the table and another. It is preferable in accordance with this invention that the velocity/torque correction factor that is obtained be addressed on the basis of the set velocity demand so that the same area of the table of velocity torque correction factors will be addressed and updated based on system experience. The smoothing function is still important in case the torque parameter addresses a portion of the velocity/torque correction factor array which has not previously been addressed and which is possibly out of date in terms of the correction factors stored there. The smoothing of the table limits the difference between adjacent regions of the array and avoids the possibility of a sharp discontinuity in the correction factor in crossing the boundary between one region of the table and another.

(4) The 6.25 Hz Routine

As indicated above, this routine executes one time for each sixteen times of execution of the 100 Hz routine and it contains a number of individual modules which perform various functions. One of the modules involves control panel reading and display functions to acquire the control setting values that the user inputs into the control panel. This involves very straightforward routines to look at the state of the control buttons being pushed on the panel and to acquire control signal parameters based on the buttons pushed.

The control parameters which are obtained are SET.VEL.DEM, INIT.LEV.LEN, UPPER.LIMIT, LOWER.LIMIT, and SIDE. If more than one control mode, i.e. control modes in addition to the isokinetic mode to which this present explanation is limited, is available in the system software, then a MODE control parameter is also obtained through one of these control setting modules.

Because these control setting software modules are straightforward and they can be implemented in a number of different ways, they need not be described in detail here. In addition to the modules which obtain the control settings, there are two additional modules for obtaining the values of variable parameters which are used in the 100 Hz routine. The first is a routine for determining the value of VEL.CALIB.FACTOR which is used in the 100 Hz routine to determine the value of CUR.SYS.ERR. That routine is shown in FIG. 28, and will be described below.

Figure 29:
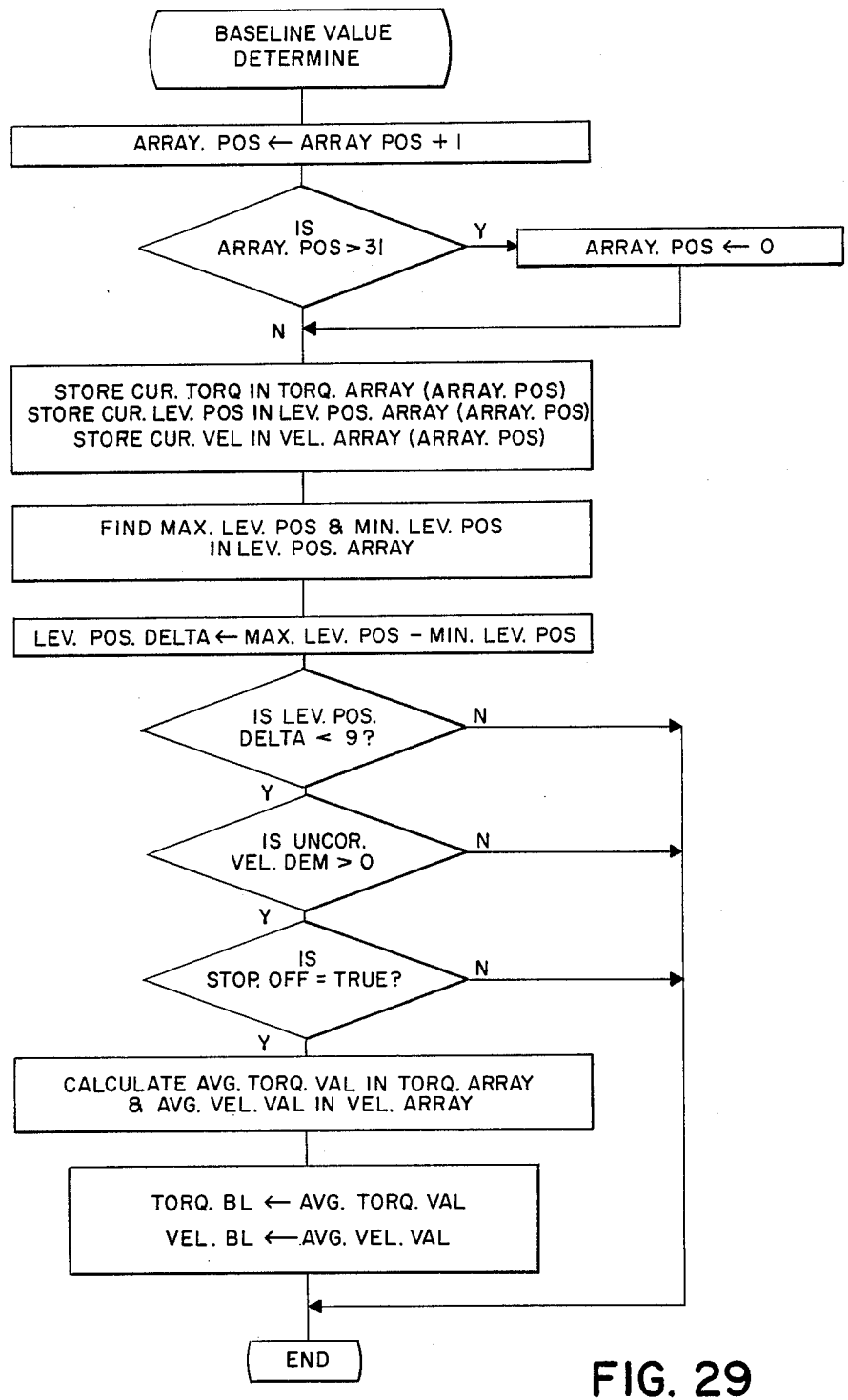

The second is a routine to determine the baseline correction factors for torque and velocity and to update the values of TORQ.BL and VEL.BL when the 6.25 Hz routine determines that the lever arm is not moving and hasn't moved for several times of execution of the 6.25 Hz routine so that baseline values can be determined. This routine is shown in FIG. 29, and will be described below.

(a) The PRIOR.VEL.ERR Routine

Figure 28:
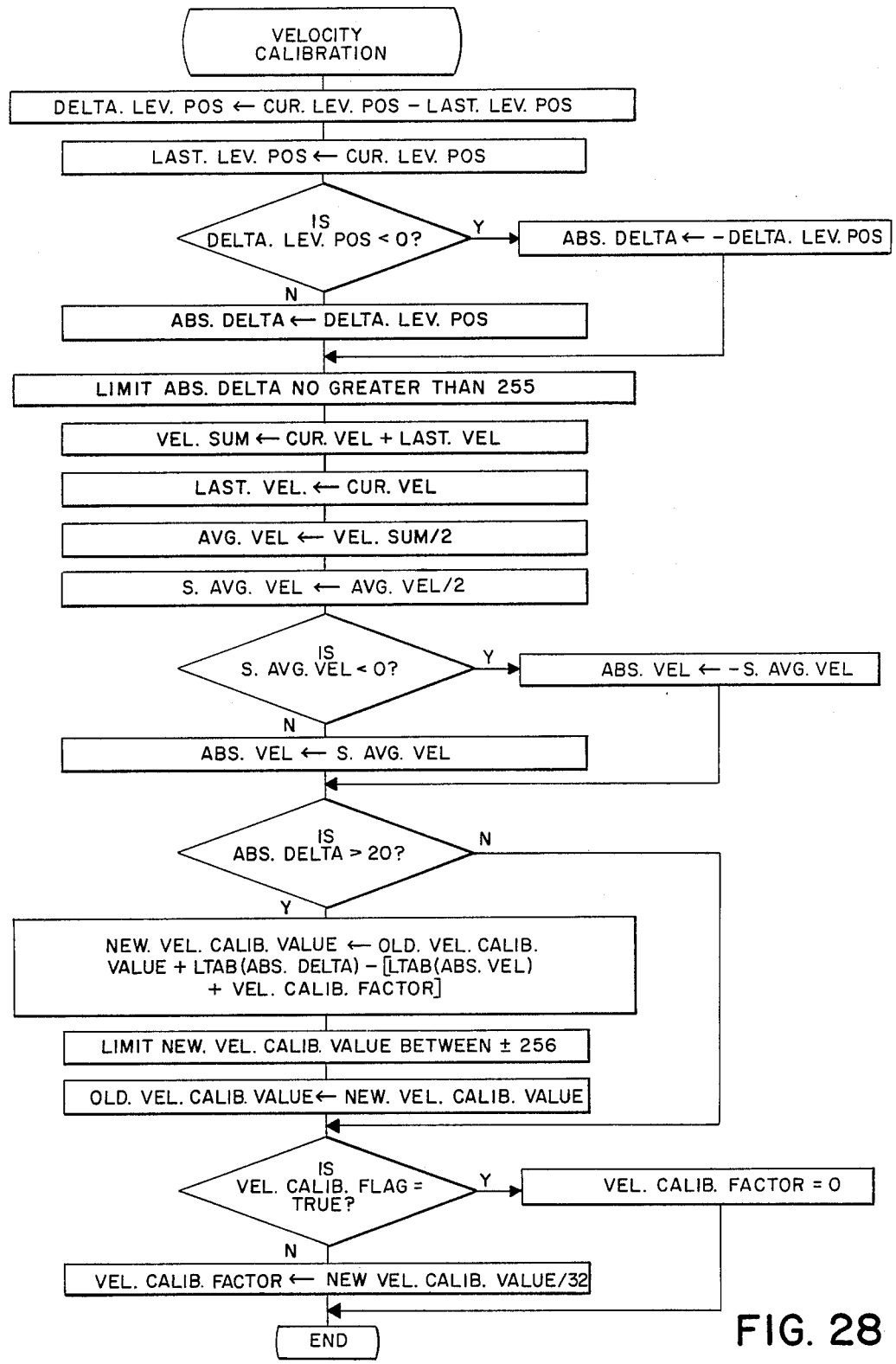
FIGS. 28 and 29 are software flow diagrams illustrating routines which are utilized in a programmed computer version of the system of this invention.

FIG. 28 illustrates a velocity calibration routine which is one of the software modules in the 6.25 Hz routine. The purpose of this routine is to provide a velocity calibration factor which is used in the 100 Hz routine as a calibration correction factor for the digital velocity signal which is obtained by doing analog to digital conversion on the actual velocity signal from the circuitry shown in FIG. 19A.

Referring back to FIG. 19A, it is seen that there is no trimming resistor provided for electrical calibration of the analog velocity signal. In addition, the resistors and capacitors that are utilized are not precision resistors and capacitors in order to provide a stable calibrated analog velocity. All of these techniques could be utilized, but the employment of a programmed digital computer control system provides the opportunity to do a continuously tracking velocity calibration which will take into account all elements of drift in the analog circuitry.

The basic concept involved in the velocity calibration routine shown in FIG. 28 is to determine the velocity of the lever arm based on the change in lever arm position from one execution cycle of this 6.25 Hz routine to the next. The change in position is a direct measure of velocity since the 6.25 Hz cycle executes on a regular timed basis. This measured actual lever arm velocity is ratioed with the velocity as measured through the analog to digital converter summed with the prior velocity calibration factor to produce a new velocity calibration value when multiplied by the old velocity calibration value. This is all done in FIG. 28 in logarithms, but the same approach could be utilized in straightforward mathematics. The velocity calibration values are used to derive a velocity calibration factor which is continually updated for use in the 100 Hz routine.

Referring to FIG. 28 and the steps of the routine specifically, the first step is to calculate a DELTA.LEV.POS as the difference between the current lever position and the last lever position. These parameters are designated CUR.LEV.POS and LAST.LEV.POS as shown in FIG. 28. Following this step the LAST.LEV.POS parameter is set to CUR.LEV.POS to be available the next time this routine is executed. Following this, the DELTA.LEV.POS parameter is made absolute and stored in a parameter designated ABS.DELTA. Then, as an optional step, this ABS.DELTA parameter is limited to be no greater than a value of 255.

The next portion of the routine determines an average velocity value as measured by the analog to digital conversion of the differentiated angular position signal for the lever arm. The parameters CUR.VEL and LAST.VEL are added together and stored in VEL.SUM. Following this, LAST.VEL is set to CUR.VEL for the next time the routine is executed. Then the parameter AVG.VEL is set to VEL.SUM divided by two. Following this a scale change is made by dividing AVG.VEL by two to get S.AVG.VEL representing a scaled average velocity. This scaled average velocity is then subjected to an absolute value routine to determine the value of ABS.VEL, being the absolute velocity value as measured by the differentiator circuit and the analog to digital converter.

Following this a checking step is performed to determine whether ABS.DELTA is greater than twenty. This corresponds to an actual measured velocity of forty degrees/second. If the ABS.DELTA value is less than that, it is not desirable to calculate a new velocity calibration value, since the lever arm is not moving very much and the accuracy of that new value may be suspect. If the system is in use and the absolute velocity is greater than forty degrees/second then the checking step will return a yes and a new velocity calibration value will be calculated using the algorithm shown in FIG. 28. This new velocity calibration value is then limited to be between plus and minus 256 for purposes of avoiding too drastic a change in the velocity calibration factor. Following this the old velocity calibration value is set to the new velocity calibration value so that it can be used the next time this routine is executed.

Next a check is made to determine whether the velocity calibration flag is true or not. This flag is set or not set in the main routine depending on whether a calibration of the system is to be made. If the velocity calibration flag is set true, the velocity calibration factor is set to zero and the resetting of the velocity calibration factor for use in the 100 Hz routine is bypassed. Otherwise, the value VEL.CALIB.FACTOR is set to 1/32 of the new velocity calibration value.

It will be appreciated that when the value of the velocity calibration factor is such that the velocity is measured by the change in angle and the velocity as measured by differentiating the change in angle and subjecting it to analog to digital conversion produces essentially the same velocity value, there will be no substantial change of the old velocity calibration value in setting the new velocity calibration value. At that time the velocity calibration factor to be used in the 100 Hz routine will be accurate and will provide the appropriate value to the algorithm for determining actual lever arm velocity for use i that routine. Then if the system starts to go out of calibration, the velocity calibration factor will automatically track any calibration as the velocity calibration routine executes on a regular basis.

The presence of the velocity calibration routine in the system and method of this invention is exemplary of the powerful, advantageous characteristics which can be achieved in a digital computer control system implementation. The system can maintain an intelligent learning environment for self-calibration purposes. This produces a system which behaves over a period of time much more accurately and precisely than a corresponding system without the same degree of intelligence.

(b) The Baseline Value Routine for Determining TORQ.BL and VEL.BL

FIG. 29 illustrates a baseline value determining routine which calculates the baseline values of torque and velocity so that these values can be subtracted out of the analog to digital converted values for eliminating baseline shift errors in the calculations. The concept which is implemented in the baseline value determining routine shown in FIG. 29 is to provide an array of thirty-two measurement value storage positions for torque lever position and velocity. Storage of the torque and velocity values for thirty-two readings is done for purposes of calculating average values of the stored parameter values in the array. The purpose of the storage in an array of thirty-two values of the lever position is to provide the ability to determine when the lever is not moving so a baseline error can be determined.

Each time the baseline value determining routine of FIG. 29 executes, a value of current torque, current lever position and current velocity is stored in the array at the next incremental array position. Following this, a routine is executed to determine the maximum lever position and the minimum lever position stored in the lever position array. Next a lever position delta signal is calculated by subtracting the minimum lever position from the maximum lever position.

Following the calculation of the lever position delta, three checking steps are executed to determine whether it is appropriate to calculate the torque and velocity baseline values. The first checking step determines whether the lever position delta value is less than nine. The parameter nine is selected empirically as a number which indicates that the lever arm is not really moving and hasn't moved substantially for at least the last thirty-two executions of the 6 Hz routine. This determines whether the lever arm has moved at all during the last two or three seconds.

If the first checking step returns a YES value, the second checking step is executed to determine whether the uncorrected velocity demand signal is greater than zero. This checking step is present to bypass the baseline calculation if the system is set to the point that the lever arm is not moving because of a stop position. Finally, a third checking step is executed to determine whether the value of STOP.OFF is true so that the baseline calculation will be bypassed if the lever arm is not moving due to the system encountering an upper o lower limit condition.

If all three checking steps produce a YES value, then the average torque value in the torque array and the average velocity value in the velocity array are calculated. Following this the torque baseline value is set to the average value and the velocity baseline value is set to the average velocity value. These baseline values are then used in the 100 Hz routine until this baseline value determining routine executes to change those values. If the lever arm is in a quiescent condition for a number of minutes or seconds this baseline value determining routine will execute a number of times and continuously reset the torque baseline until the lever arm starts moving again for an active exercise motion or other purposes.

Figure 27C:
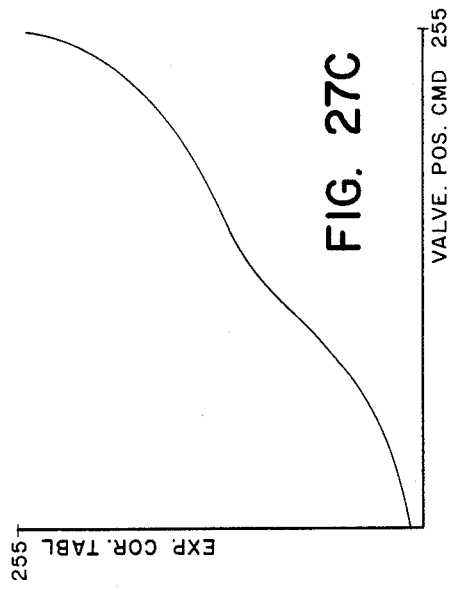
FIGS. 27A, 27B and 27C are graphs showing function values utilized in the software embodiment of this invention.
Figure 27A:
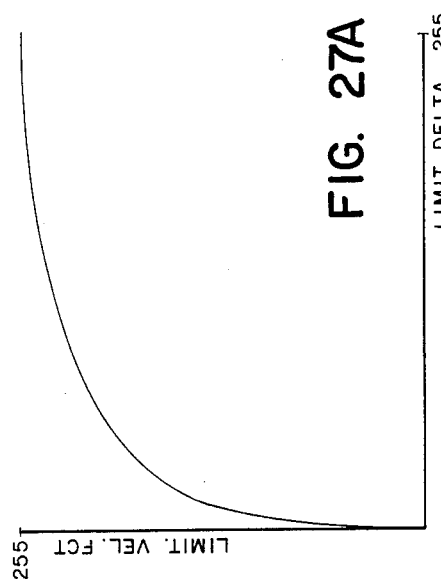
Figure 27B:
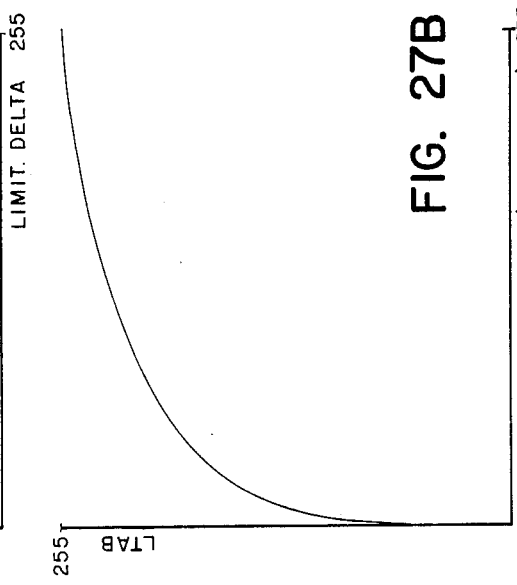

The digital routine for determining the torque and velocity baseline values will provide accurate baseline values which will track during the operation of the exercise system of this invention. The combination of providing velocity baseline correction and velocity calibration factor correction provides for more accurate control over the measured velocity of the system which is an integral, important parameter in overall control to maintain isokinetic behavior of the system. FIG. 27B illustrates the LTAB function which is used in several places in the 100 Hz software routine illustrated in FIGS. 24A-E. FIG. 27C illustrates the exponential correction table function designated EXP.COR.TABL in FIG. 24D. FIG. 27A illustrates the limit velocity function curve designated LIMIT.VEL.FCT in FIG. 24B. The corresponding actual table values are given in Tables 1, 2 and 3 attached hereto.

6. CONTROL MODE FLEXIBILITY PROVIDED BY THE DIGITAL SIGNAL PROCESSING EMBODIMENT OF THE SYSTEM AND METHOD OF THIS INVENTION

From the above description of the digital signal processing embodiment of this invention, it should be apparent that this implementation provides the possibilities for introducing a wide variety of exercise control modes in addition to the basic isokinetic control mode discussed. The software which produces the final value of the COR.POS.CMD which is sent to the error summing circuit to control the setting of the flow control valve can implement many different functional relationships between the measured parameters. For example, instead of an isokinetic velocity function modified only by a limits demand velocity as the lever arm approaches the upper and lower limit settings, the UNCOR.VEL.-DEM value could have a continuous functional relationship to the lever position such that the maximum permitted velocity varies as a predetermined function of lever position.

In addition, implementation of the velocity control computer in the form of a digital computer system provides additional data processing and real time control possibilities. It is a simple matter, for example, for the digital computer system to calculate on a continuous basis the accumulated work performed during the exercise motion, and this calculation can be performed separately for the muscle groups involved in flexion and extension, if desired. The computer can be programmed to calculate and display to the patient the peak torque being developed during the exercise motion. It can be programmed to determine the maximum range of motion of the involved joint by detecting the angle peak values and this range of motion calculation can be averaged over several exercise motions.

Employment of a programmed digital computer system permits a variety of anatomical demand velocity functions to be experimented with to determine whether variations from isokinetic anatomical rotation would be preferable for certain rehabilitation situations or for certain human performance improvement exercise regimens. For example, an isometric hold could be programmed into the anatomical velocity demand function at the point that the muscle group is developing peak torque and this could be implemented on the basis that the computer itself determines the angle value at which the velocity demand signal should go to zero for the isometric hold on the basis of actual torque versus angle measurements made on one or more trial exercise motions. As another example, sine wave velocity control functions could be used to increase or decrease the maximum permitted angular velocity during the midrange of the exercise motion. These functions could also be set up based on trial exercise runs which provide data on the total range of motion of the joint.

Implementation of the velocity control computer in the form of a digital computer system greatly enhances the processing of data related to the exercise performed on the system during the individual exercise bout as well as over the time span of a rehabilitation or muscle training program. Ultimately, exercise regimens may be set up for a particular rehabilitation program for an individual patient and the computer system will automatically follow the regimen from one exercise session to the next, each time tracking and reporting whether the anticipated progress is being achieved so that adjustments can be made in the regimen as necessary. This can be accomplished by downloading the control variables from a remote computer to the on-board computer. This could be done for individual patients based solely on the input of the patient number, for example. The remote computer could access a stored data file for that patient and download the settings for the next exercise bout automatically into the on-board computer. The remote computer could be programmed to display to the patient exercising the instructions for the exercise regimen as well as provide feedback to the patient on progress of achieving the goals of the currently programmed exercise bout.

7. THE ACTUATOR AND FLOW CONTROL VALVE COMPONENTS EMPLOYED IN THE SYSTEM OF THIS INVENTION

FIGS. 30–33 illustrate the currently preferred form of hydraulic actuator and solenoid control valve system which is employed as the rotational velocity governing system in a preferred embodiment of this invention. The main components of the rotational velocity governing system are a hydraulic actuator 450, an interface manifold 451, a dual solenoid control valve system 452, and a hydraulic reservoir system 453. These components function together with the velocity control computer system to provide the accommodating resistance for a lever arm mounted on the shaft 458 of the hydraulic actuator.

Referring to FIGS. 30 and 31, it is seen that the actuator 450 includes a generally cylindrical housing 455 which defines an interior cavity which is closed by the end caps 456 and 457. The shaft 458 is journaled in bearings 459 and 460 in the end caps 456 and 457. O-ring seals 461A and 461B seal the end cap 457 against leakage of hydraulic fluid from the interior cavity. Similarly O-ring seals 462A and 462B seal the end cap 456 against hydraulic fluid leakage.

A stationary vane 464 is mounted to the housing 455 and cooperates with the rotating vane 453 mounted on the shaft 458 to divide the hollow interior of the actuator into two complementary volume chambers. Hydraulic flow ports 465 and 466 are formed in the stationary vane 464 and the cylindrical housing 455 to communicate hydraulic fluid in two directions in and out of the complementary internal chambers of the actuator.

Manifold system 451 is mounted on top of the actuator housing 455 and includes a first fluid coupling channel 470 nd a second fluid coupling channel 473 respectively associated with the complementary internal chambers within the actuator. The flow channel 470 includes an inlet port 471 and a pair of outlet ports 472A and 472B which communicate hydraulic fluid into the flow control valve to be described below. The second flow channel 473 includes an entry port 474 and a single outlet port 475 communicating with the flow control valve as described below. Each of the manifold flow channels 470 and 473 have a pressure transducer 476 and 477, respectively mounted therein to monitor the pressure in each of these flow channels. These pressure transducers have electrical outputs which are utilized to measure the torque on the shaft as a function of the difference between hydraulic pressure in the two flow channels.

FIGS. 30 and 32 best illustrate the fluid coupling relationship between the manifold assembly 451 and the flow control valve assembly 452. The flow control valve assembly 452 includes a valve body having an internal chamber divided into three regions 486, 487 and 488. Chamber region 486 is in communication through an entry port 485B to receive fluid exiting the exit port 472B of the manifold system. Fluid outlet port 472A communicates through an entry port 485A into the chamber region 488 of the flow control valve. Thus hydraulic fluid from one of the compartments of the actuator flows through the manifold channel 470 into the two outer chamber portions 486 and 488 of the flow control valve. The outlet port 475 of the manifold communicates through an inlet port 484 to the central valve chamber portion 487.

The valve spool 483 includes a pair of valve seats 483A and 483B which control the flow into and out of the central chamber 487 from the outer chambers 486 and 488. Depending on the position of the valve spool 483 the effective flow orifice between the center chamber and the two outer chambers is controlled in size but with equal orifice sizes so that a balanced set of forces are acting on the valve spool 483. In other words the flow is in two directions, either from center to outer chambers or from outer chambers to inner chamber.

The two solenoids 480 and 481 are connected in push-/push relation. As discussed in connection with the electrical circuitry, the solenoid systems 480 and 481 are driven in a manner such that their average energization controls the position of the valve spool 483. A position measuring system 482 is associated with the solenoid assembly 480 and provides the position information on the actual position of the valve stem 483. This is used in the electrical control circuitry as previously discussed.

The hydraulic fluid reservoir system 453 provides a number of important functions in connection with the flow control valve system. Referring to FIG. 33, the arrangement is shown which provides the communication of the valve with the reservoir. At two of the highest points on each side of the chambers 487 and 488, there is a little channel vertically with each one having a check valve assembly 491, 492 mounted therein. Each of these check valves comprises a spring that supports a ball against a ball seat formed in a channel that communicates into the chamber 495 of the reservoir. Also shown here in between those two passages are the two channels 493 and 494 that contain very small orifices for providing a reverse leak feature whose function is described below. The reservoir chamber 495 has a piston mounted therein with spring pressure provided by spring 498 to keep the oil under a mild pressure. This pushes oil into the flow control valve and actuator as required.

When the temperature of the system rises the oil expands more rapidly than its metal container of the actuator, oil can then be forced into the reservoir through these orifices and the plunger is then pushed back relatively to accept this pressure increase. This provides a volume for the expanded oil to occupy. Otherwise the orifices 493 and 494 serve no function. The orifices provide a small controlled leakage past the check valve, otherwise the function of the two check valves is to prevent any point in the system from developing a negative pressure, particularly a negative pressure that would be sufficient to cause cavitation in the oil. If the actuator is being pushed in one direction you get a relative increase of pressure on one port and decrease on the other port. If that decrease starts to go below one atmosphere, i.e. lower than ambient pressure, the check valve opens up and oil is accepted in that passage from the reservoir.

Under conditions of very high torque, some oil will be pushed through one of the small orifices into the reservoir and then back through the check valve on the other side into the flow control valve chamber. This flow is through the orifices is quite small compared to the other leaks in the system, such as leakage past the moving an stationary vanes in the actuator. Thus the orifice leakage does not have a significant effect on operation of the overall velocity governor system.

The filling of the actuator, flow control valve and reservoir is performed in this manner. First all of the air is removed from the valve and the the actuator by removing the check valves 491 and 492 and then remounting the reservoir. The a hose is attached to the fill hole 496. The hose is in communication with a chamber filled with oil that has been evacuated so that all the air bubbles inside expand and get very large and are easily drawn out through the passages into the reservoir and out into the outer chamber. The system is repressurized and the result is an overall system that has a negligible amount of air in it.

The system is then filled to the level of the check valves. Next the check valves are replaced by removing the reservoir and replacing the balls and springs.

Then the plunger is drawn back to a certain position defined by the hole 499 with the filler cap 496 off, and next the reservoir is filled with oil to the position of the cap. The cap is installed and then the piston 498 released. At this point, there is a small oil pressure in the reservoir developed by the spring action of the piston and the system is sealed.

The various embodiments of an exercise system in accordance with this invention which are described above are given by way of example only and it should be understood that persons of skill in the various arts involved in this invention could make numerous modifications therein without departing from the scope of this invention as claimed in the following claims.

What is claimed is:

1. In a muscle exercise and diagnostic system, shaft means defining a fixed axis of rotation; a lever arm; arm coupling means for coupling said lever arm to said shaft means for rotation about said fixed axis; body coupling means for coupling a selected portion of the human body to said lever arm for rotation with said lever arm about an anatomical axis of rotation associated with said body portion; one of said arm coupling means and said body coupling means establishing a fixed tangential mounting relation and a freely sliding radial mounting relation between said lever arm and said associated element coupled thereto so that the distance between said body coupling means and said fixed axis of rotation may freely change during an exercise motion; and velocity control means operatively associated with said shaft means for limiting the maximum permitted rotational velocity of said arm to a value predetermined in accordance with a preselected velocity control function.

2. The system of claim 1, wherein said arm coupling means comprises means fixedly connecting said lever arm to said shaft means at a predefined point on said lever arm; and said body coupling means comprises means establishing a fixed tangential mounting relation and a free radially sliding mounting relation between said selected body portion and said lever arm.

3. The system of claim 1, wherein said body coupling means comprises means fixedly connecting said selected body portion to said lever arm at a predefined point; and said arm coupling means comprises means establishing a fixed tangential mounting relation and a free radially sliding mounting relation between said lever arm and said shaft means.

4. The system of claim 1, wherein said velocity control means includes range of motion limit means for defining at least one limit position in one direction of rotation of said lever arm and setting the maximum permitted rotational velocity of said lever arm to substantially a zero value when said lever arm is at said one limit position.

5. The system of claim 4, wherein said range of motion limit means includes means for gradually decelerating said lever arm to a stop at said one limit position.

6. The system of claim 4, wherein said range of motion limit means defines a second limit position in an opposite direction of rotation from said one direction and sets the maximum permitted rotational velocity of said lever arm to substantially a zero value when said lever arm is at said second limit position.

7. The system of claim 6, wherein said range of motion limit means includes means for gradually decelerating said lever arm to a stop at said one limit position and said second limit position.

8. The system of claim 4, wherein said range of motion limit means includes limit storing means adapted to store a limit position value corresponding to said one limit position, and a limit programming switch adapted to be operated when said lever arm is physically moved to said one limit position to enable said limit storing means to store said limit position value.

9. The system of claim 4, further comprising position measuring means for producing a position output signal corresponding to the angular position of said lever arm; and wherein said range of motion limit means includes limit storing means adapted to store a first limit position value and a second limit position value, a first limit switch means operative when said lever arm is placed in a first limit position to enable said limit storing means to store the current value of said position output signal as said first limit position value, and a second switch means operative when said lever arm is placed in a second limit position to enable said limit storing means to store the current value of said position output signal as said second limit position value.

10. The system of claim 9, wherein said range of motion limit means includes active limit means for designating one of said first limit position value and said second limit position value as an active limit value based on the current direction of rotation of said lever arm; and said preselected velocity control function includes the difference between the current value of said position output signal and said active limit value.

11. The system of claim 9, wherein said position measuring produces an analog position output signal; said system further comprises converter means for converting said analog position output signal to a digital position signal; and wherein said limit storing means comprises digital storage means for storing said first limit position value and said second limit position value as respective first and second digital position signal values, said first limit switch means enables said digital storage means to store said first digital position signal value and said second limit switch means enables said digital storage means to store said second digital position signal value.

12. The system of claim 1, wherein said velocity control means includes range of motion limit means defining a permitted range of motion of said lever arm between a first limit position in a first direction of rotation and a second limit position in a second direction of rotation, said range of motion limit means comprising limit storing means for storing a first limit position signal corresponding to said first limit position and a second limit position signal corresponding to said second limit position, first switch means for enabling storage of said first limit position signal when said lever arm is moved to a first limit position, and second switch means for enabling storage of said second limit position signal when said lever arm is moved to said second limit position.

13. The system of claim 12, wherein said velocity control means gradually decelerates said lever arm toward a zero velocity as said lever arm approaches one of said first and second limit positions.

14. The system of claim 1, further comprising position measuring means for producing an output signal corresponding to the angular position of said lever arm; wherein said velocity control means includes range of motion limit means defining a permitted range of angular motion of said lever arm, said range of motion limit means comprising limit storage means for storing first and second limit signals, first switch means for enabling said limit storage means to store the value of said output signal from said position measuring means as said first limit signal when said lever arm is moved to a first angular limit position, and second switch means for enabling said limit storage means to store the value of said output signal from said position measuring means as said second limit signal when said lever arm is moved to a second angular limit position.

15. The system of claim 14, wherein said velocity control means gradually decelerates said lever arm toward a zero velocity as said lever arm approaches one of said first and second angular limit positions as a function of the difference between the value of said output signal from said position measuring means and the value of an associated one of said first and second limit signals.

16. The system of claim 14, wherein said velocity control means comprises digital computer control means including a central processing unit, program memory means for storing a computer operating program, parameter memory means for storing a plurality of operating parameters, and digitizing means for converting a plurality of analog parameter signal values into corresponding digital parameter signal values for storage in said parameter memory means, said position measuring means producing an output analog signal, said first switch means enabling said digital computer control means to digitize and store in said parameter memory means the value of said output signal from said position measuring means when said lever arm is positioned at one of said first limit position and second limit position.

17. The system of claim 14, wherein said position measuring means produces an output analog position signal, said limit storage means comprises digital memory means for storing signal values in the form of a digital word value, and said velocity control means includes converter means for converting analog signal values to corresponding digital signal values; said first switch means enables storage in said digital memory means of a first digital word value corresponding to the analog signal output value of said position measuring means when said lever arm is at said first angular limit position and said second switch means enables storage in said digital memory means of a second digital word value corresponding to the analog signal output value of said position measuring means when said lever arm is at said second angular limit position.

18. In an exercise system, shaft means defining a fixed axis of rotation; coupling means, including a rigid lever arm, for coupling a preselected point on a preselected body portion to said shaft for combined rotation about said fixed axis of rotation and an anatomical axis of rotation associated with said body portion in a plane orthogonal to said fixed axis with a fixed tangential coupling relationship between said preselected point and said shaft and a freely alterable radial coupling relationship between said preselected point and said shaft during said rotation; and velocity control means coupled to said shaft means for limiting the maximum permitted rotational velocity of said shaft to a value predetermined in accordance with a preselected velocity control function.

19. The exercise system of claim 18, wherein said velocity control means comprises a rotational velocity governor system responsive to an input velocity control signal to limit the maximum permitted instantaneous rotational velocity of said shaft means during an exercise motion; and velocity control computer means for supplying a velocity control signal to said rotational velocity governor system, said velocity control computer means comprising a digital computer means including program memory means storing a prearranged computer operating program and parameter memory means for storing a plurality of parameter values, and further comprising means for measuring and storing in said parameter memory means an initial lever length data value comprising the distance from said preselected point on said body portion to said anatomical axis of rotation of said body portion when said anatomical axis is substantially aligned with said fixed axis; means for continuously sampling and storing in said parameter memory means a current lever length data value comprising the distance between said preselected point and said fixed axis during said exercise motion; and means establishing and storing in said parameter memory means an anatomical velocity demand function; said digital computer means utilizing said prearranged computer operating program for calculating and supplying a velocity control signal to said governor system throughout said exercise motion as a prearranged functional combination of said stored anatomical velocity demand function, said stored initial lever length data value and said stored current lever length data value.

20. The exercise system of claim 19, wherein said rotational velocity governor system comprises a rotary hydraulic acutator with a rotationally mounted shaft extending therethrough and carrying a rotating vane cooperating with a stationary vane on the interior of said actuator to define two complementarily variable volumetric chambers on opposite sides of said vanes and a pair of fluid ports each communicating with one of said chambers; a fluid control valve comprising at least a pair of fluid ports communicating with said fluid ports of said actuator, an internal valve spool for controlling the effective orifice size of said fluid ports and regulating the flow of fluid therebetween, and valve position drive means responsive to an input valve position control signal to control the position of said value spool; and said velocity control computer means includes means for continuously sampling and storing in said parameter memory means a torque data value corresponding to the value of torque on said shaft during said exercise motion and said digital computer means utilizes said prearranged computer operating program for computing a velocity control signal in the form of a valve position drive signal supplied to said valve position drive means and comprising a predictive value calculated as a combined function of said stored torque data value, said stored anatomical velocity demand function, said stored initial lever length data value and said stored current lever length data value.

21. The system of claim 20, further comprising means for measuring and storing in said parameter storing means a current velocity data value corresponding to the actual angular velocity of said lever arm during said exercise motion, and said prearranged functional combination includes said current velocity data value.

22. In a muscle exercise and diagnostic system, a lever arm; means coupling said lever arm to a shaft for rotation with said shaft about a mechanical axis of rotation; means establishing a velocity demand signal; and a rotational velocity governor system coupled to said shaft for limiting the rotational velocity thereof; and control means for controlling said governor system in response to said anatomical velocity demand signal; said governor system comprising a rotary hydraulic actuator with a rotationally mounted shaft extending therethrough and carrying a rotating vane cooperating with a stationary vane on the interior of said actuator to define two complementarily variable volumetric chambers on opposite sides of said vanes and a pair of fluid ports each communicating with one of said chambers; a fluid control valve comprising at least a pair of fluid ports communicating with said fluid ports of said actuator, an internal valve spool for controlling the effective orifice size of said fluid ports and regulating the flow of fluid therebetween, and valve position drive means responsive to an input valve position control signal to control the position of said value spool; and said control means comprises angle measuring means for measuring the angular position of said lever arm and shaft and producing an analog angle signal corresponding thereto, velocity measuring means receiving said angle signal for computing the velocity of said lever arm and shaft and producing an analog velocity signal corresponding thereto, torque measuring means for measuring the value of torque exerted on said shaft and producing an analog torque signal corresponding thereto; analog to digital converter means for digitizing said analog velocity signal and said analog torque signal to corresponding digital velocity and torque signals corresponding thereto; digital computer means, including program means and input/output means, for receiving said digital signals and said velocity demand signal and computing a digital valve position command signal; and digital to analog converter means receiving said digital valve position command signal for producing a corresponding analog valve position command signal and supplying said signal to said valve position drive means; said program means including baseline correction routine means for analyzing said digital angle signals to determine when said lever arm is in a quiescent condition and thereupon computing baseline values of said digital velocity and torque signals from said analog velocity and torque signal; baseline correction routine means for correcting digital velocity and torque signals based on said computed baseline values thereof; a velocity demand correction routine for calculating the current system error based on the digital value of measured velocity and said input velocity demand signal and calculating a corrected velocity demand signal as a prearranged function of said calculated system error and said input velocity demand signal; a torque computation routine for calculating the absolute value of said digital torque signal; a torque factor routine for calculating a torque factor as a prearranged function of said absolute torque value; a valve position command routine for calculating a valve position command as a prearranged function of said corrected velocity demand signal and said torque factor; and a correction routine for converting said valve position command signal to a corrected valve position command signal based on looking up a corrected value in a stored table of correction values.

23. The system of claim 22, wherein said analog to digital converter means also receives said analog angle signal for converting said signal to a digital angle signal; said computer means receives said digital angle signal; and said program means further includes a velocity calibration routine means for calculating a velocity calibration factor, including a routine for calculating velocity as a function of change in said digital angle signal, a routine for calculating the absolute value of said calculated velocity; a routine for calculating the average value of said digital velocity value, a routine for calculating the absolute value of said average digital velocity value, a routine for calculating a new velocity calibration value as a prearranged function of the prior velocity calibration value, the absolute value of said calculated velocity, the absolute value of said average digital velocity value, and the value of a previously calculated velocity calibration factor; and a routine for calculating a velocity calibration factor as a prearranged function of said new velocity calibration value; and said velocity demand correction routine calculates current system error based on actual digital velocity value modified by said velocity calibration factor.

24. The system of claim 22, wherein said program means includes means establishing a velocity/torque correction factor array having a two dimensional relationship to velocity and torque parameters; a velocity/torque correction factor look up routine for looking up a velocity/torque correction factor value in said array based on value of velocity and torque; and a routine for updating the value of said velocity/torque correction factor in said array based on said calculated system error; and wherein said valve position command routine calculates said valve position command value partially as a function of said velocity/torque correction factor.

25. The system of claim 22, further comprising patient coupling means cooperating with said lever arm and said means coupling said lever arm to said shaft to provide a tangentially fixed and radially alterable patient attachment point and a correspondingly variable lever length during an exercise motion; initial lever length means for registering the patient lever length when the anatomical axis of rotation is aligned substantially with the axis of said shaft; and lever length tracking means for continuously tracking the current lever length during the exercise motion and producing an analog current lever length signal corresponding thereto; said analog to digital converter means converts said analog current lever length signal to a corresponding digital lever length signal; said computer means receives said digital lever length signal; and said program means includes a routine for proportioning said velocity demand signal in accordance with the ratio of said initial lever length signal and said digital current lever length signal.

26. In a method for controlled resistance exercise: the steps of:
mounting a shaft for rotation about a fixed axis;
coupling a preselected point on a human body portion to said shaft through a rigid lever arm for enabling combined rotation of said lever arm about said fixed axis and said human body portion about an anatomic axis in the vicinity of said fixed axis with a coupling relation comprising a fixed tangential relation and a freely alterable radial relation between said preselected point and said shaft during said combined rotation; and
limiting the maximum permitted rotational velocity of said shaft to a value predetermined in accordance with a preselected velocity control function.

27. The method claimed in claim 26, adapted to be carried out through the use of a programmed digital computer which includes parameter memory means for storing a plurality of parameter data values and comprising the steps of:
storing in said parameter memory means an initial lever length data value comprising the distance from said preselected point on said body portion to said anatomical axis of rotation of said body portion when said anatomical axis is substantially aligned with said fixed axis;
measuring in at least a substantially continuous manner the distance between said preselected point and said fixed axis during said rotation;
sampling said measured distance at regular intervals during said rotation to produce a current lever length data value;
storing said current lever length data value in said parameter memory means
defining an anatomical velocity demand function;
calculating in said digital computer an instantaneous maximum permitted rotational velocity value for said shaft means as a prearranged functional combination of said initial lever length data value, said current lever length data value, and said anatomical velocity demand function; and
limiting the rotational velocity of said shaft means to a said instantaneous maximum permitted rotational velocity value.

28. The method of claim 27, further including the steps of:
defining at least one limit value on the angular position of said lever arm and said body portion;
storing said defined limit value in said parameter memory means;
measuring the actual angular position of said lever arm during said rotation thereof;
sampling said measured angular position at regular intervals during said motion to produce a current position data value;
storing said current position data value in said parameter memory means; and
and wherein said step of calculating an instantaneous maximum permitted rotational velocity value is performed using a prearranged functional combination of said initial lever length data value, said current lever length data value, said anatomical velocity demand function, said current position data value and said defined limit value such that said maximum permitted rotational velocity value approaches zero as said current position data value approaches said defined limit value.

29. In a method for controlling the maximum permitted shaft velocity of a velocity governing system comprising a rotary hydraulic actuator with a rotationally mounted shaft having a rotating vane carried thereon and cooperating with a stationary vane on the interior of said actuator to define two complementarily variable volumetric chambers on opposite sides of said vanes, and a pair of fluid ports each communicating with one of said chambers; a fluid control valve comprising at least a pair of fluid ports communicating with said fluid ports of said actuator, an internal valve spool for controlling the effective orifice size of said fluid ports and regulating the flow of fluid therebetween, and valve position drive means responsive to an input valve position control signal to control the position of said valve spool, the steps of:

establishing a shaft velocity demand signal;

measuring the actual torque on said shaft of said actuator;

calculating a valve position command signal based on a predetermined functional combination of said demand signal and said measured actual torque;

measuring and registering the instantaneous value of actual shaft velocity;

calculating a current system error signal based on a predetermined functional combination of said measured actual shaft velocity and said shaft velocity demand signal;

correcting said shaft velocity demand signal as a function of said calculated current system error;

establishing a two dimensional array of correction signal data points, each data point corresponding to prearranged ranges of values of said shaft velocity demand signal and said measured actual torque signal and storing a velocity/torque correction signal value;

addressing an active one of said data points based on the current measured torque value and the current value of the shaft velocity demand signal;

reading the stored velocity/torque correction signal value stored at said active data point; and storing at said active data point a new velocity/torque correction signal value as a prearranged functional combination of the correction signal value read and the value of the current system error;

and wherein said step of calculating a valve position command signal is performed on the basis of a predetermined functional combination of said shaft velocity demand signal, said measured torque signal and said read velocity/torque correction signal value.

30. The method of claim 29, further comprising the steps of:

calculating baseline values of said measured shaft velocity and said measured shaft torque when said shaft is not moving; and calculating corrected values of said shaft velocity and said measured torque based on said calculated baseline values.

31. The method of claim 30, further comprising the steps of:

measuring and registering the instantaneous value of actual shaft angle;

calculating actual shaft velocity as a function of changes in said measured values of shaft angle;

calculating a velocity calibration factor as a prearranged function of said measured actual shaft velocity and said calculated actual shaft velocity;

and wherein said step of calculating a current system error is performed on the basis of modifying said measured actual shaft velocity as a function of said calculated velocity calibration factor.

32. In a method for controlled accommodating resistance exercise, the steps of:

mounting a shaft for rotation about a fixed axis;

coupling a preselected point on a human body portion to said shaft through a rigid lever arm for enabling combined rotation of said lever arm about said fixed axis and said human body portion about an anatomic axis in the vicinity of said fixed axis with a coupling relation comprising a fixed tangential relation and a freely alterable radial relation between said preselected point and said shaft during said combined rotation;

registering an initial lever length comprising the distance from said preselected point on said body portion to said anatomical axis of rotation of said body portion when said anatomical axis is substantially aligned with said fixed axis;

registering in at least a substantially continuous manner the distance between said preselected point and said fixed axis during said rotation;

defining an anatomical velocity demand function; and limiting the instantaneous maximum permitted rotational velocity of said shaft means to a value which is determined in accordance with a prearranged functional combination of said anatomical velocity demand function, said registered initial lever length and said registered distance using a velocity governing system comprising a rotary hydraulic actuator with a rotationally mounted shaft having a rotating vane carried thereon and cooperating with a stationary vane on the interior of said actuator to define two complementarily variable volumetric chambers on opposite sides of said vanes; and a pair of fluid ports each communicating with one of said chambers; a fluid control valve comprising at least a pair of fluid ports communicating with said fluid ports of said actuator, an internal valve spool for controlling the effective orifice size of said fluid ports and regulating the flow of fluid therebetween, and valve position drive means responsive to an input valve position control signal to control the position of said value spool, said limiting step. including the steps of:

measuring the actual torque on said shaft of said actuator;

measuring and registering the instantaneous value of actual shaft velocity;

calculating a current system error signal based on a predetermined functional combination of said measured actual shaft velocity and said shaft velocity demand signal;

correcting said shaft velocity demand signal as a function of said calculated current system error;

establishing a two dimensional array of correction signal data points, each data point corresponding to prearranged ranges of values of said shaft velocity demand signal and said measured actual torque signal and storing a velocity/torque correction signal value;

addressing an active one of said data points based on the current measured torque value and the current value of the shaft velocity demand signal;

reading the stored velocity/torque correction signal value stored at said active data point;

storing at said active data point a new velocity/torque correction signal value as a prearranged functional combination of the correction signal value read and the value of the current system error; and calculating a valve position command signal based on a predetermined functional combination of said anatomical velocity demand function, said registered initial lever length, said registered distance, said measured actual torque, and said velocity/torque correction signal value.

33. The method of claim 32, further comprising the steps of:
calculating baseline values of said measured shaft velocity and said measured shaft torque when said shaft is not moving; and
calculating corrected values of said shaft velocity and said measured torque based on said calculated baseline values.

34. The method of claim 33, further comprising the steps of:

measuring and registering the instantaneous value of actual shaft angle;
calculating actual shaft velocity as a function of changes in said measured values of shaft angle;
calculating a velocity calibration factor as a prearranged function of said measured actual shaft velocity and said calculated actual shaft velocity;
and wherein said step of calculating a current system error is performed on the basis of modifying said measured actual shaft velocity as a function of said calculated velocity calibration factor.

* * * * *